(12) United States Patent
Jiang et al.

(10) Patent No.: US 7,662,564 B2
(45) Date of Patent: Feb. 16, 2010

(54) POLYMORPHISMS IN MITOCHONDRIAL TRANSCRIPTION FACTOR A ("TFAM") GENE AND THEIR ASSOCIATIONS WITH MEASURES OF MARBLING AND SUBCUTANEOUS FAT DEPTH IN BEEF CATTLE

(75) Inventors: Zhihua Jiang, Pullman, WA (US); Tanja Kunej, Ljubljana (SI)

(73) Assignee: Washington State University Research Foundation, Pullman, WA (US)

( * ) Notice: Subject to any disclaimer, the term of this patent is extended or adjusted under 35 U.S.C. 154(b) by 117 days.

(21) Appl. No.: 11/441,928

(22) Filed: May 26, 2006

(65) Prior Publication Data
US 2007/0065843 A1    Mar. 22, 2007

Related U.S. Application Data

(60) Provisional application No. 60/685,213, filed on May 27, 2005.

(51) Int. Cl.
*C12Q 1/68* (2006.01)
(52) U.S. Cl. .......................................... 435/6; 435/91.2
(58) Field of Classification Search ........................ None
See application file for complete search history.

(56) References Cited

U.S. PATENT DOCUMENTS

2008/0183394 A1 *  7/2008  Woodward ................... 702/19

OTHER PUBLICATIONS

Juppner et al. Bone. vol. 17, No. 2 Supplement. Aug. 1995, 39S-42S.*
Mummidi et al. The Journal of Biochemistry, vol. 275, No. 25, pp. 18946-18961.*
Alam TI, Kanki T, Muta T, Ukaji K, Abe Y, Nakayama H, Takio K, Hamasaki N, Kang D. Human mitochondrial DNA is packaged with TFAM. Nucleic Acids Res. Mar 15, 2003:31(6):1640-5.
Ekstrand MI, Falkenberg M. Rantanen A, Park CB, Gaspari M. Hultenby K, Rustin P, Gustafsson CM, Larsson NG. Mitochondrial transcription factor A regulates mtDNA copy number in mammals. Hum Mol Genet. May 1, 2004;13(9):935-44. Epub Mar. 11, 2004.
Fisher RP, Clayton DA. Purification and characterization of human mitochondrial transcription factor 1. Mol Cell Biol. Aug. 1988;8(8):3496-509.
Garstka HL, Schmitt WE, Schultz J, Sogl B, Silakowski B, Perez-Martos A, Montoya J, Wiesner RJ. Import of mitochondrial transcription factor A (TFAM) into rat liver mitochondria stimulates transcription of mitochondrial DNA. Nucleic Acids Res. Sep. 1, 2003;31(17):5039-47.
Gaspari M, Larsson NG, Gustafsson CM. The transcription machinery in mammalian mitochondria. Biochim Biophys Acta. Dec. 6, 2004:1659(2-3):148-52.
Jiang Z, Kunej T, Michal JJ, Gaskins CT, Reeves JJ, Busboom JR, Dove P, Wright RW Jr. Significant associations of the mitochondrial transcription factor A promoter polymorphisms with marbling and subcutaneous fat depth in Wagyu x Limousin F2 crosses. Biochem Biophys Res Commun. Aug. 26, 2005;334(2):516-23.
Kanki T, Nakayama H, Sasaki N, Takio K, Alam TI, Hamasaki N, Kang D. Mitochondrial nucleoid and transcription factor A. Ann NY Acad Sci. Apr. 2004;1011:61-8.
Kanki T, Ohgaki K, Gaspari M, Gustafsson CM, Fukuoh A, Sasaki N, Hamasaki N, Kang D. Architectural role of mitochondrial transcription factor A in maintenance of human mitochondrial DNA. Mol Cell Biol. Nov. 2004:24(22):9823-34.
Owen OE, Kalhan SC, Hanson RW. The key role of anaplerosis and cataplerosis for citric acid cycle function. J Biol Chem. Aug. 23, 2002:277(34):30409-12. Epub Jun. 26, 2002.
Reichert AS, Neupert W. Mitochondriomics or what makes us breathe. Trends Genet. Nov. 2004;20(11):555-62.
Wilson-Fritch L, Burkart A, Bell G. Mendelson K, Leszyk J, Nicoloro S. Czech M, Corvera S. Mitochondrial biogenesis and remodeling during adipogenesis and in response to the insulin sensitizer rosiglitazone. Mol Cell Biol. Feb. 2003:23(3):1085-94.
Wilson-Fritch L. Nicoloro S, Chouinard M, Lazar MA, Chui PC, Leszyk J, Straubhaar J, Czech MP, Corvera S. Mitochondrial remodeling in adipose tissue associated with obesity and treatment with rosiglitazone. J Clin Invest. Nov. 2004:114(9):1281-9.

* cited by examiner

*Primary Examiner*—Juliet C Switzer
(74) *Attorney, Agent, or Firm*—Judy Jarecki-Black; Merial Limited; Thomas Kowalski, Esq.

(57) ABSTRACT

The physiological regulation of intake, growth and energy partitioning in animals is under the control of multiple genes, which may be important candidates for unraveling the genetic variation in economically relevant traits in beef production. The present invention relates to the identification of single nucleotide polymorphisms (SNPs) within the bovine gene encoding mitochondrial transcription factor A ("TFAM") and their associations with economically relevant traits in beef production. The invention further encompasses methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

1 Claim, 15 Drawing Sheets

| | |
|---|---|
| -1699 | TAGATCAGATTTATAAGAACTTTATAGCAAGGCTTATCAAAATGACACTTTAAAACAACA |
| -1539 | AAGACTTTAAATATTCAAAAAAATTTTTTATATCTATCAAACGTCTGAAAGAATAAAAAC |
| -1479 | ACTCTAGAAAAATGTAAAGAAAAGTTGTTGCAGAAATCAGCTAAAATGTAATTATAAGGA |
| -1419 | ATTCTATCCCATACTTTTAGCTTGACATTGTAGTGTAACTGTTCATTTCTTTGCCTCTGC |
| -1359 | CACTAGACTTCATGGGCGGTGAAAAGAAGGCTGTGTTTTTTATCTAAGTTTGTGGCCTTG |
| -1299 | TACATAATGTGTACTCAGAAAATAATCAAACAAACAAAATCCAACCCTGTTTCTTCCATG |
| | ↓ -1220    ↓ -1212 |
| -1239 | ACAGAGTGAGAGATTTGG[T]CAGATGA[T]CTAAAAGGTCCCTTTCAATACTGAGAATTTTTG |
| | C           C |
| -1179 | AAAAGGAAGTGGTGATAGTTGCTTACCACTTAGAAGTGGGCTTGGTGGTCGCACTCAACG |
| -1119 | GGCCAGTGAAAGACTCTCAGCTCAATATGACACTAGTAAGAATTTTCTTACAAACCTATC |
| -1059 | CAACAGAGAAAAAGCTGTTTCAGGAAGTGGCTCTTTGAAATAAATGGAACCTGAGAGCTA |
| - 999 | GAAGTGTCCTTAGATAGCTTTAGATAAGGTTATCCTAATCTTTTTTCATGCCATTGTCCA |
| - 939 | CATGGAAAATGGCGGTACTGCACATCGATCAATATCTCAAGGCATAATTGTCACAGGTTC |
| - 879 | TCAGAGCTTTGGTTGGGAAATGATCTCGTCCAACATCCTCGTCTGCAGTGGGGAAATTA |
| - 819 | AATCTTACAGCGGGGAAGTGACATTTCCAGATCAAGACGTTAATGCAAATGATGGAGCTA |
| - 759 | GAACTCTAGTCTCCGGACAGATAACTAGTCAGTCTCCTCCCCACAAAGTAAGCAGGGTTG |
| - 699 | GATGTCAAGCTTGCCGATTAGGTCAGCGATAGTCTCAGTGGATGGGCTATGGTCTGGAT |
| - 639 | CTGTGTTGCTTTAAATGTGGTCCCATAACCACTGGCATCAGAGCTTGTTAAACCTTGAGG |
| - 579 | AACTTGTTAAGATAGCTGAGACATGGGACCCACACAAACACGGAATCAGGCTCTGCGGCA |
| - 519 | AGGCCCGGGAATCTGCATTTTAAGGTTAGAAACCGTGATCCATCCCACCTCCTCTACGGT |
| - 459 | AATTTTGGACTACGCGCTCCGACTTGAACTGAGGGACTCTGCTGGGCGCATATCGCCCAG |
| - 399 | CAACCTGACCTCAGAGCAGCGTGGGCGGCACGGCTACCGCCGTTCTAGCCGTAAACTGTC |
| - 339 | TGTTACGTACTAGCCCTTCCAGTCGTCACAAACCAGCCAGGGCCCCATCCGTGTGAGGAC |
| | SP1 |
| - 279 | ACCGCCGTGCCTCCAATCAGCCTCCTGGCCGGGCGGCTGAGCAGGCTGCCGGGGGGGTGG |
| - 219 | GGGGGTGGGGTTGGGACAGAGGCGGCTCAGCTTCGCCCCCTCGAGGCCAGGTCCCTCCGC |
| | Transcription repressor |
| - 159 | AGGCTAGCCGGGTTGCAGTTTCCCTTCTCCGCCTCCGAGCGCCTTTTTCTTCGTAGTCCC |
| | NRF1 |
| - 99 | GCCCACCAAGGAAGCCAGTACAGCGCCTGCGCCTTCTACCTTGCCCCGCCTCCTAGCTAA |
| | +1 (putative) → |
| - 39 | TCGGAAGTTAGCCGATTTCCCATAGTGCCCCGCGAGTGGCGGGCATGATAGTAAATCCGG |
| + 22 | TAGGCTCTCTGGCGGGTTAAGTCGGCTTTGTTGCGGTTTCTCTTGTGCCAGGGCGCTGT |
| | ATG  Exon 1 |
| + 82 | AGGGAATTGGGGCCTGGTCAGTGCTTTGTCTGCGGATGCA |
| + 142 | |
| + 202 | |

FIG. 2

AGATTTGGCCAGATGACCTAAAAG    AGATTTGGACAGATGATCTAAAAG

A. A third mutation detected in bovine TFAM promoter region
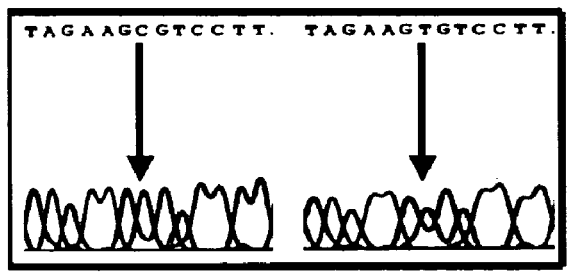
B. Two mutations detected in bovine TFB1M gene
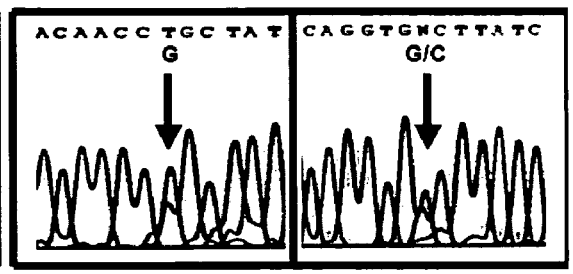
C. Five mutations detected in bovine TFB2M gene
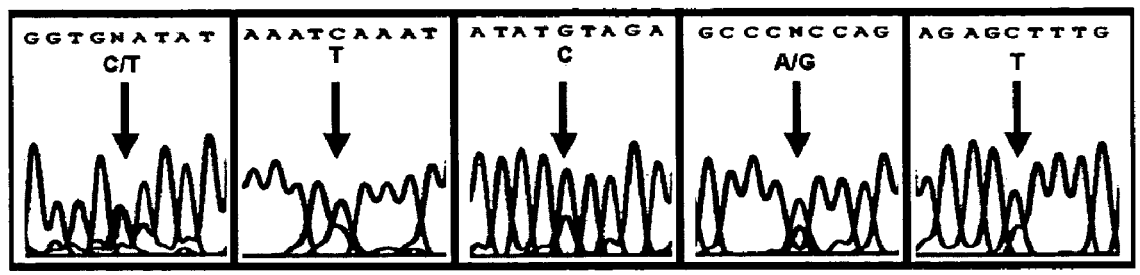
FIG. 5

```
CGGGCATGATAGTAAATCCGGTAGGCTCTCTGGCGGGTTTAAGTCGGCTTTGTTGCGGGTTCTCTTGTGCCAGGGCG
CTGTAGGGAATTGGGGCCTGGTCAGTGCTTTGTCTGCGGATGCAATGGCGCTTCTCCGGGGCGTATGGGGCGTGCTG
AATGCGCTGGGAAAGTCAGGAGCGGATCTCTGCGCGGGCTGTGGCAGTCGACTGCGCTCTCCCTTTAGTTTTGCGTA
TGTTCCAAAATGGTTTTCATCCAGCTTGAGTGGTTATCCAAAGAAGCCCATGACTTCATACGTTCGATTTTCTAAAG
AACAGCTGCCCATATTTAAAGCTCAGAACCCAGATGCAAAAAATTCAGAACTAATTAAAAAAATTGCCAAGCTATGG
AGGGAACTTCCTGATTCAGAGAAAAAGATATATGAAGATGCTTACAGGGCAGACTGGCAGGTATACAAGGAAGAGAT
AAACAGAATTCAAGAACAACTAACTCCAAGTCAAATGGTATCTTTGGAAAAAGAAATCATGCAGAAACGTTTAAAAA
AGAAAGCGTTAATAAAAAAGAGAGAGTTAACAATGCTTGGAAAACCGAAAAGACCTCGCTCAGCTTATAACATTTTT
ATAGCTGAACGTTTTCAGGAAGCTAGGGATGGCACATCACAGGTAAAGCTGAAAGCTATAAATGAAAACTGGAAAAA
TCTCTCTAATTCTCAAAAGCAAGTATATATTCAGCTTGCTAAAGATGATAAAATTCGTTATTATAACGAAATGAAAT
CTTGGGAGGAACAAATGATGGAAGTTGGACGAGAAGATCTTATACGTCGCTCAATTAAATACCCAGCAAAAAATGAC
CCTGAGAAGTTTTAAAATAGAAGATTGAGTTATGTTCATAATGGATAGACATAAGAAACCAACTAGGTCTCAATACC
GGAAGCTGTTGTAAAATTAGAATGGATAAAGTTGGTGAACATTTATATTTAATTCCTTTTCTGTAGCCCATGGACTT
CTGCCAGCCAATTCAATACATTTTGTATTGGTGTCTTGCTTTTGAAAACCCAAACAGATAAGACTTCATGTGGAATT
TATTTTGTGTTTAGGAACTACTGAGCATCAAAATAATCCATGAAATGTAGCAGTGAATCATTTTACCTTTGATAAAG
GTAAATCAGACTGTGAAGTTTTTTTATACTTGGTGATTATGGAAAAAATATTCTTGTTTCCTTATATTATGGAAGCA
GGAGTTTCCTATTCATAAGTATCTCAAAGTTTGTAGAAGCCATAGTGTTCTATGATATAACTGCATTTTTAAAAGAG
CATCCAGAACTCATGCTGGTAAATTCCAAATCCTGGGTATAATTCATATTATAATCAGACTTGATGGTTGTACATGT
GAGGAATTTCTGGTATCAGTTGCAGCTTTTATAAAAGGTATAGATTTATAAACCTTTTCCTCATTATCTTTTTCCTA
AATTAAAAACTAAAAAATTATGTACCAAATCTATGCATATTGTTTTATATTGCATAGAATAAAAATTATGTGTTTCC
TAATTATGTTTTAAGGTGAAACATTCATTTTATAGCTTTCTGGGATTTTTGTTTGTTTTTTAAACAAAGTAGGAGT
TTGTATACTGAATTATTTTTCTCTTATGTAAATATATTTATCCAGAAAGTAGAGAACTTATTTGGTGTAAGTTTTA
AAATGAGAGATCTAAAAAAATCATGTCTCCAAAGTCTCTCAAATTGGAACCTATAATTTTTAAACATTTGCATAACA
TATAAAAGCCTGTATAATAATTAATAGCCAGTTCTAGCCTGATGCCCACATCCAGCCCACTGCCTGCTTTTCTTGGC
CTTGTCAACTAAGAATTGTTCACAGTTTTAAATAGTTAAAAAAAACTAAGCATACTTCAAGACACATGAAAATTAAT
ATGAAATTCAGTGTCCATAAAAAAATGTTTTATTGGAACACAGCCACACTCATCGATTATGGCTGTTTTGTACAAT
AGTGCAGTTGACTTGGTTGCTACAGAGAGGTGCAGCCTGCAAAGACTGACCCGTATAGTGTGGAATGAGATGCTCTT
AAGTTACTTGCTGTGGCTCAGTAAAATACATCTTAACAGTTTTCCAGTTAGCATTTAAACCTTACCCCTTCTAGCAT
TTGATTATCTTCTTAACAAGAGTCAAAGGTTTTTCAAAATCCACACCACCTTTTTGAGCAAAATATTCAACTGTCAT
CATCAGTTCACATGAATTTATAACTC
```

FIG. 6A

TAGATCAGATTTATAAGAACTTTATAGCAAGGCTTATCAAAATGACACTTTAAAACAACAAAGACTTTAAATATTCA
AAAAAATTTTTTATATCTATCAAACGTCTGAAAGAATAAAAACACTCTAGAAAAATGTAAAGAAAAGTTGTTGCAGA
AATCAGCTAAAATGTAATTATAAGGAATTCTATCCCATACTTTTAGCTTGACATTGTAGTGTAACTGTTCATTTCTT
TGCCTCTGCCACTAGACTTCATGGGCGGTGAAAAGAAGGCTGTGTTTTTATCTAAGTTTGTGGCCTTGTACATAAT
GTGTACTCAGAAAATAATCAAACAAACAAAATCCAACCCTGTTTCTTCCATGACAGAGTGAGAGATTTGGACAGATG
AGCTAAAAGGTCCCTTTCAATACTGAGAATTTTTGAAAAGGAAGTGGTGATAGTTGCTTACCACTTAGAAGTGGGCT
TGGTGGTCGCACTCAACGGGCCAGTGAAAGACTCTCAGCTCAATATGACACTAGTAAGAATTTTCTTACAAACCTAT
CCAACAGAGAAAAAGCTGTTTCAGGAAGTGGCTCTTTGAAATAAATGGAACCTGAGAGCTAGAAGTGTCCTTAGATA
GCTTTAGATAAGGTTATCCTAATCTTTTTTCATGCCATTGTCCACATGGAAAATGGCGGTACTGCACATCGATCAAT
ATCTCAAGGCATAATTGTCACAGGTTCTCAGAGCTTTGGTTGGGAAATGATCTCGTCCAACATCCTCGTCTGCAGTG
GGGGAAATTAAATCTTACAGCGGGGAAGTGACATTTCCAGATCAAGACGTTAATGCAAATGATGGAGCTAGAACTCT
AGTCTCCGGACAGATAACTAGTCAGTCTCCTCCCCACAAAGTAAGCAGGGTTGGATGTCAAGCTTGCCGATTAGGTC
AGCGATAGTCTCAGTGGATGGGGCTATGGTCTGGATCTGTGTTGCTTTAAATGTGGTCCCATAACCACTGGCATCAG
AGCTTGTTAAACCTTGAGGAACTTGTTAAGATAGCTGAGACATGGGACCCACACAAACACGGAATCAGGCTCTGCGG
CAAGGCCCGGGAATCTGCATTTTAAGGTTAGAAACCGTGATCCATCCCACCTCCTCTACGGTAATTTTGGACTACGC
GCTCCGACTTGAACTGAGGGACTCTGCTGGGCGCATATCGCCCAGCAACCTGACCTCAGAGCAGCGTGGGCGGCACG
GCTACCGCCGTTCTAGCCGTAAACTGTCTGTTACGTACTAGCCCTTCCAGTCGTCACAAACCAGCCAGGGCCCCATC
CGTGTGAGGACACCGCCGTGCCTCCAATCAGCCTCCTGGCCGGGCGGCTGAGCAGGCTGCCGGGGGGGTGGGGGGT
GGGGTTGGGACAGAGGCGGCTCAGCTTCGCCCCCTCGAGGCCAGGTCCCTCCGCAGGCTAGCCGGGTTGCAGTTTCC
CTTCTCCGCCTCCGAGCGCCTTTTTCTTCGTAGTCCCGCCCACCAAGGAAGCCAGTACAGCGCCTGCGCCTTCTACC
TTGCCCCGCCTCCTAGCTAATCGGAAGTTAGCCGATTTCCCATAGTGCCCCGCGAGTGGCGGGCATGATAGTAAATC
CGGTAGGCTCTCTGGCGGGTTTAAGTCGGCTTTGTTGCGGTTTCTCTTGTGCCAGGGCGCTGTAGGGAATTGGGGCC
TGGTCAGTGCTTTGTCTGCGGATGCAATGCGCGTTCTCCGGGGCGTATGGGCGTCCTGAATGCGCTGGGAAAGTCA
GGAGCGGATCTCTCGCGCGGGCTGTGGCAGTCCGACTGCCCTCTCCCTTTACCAAGCCTGCTTGCCTGCACCTTCGGA
GGCGGAAGGGTTCAGGACGCCTTGGGGTTAGAATGTAGACGCTGTTCTCCGCTTTCTGACCCCCCTGAAATGGTCAG
GACTGACTTAGCCCTGTGATTCCGACCTCGACCTTGCCAAGGGGATGATAGCTTTGAGACGAGGCCTTACTGCTTCA
GTACCCCTTGCCTTCCTTCCGGTCACCTTTCCCCTCCTCCCGTCCCTCCTCATTCTCGTACCTTGGAGCACCGGGTT
CGTTGTCCCCTGCGAAGTCGCCGCAAAGTCTCCTGCCTTCATCTAGCCATTGAGGCGAAGCCCAGGAGCTGGAGATA
CATGCTTTCCTTCACTCTCTGCCCTTGCTAGGGGGTTAGGGCTTTTGAGACTTCAGTTTTGCAAGCTCTTTCCCCTG
GATAGGACAGGATTTTAAATATCATTAGTGTTCTTGCCGAAGGTGTTAGGTGTCAGATATGTAGCATCTTGATATCT
TGCTTGGCATCTGTGTGCACGTAATTATGAATACAGGTACTTAAATGTTTAACACTGGTTATTTTCTTTTTATTTAT
ATGTAGTTTTGCGTATGTTCCAAAATGGTTTTCATCCAGCTTGAGTGGTTATCCAAAGAAGCCCATGACTTCATACG
TTCCATTTTCTAAAGAACAGCTGCCCATATTTAAAGCTCAGAACCCACCTAAGGAGTTTGGGTTATATACTCTTCTC
TGATGTACTAAAGATGCCACTAAGCAGTTAAATTGCAGACTTGATTTTCAGTATCAAGGCATCTGTTGAATGCAGAA
ACATAACCATTCTGTGTGATGGCCTGTAAAATAGATATAACATGGGCTTGTATGAAAGCCACCTGCCAATGCAGGAG
ACATAGGAGTCGCGGGTTCAATCCCTGGGTAGGGAAGATCCCCTAGAAAAGGGAATGGTGACCCGCTCCTTTATTCT
GGCCTGGAAAATTATGGACAGAGGAGCCTGGCAGGCCACAGTCCATGGATTTGCAGAATCAGACACGACTGAAGCGA
CCTAGCAGGCATGCATAAGGACATCAGTGTAAGCACAGCAGTAAGGTAATTTTACCAAATAAAAATGCTTTAAATGTA
ATTGAGAACTGGTGAAAGCTATTTTAAAAATAGCATGTAGAATGCAAAGTACTTAGGAAAGAGGATAAAAAAGCTGA
ATTTGGGGCCTTGTGGCCATTGGCCCAGAGGACCATTGACGAATCATTTTACCTCTTGCTTAGCTCCTGCTTCTCCC
ACTGCAAATTATTAATAAAGTTGCAGTGAAATAATTTATGTGGATGTGTTGCATAAACTTGAAAGCTGAATACAGGT
TATTGTTAATTTTAAGAGCTTTTTGACTGAAAGCCAGTTGAATTTCTGAAAGATTTCCAGTTAGGTTTGTTGACTCC
CTAGAAAGACTGGGTCCTTATTGGGGCTGTAGTGTAAAGATAGTGACCAAATTAGTAATTGCTGAGCTTTTCTTATA
ATTCCTAAAGCTTTTTCATATGCATTATATCACAGGGCACTTATGAAAATCATGTGAGCTGTAATAGTCACGTAAAG
AACTGGTTTAAGAGACATGCTTCAGTACTCACATCTTTTGAAATGTAGGAGTTGAAACTAACAAGTAGTTTGTTAAA
TCATTTATACCTTGTCATTCCAGTTAAGATGGGAAGGAAATGGAGAAAAATTATTTGGTTTTAGAATAATTTAGCTT
GTTTGCAAACAATATTTCTGTAATTTAGATACAGGTGGTGTTATATGAATCAAGACTATATTTTGTTGTTTAGTCAG
GTTTTATGAACTTGGTCATTCCTGAAAGACTTGAAAAAATGTTTTTGATTGAAATATGAAGTAGAAAACTTGTAGA
CACTGATTCCCCAATTGCTTTAACTTAGTAATCAATTCCTGAGGACCATTTTGGTGGTAAGTGGTACTATTCCTTAA
TTTAATCATTAGATAATAGACTTTAATAATGTTAGATAAAATATTAAATTATTTATTGTACTTAAATTAGTTGGTTA
AAGAAAAACTAAATAATTTTAAGTTGTGTGTGGTAAAATGTCTGTAAAAATACTTAATTTTAGAGCTAATGGATTAT
TCTTTCCTGAAAGTCTTTAGAAATTGATCCAGAGATGTAAAATGGTGATACCAATTTTTATTTCATTTCATAGATCC
AAAAAATTCAGAACTAATTAAAAAAATTGCCAAGCTATGGAGGGAACTTCCTGATTCAGAGAAAAAGGAAGCATAT
AAATTTTTAACATTGCTGACCAGTTACTTTGCAGGTAAGGACAACTGTCATGTCCTTTAAGGAAAAAGATGACCCAG

FIG. 6B

```
AGTTTTTTTTTTAACGTTTGTTATCTCAAAGGAATGTCATACTTTCTCATCCACATAAATGATGAGAATATGGATA
AATGGCAGTGGTGATGAAGCGTTGGTTTTTGAAGCAATTTGAAGTTGGAGGCCAGTTGCTAGACCTTCACCTTGGAT
AACACATTTGAAGAACACGTGATTTATAAGTGGGATTTCAGAGTGCATTTTCCACTTGGTGGTTCAGTCAGTTTGCT
GAAGTTACGCAGTTGTCCTTCCCCGTCAGGTGTGCTATGTTTAATTAGCCAGCAATAGTTTATCAACTTCTTATTTG
GATTTTTTTATACATATATGAAGATCCTTACAGGGCAGACTGGCAGGTATACAAGGAACAGATAAACAGAATTCAAG
AACAACTAACTCCAAGTCAAATCGTATCTTTGGAAAAAGAAATCATGCAGAAACGTTTAAAAAGAAAGCGTTAATA
AAAAGAGACTGAGTATGGTTGGCATAAAACTGAAATTTGGCAAAAAACTGAAATTTATATATCTATAAATACAGGT
TTGCTTTTTTTCCTTTGGCAAAAAACTGAAATTTATGTATCTATAAATACAGGTTTTTTCCCTTGTTTTGGTGACGT
GGTAGAGAATGACTTCAGTTAGGAAAAAATAGGATAGTTTCCTTCTGCCACTAGGACCACGTGCCTTTGAGTATGTT
GTAAACCGTTTTTGCTCCTTTTGGATGTGTCTGAGTTCGAGATACATAATTAGGACTGGTGTGAAAGCTGTAGGAAC
AGAGTTAGGAAACAGGAAGATCAGGAATAGCAAAAGTCTTGATTCTCTGTCATTTCTAGAGTACCTTACTGATTTGA
ATTGTTCTATAGGTGATGGTGAATTTGATTCTGAATATTGCTGAATGGACTGAATTCATTAACTTATCAATGTTTTA
AAAATACCTATTGTAGATAATAAAATTAAAGTGCCTTTAGGATGAAATTCAATTTTTCCTCATTAAAAATCCCACAT
GGTTCAAAATTAGTGGCTTCCAGTTTAAGGTATTAGTCCATATAAATTCTATTGTTTGACAGACTACATCTTTCCAT
ACTATTAGGTGTGAGGTGGTGAACTTGCTGATCCAGTATATATACCATAAAAAATGATCATCAGAGCAAAAGCTTAC
TTCTCTGAAAAGTAGATTCCAGCCTTTAGTATGAAGTGATGGAATCTCTCTTCCTGATCGCTGTGTCTTAAGCCCT
CCTAGCTCTTGGGTTGAGGACTCACCCAATTTCAAGTCAATGATAGTAATCGGAGACTGCTAATCCAATCAGTAAAA
GGAAGCCAGAAAAAATAGGGATGGTATTTGGAGGGTGGAAAACTAGGGTTTATTCTCTCTTGAGCTCTCCCTTGCTC
TTTAATGCACCCAACTAGTACTTTGAGTGGGGAGGACCAGAAATGAAGATTGAGCAGATATAAGGAGTTTCTTATTC
AGGTATTTCTGTTCCTTTCTCTGTTGTATTCCAGTTCAGTTCAGTTGCTCAGTTGTGTCTGACTCTTTGGTACCCCA
TGGACTGCAGCATGGCAGGCCTCCCTGTCCATTAGCAACTTCTGGAGGTTACTCAAACTCATGTCCATTGAGTTGGT
GATGCCATCCAACCATCTCATCCTCTGTCATCCCCTTCTCCTCCTACCTTCAATCAGGGTCTTTTCCAGTGAGTCAG
TTCTTCGTACCAGATGGCCAAAGTATTGGAGTTTCAGCTTCAGCATCAGTCCTTCCAGTGAATATTCAGGACTGATT
TCTTTTAGGATGGACTGGTTGAATCTTCTTGGAGTCCAAGGGGCTCTCAAGAGTCTTCTCCAACACCACAATTCAAG
ACATCAATTCTTGAGCGCTCAGCTTTGTTTATGATCCAACTCAACATCCATACATGACTACTGGAAAAACCATAGCC
TTGACTAGAGAGACCTTTGTTAGCAAAGTAATGTCTCTGGCTTTTTAATATGCTGTCTAGGTTGGTCATAACTTTCC
TTCCAAGGAGCAAGCATCTTTTAATTTCATGGCTGCAATCACCATCTGCAGTGATTTTGGAGCCCAAAAAAATAAAG
TCTGACACTGTTTCCACTGTTTCCCCATCTATTTCCCATGAAGTGATGGGACCATATGCCATGATCTGTTTTCTGAA
TGTTGAGTTTTAAGTCAACTTTTTCACTCTCCTCTTTCACTTTCCTCAAGAGGCTCTTTAGTTCTTTACCTTCTGCC
ATAAGGGTGGTCTCATTGGCATATCTGAGGTTATTGATATTTCTCCCAGCAGTCTTGATTCCAGCTTGTGCTTCATC
CAGCCCAGCGTTTCTCTTGCATGTGTGCTATACATATTGTAGTTGTCCAGTAGGGGTTGGATGTTCTTTTTTTTTCC
CTCTTCAGTCTTTGTTCTCTTTACTTTCGGATTTTCGAGGATTTTTTTTTTTTTAGCCATGCTGTGTGGCTTTTG
GGATCTTAGTCCCTTGACCAGGGATTGAATGTGTGCCCCCTGCAGTGGAAGGTTGGAGTCCTAACCACTGGACTGCC
AGGGAATTCCCTTTATCTCCAGCACTTCTTTTGGGTTCTTTCTTATGATTTCCCTCTGCTTACAATGCCTGTTCTTG
CAGGCTGTCTAGAATCCTTACCATATTAATCACAGTTGTTTTAAAATCCTGGTCTGATAATTTTGTATCCCTGCCAG
TTCTGATGCTTGTTTTGTTTCTTTATGTTAGGCTTTTTGTCTTTTAGTATGCTTTGGGATTTTTTTTCTTGATAGTT
AGACATATGATGTGCTGGGTAAAAGGAACTGCTGTATATGGGCCTTCGTAATGTGGTAAGGCATGGGGCAGGGGAAG
CATTCTACAATCTTATGATTAGGTCTTGGTCCTTTAATAAGGGCTTCCTTGGAGACTCATTGGTAAAGAATACACCT
GCCAATGCAGAAGACCAGTCGGGAAGATCCCCTGGACAAGGAAACGGCTGCCCACTCTAGTATTCTTGCCTGGGAAA
TCCCGTAGACAGAGGAGCCTGGTGGGCTACAGTCCCTGGGGTTGCAAAAGAGTCAGATATGAGTTAGCAGTTAAAAC
ACAAAAAACCCTTTAATGAGCCTGTAGCTTTGTGCTTAGGTGGTACAGGATGGCTAAAGTGAGCTGCAGTCTAGTAT
TTCCTTTCATTGAGGTCTTTTAGGCTCTTGATAGTATACCAGCAGGTTAGGTTCTTAATGTTTATTTGTGTGTTTAT
TTTTTATTTGACTGCACCAGATCATTAGTTGCAACACGTGGGATCTAGTGTCCCAGCCATAGATTGAATCCCAACCC
CCTGCATTGGGAGCACAGTCTTAACCGGTAAACCACCAGGGAAGTCCCAGCAGATTAGGTTCTGATTAACTAGTTTC
CCTTGAGGGCAGGCCTTGTTAAGAATAATAAAGTACTCTGGCATTTCGAAATGATTCCTTTTCTTCCTGCTGAAAGC
AAGAGGGGTTTTTTTTTCCCTTGATATTTACTGTGGGAATCTGGTCAAGTTCCTGGAGAAAAACCTCACAGTATTAT
GAGGCTTTCCTATGAGTGGTGGTAGCTCTCAGAGCTGTCCACATGGAGCTTCCAGCAGTTAGTCAGCTGTGGTTCAG
TTTCCTCCACACCACTGGTTTCCATTCCTCTATCTGTTCCAGTAAGTCTCGACTCCCTGTGTTCACCTGTCTGTGTC
TGTCTCCAATCTTGAGAGCAGCACTTCACCCTGTGTCCCCTCTTCAGTGGATCCAAGAGAGTTGATTTTGCAGTCTG
ATCAGCTTTATACTTATTGGATGGAGTGCTGACTTCCAAACTCCTTACATGTAGAACCAGAAACTTAGAAGTCTGAG
TGACTTTTCCGTAAGACTTCCATTTGCTCTCCCTGTTGGAATTTTTCTTCCCATTAGATTCCCAGTTCCAGCTACTT
GCAGTTTAGGTGAGAGGTGGGGGCCAGGCAGTTGCAAGTGAAGCACCTGGAAGAAAATAGCTAGCAGTGGCTCTAGAA
ACAGAAGGGGAGATGCCTCCTCTCCCGAGGGGCTCAGGGCTGAGAGAGTGACCTCCATATGTAAATCAGAGGAGCCC
TGCTTATGAATGAAAGTTGGGTTCGTTATTGACTGTAAACCAAATTGCCATTAAAACCCCCATCGTTTTATAAATTT
```

FIG. 6B CONTINUED

CTATCTAAGTTCAGAAACTCAGTAGGTTAGGATGAGGCAGTGGCCTTCATTAGACAATGCAGCAAATGCGCCAATGT
TCTTGAGTTGTCAAGTGGGAGTACGTAGTGCTTTGTCCAAGGAGAAGTGGTGCCTTACAAGGATAAAACGGGTTTTT
TTTTAATGTTTAAAAAGATTTTGTACATCCTGCTCATTTATTCAGTTCATGGAGACCATAAACATAATATGTAAAGG
AAATGTTTCTGTATGAAAAGTAACTTATAAAATCTATTAGGATTTTCAAAACAGTACTAATCAAAAATTCTGATCCC
AAGAGGGAACAATCGCATACTCATAATGTTCATTTTAAAGAATATTCTGTAATTCATGGTAGTGAATGAAGTTTCTC
TAGGTAAATTTAAGTATCATAGAGTTTAAAACTTTATCTCACCTTTCATTTTTTTTACTCACGAGTTAACAATGCTT
GGAAAACCGAAAAGACCTCGCTCAGCTTATAACATTTTTATAGCTGAACGTTTTCAGGAAGCTAGGGATGGCACATC
ACAGCTAAAACAAAACTCTGTATGTTTTAGAAATGTTTACTCTAATTTTTAAAATAATATAGACAGGAAACTTTAGG
GGTGCAACCTGTCAAGTGGTGAAAAAAGTGGTAAATTACTATAAAGAAATAGTATATATAAATAAGACCTAAAAAT
CCTTTTTCTTACCACATAAAATGTTTAAAATTTGAATGTGTTATATATACATATTCAGCCATGTATATACATAGTCA
ACTTTTTAAATTAAAAAACAAAATTTTCACCTTTATAGGAGTGTTCAAGTTCTGGAGACTTTTCTTATCCAGCACTT
CTGAATGGTTTTACAATCACTGGGAAAGAATGAGAGAGAGAGGTATAATGTTTCATACTGGGATTTGAGTGTGGCTT
CATGTTACGCCCTTTAAACATTTTTGGTTATCCCATGGGAATGTATTATATTACACATATGAATGGTATCTATGTCT
GCAGAAAGAAGAAAACAGCTTGTCATTCTTGCTGTGGCTTAGTCTTTCCTTTATTTCCTTTTTAGAGGCTCCAAATT
GTTAGTTGTACTATTCCTCTTTTAATATGCCATGGTAAGAAAAGTTGTCTGCTCGGATTCCTAATTCTTGTCAGTGT
GAGATGGAGGTTTTTGCCACTCTGATTCTTTGGGTTATTTAGATCTGTAGTTCATTTCACAGATCCTGTTGGACATA
TGATTAAATGATGTGTATATGTAACGTATTTTTCTGGCTATATATGATTTCACTGACTACTTCCCTTGGGATTTTAT
TTTCCTTTTGAAAAGTAGTACCATTTTATTTAGTGTTGTAGGACATCGTAGGTTACTTCTGAAAAACAAAAAGGGGA
TCTTCTCGGACCAGGGATTGAACCCATGTCTCCTGCATTGGCAGGTGGATTCTTAGCACTGAGCCACCAGGGAAGCC
CTGGATTTTAAATTTAGTTTCCATGGCCCTACATTACTAAAACAGCAAGCCTGTTTATTTTTTTAGTTGGAATTTGC
TCAGTCACTAACTAACTTTGGATTTCATTTTATTAGTATAAGAAGGTTTTGTGTTAGAGAATCCTTCTGAATCAGTA
GTTCTCAACTCTGACTGCATCTTGGAATCACCTCAGAAGCTTCCTGGCTGGCCTTTATCTCTGAAATTAAAATTAAT
TTAATTCTATCATTTTTATTCATGTAAAAAAGTGCATTCTCATAGTTTTAAAGAATCAAATGAGGCTTGTTATGAAA
GACACAAGTTTCCCTGTGCCGTCATGTTCCTCACTCCAGAAGCAAATGCATTCTGTTTTAGTTGATTCTTGTAGTAT
TTACCCCATGTCTCTAAGTAATGTTCCTCCATTGTCACGTCCTGATTTTCTAAAATTCTAAGCGTTACCTATATT
TTAGGCATTCCCTCTCACTGTGTAAGGTGAGCGTTAACTCTGTCTCATCGCACTGTTCACTCTTCTGTCAGTCTGCC
TCCCAATATAGTTACATAATTTGGGTTAGATCAGTATTGAGTACTTAATACTATGATGTGTGCATGCTAATTTGCTT
TAGTCATATCCGACTCTTTGTGACCCTGTGGACTGTAGCCTTCCAGGCTCCTCTGTCCATGGGATTCTAGAGACAAG
AATACTGGAGTGGGTTGCCATGCCCTCCTCCAGGGGATCTTCCTGACCCAGGGATCAAACCAGTGTCTCTTAAATCT
CCTGCATTGGCAGGTGGATTCTTTACCACTAACGCCATCTGGGAAGCTCAGTGGCTCAGCCAGTAAAGAATCTGCCT
GGAGAGGAGAGCCGGGTTTGATCCCTGGGTCAGAAAGAATCCCCTGGGGAAAGCAATGGCTACCTACCCCAGTATTC
TTGCCTGGAGAGTGCCAGGGACAGAGGAGCCTGGAAGGCTATGGTCCATCGGGTTGCAGAGTTGGACGCAACTAAGC
GACTAACGCTTTCTGCACTTAGAGCGTGGAATTAGCTCTGCTTTTCTGCTCCCCAAATGCTGTGTTGGTAGTGTCCT
TTCCTATTGTCTTTGTCGCTGTGGATTTTATGCCTTTAGAAATTTTAGTTGTTTAATTAAAAAAAATAAATCACAGA
AATGAATTGCTTACAGTTCTGAAGGTTAAAAGTCCACGATCAAGGCCACATCCTGGTGAGGGCCCTCTTCTGCTTCA
TAGCTGGCACCTTCTCTCTCTGTGTCCTCACATGGTGTGAGTGCTCATTTAATGTGATTTTAGATAGCACCAGAAGT
AAATACCTTCCCATCCCTTTAATTTGTTTTCCATGAATTAGTTTTTTAGGTGAAAGATTGTTTATGCATGCAGCTTC
ATAAATTATTGTTTAACACACTGAATATGAACTTGTGGATTAAATATAAGCAAAAAGATACGTTATGAAAGAACTA
AAAGCATGAAAGCAATTCTTTCCAAAGCTAAGAGAGCAGTTATTTAATGAGTAACCATCCCTGAATATACTAGATGT
ATTTATAAAGGGAAGCTTAAAATACTCAAAATAGGCTCAGATACCATCTGGGTACCTCACTTTTGTTGATAGGAAA
ACAAAATTCAGTGAAAGTTCTGGTCAGAATAGTGAAGTTAATAGTTCTAACTCTACTTCTTAAAATCACTGATGATA
TCCTCCTGCCTTTAATAGGCACTTTTCATCCCCTCTCCCTCACATTCTCCGCCTCTCTCTCCTTCTTCTCTGCT
CCTCATTCTCCACCCGCCCATTTTCCTCTTCAGTCTTTGCTCTCCGGTAGCAGCACCACAGGCTGTGTGAGGTGTAC
TCACTGTCTCTCTGCCTCTCCTCCAAATATGGGATTCCTGCATCCCTTTAATTTTATAGATTAAAGCTCCCAAGCCT
AAGGGAGGTCATAGAACTTTTTCCGGGTCACATAGTTAAGCTCAGCTGTGTAGGAGGAGAATCGGCGCTGTGTTGCT
CCTGTGGTGACAACTGAAACACAGTGCACAGACATGAGAGGTCAGAGAGCACTTAAGCCACAGAGGAGACAAAACAG
TATTTGAGGCTAGTCTGTGACAGAGTAGCTTATATTTGAATATTAATACTTTGAATTCAAAAAGATAAATATCTGC
ACAAACAAAGGAACCATCAACAAAATGAAAAGTAATCCTACCAAATGGGAGAAAATAATTTGCAAATAATTTAGAGA
ACTCATATGACTCATTCCCCCACCCCCGAAGAAAAAAATCTGATTAAAAAATGGGCAAAGGATCCGAATAGATATTT
TCCCAAAGAAGACTTAGAGATGGCTAACAAGTATATGAAAAGGTGCTCAACATCATTGTCAGGGAAATGTAAAGCAA
AACTACAATGAAGTACTCCCTCATATTCTTAGAATGGCTCTTATAAAAAACAAGTACTACTGAAGCTGCAGTAGAA
GGGGAACCCTTGTGCTGAAACAGTAACTCAGAACACATAGACACGAGCAACACGTTGGTGACTGCGCGAGTTGCTGG
GTGGGGTGGGAGGGTGGAATGGGCAAAGGTGGTCGAAGGGCACAGACTTCACAAGCGCTGCACTGCACACCTGAATG
TATTGTTACATGTTAGTTACAGCTCAGAGTTTTGAGGAGTCTTTGCCTGTGATTCTTGATATCTGAGTGTGTGTGGT

FIG. 6B CONTINUED

```
TGGAATGAATAATAAAACAGCATCTTTCTTCAATCACTGAAGTCCCTGTATCTGGTACTTAAGTGTATATTGTTTTA
CAGGTAAAGCTGAAAGCTATAAATGAAAACTGGAAAAATCTCTCTAATTCTCAAAAGCAAGAAGTAGTATGGTTTT
AGTCCCAAGTGCCTAGTTAGAGTATCTGTGAGAATATATCAGGGCAAGGCTTGATTCATGTGAAAACAACTTTATAT
TACACAGTGTTTTAAAATCATTGTCATATTCTTGGAACCAGTTTGGCTTTTTTCTTTTGGTAGTTTTTGATTCCATA
TCAAACGGGTATTTAAAACAGTGTCCCTCGTAACTTAGTGTCATCATATCCAGTAATGATCACACCCTGCCCCTGTT
GCTTTTCCACACTCCAAACCCTGAAATTGTAGCGACTTCATGAATACTTAAAAACCTTTATCTCTTATCTGTTTCTC
ATCTAATTTTTATCTCACAAGAATATTTCTTTCCAGCCCCCTTTAACATATAGAATAGTAAAATAATTTCTAGAAT
ATTTTTGGAGAGCATCCCAGAAATTAACTGCAAAGATTCCTCTAAAGAAATCATTTTAACAATTACACTCTTTCTCA
GGTATATATTCAGGTTGGTAAAGATGATAAAATTCGTTATTATAACGAAATGAAATCTTGGGAGGAACAAATGATGG
AAGTTGGACGAGAAGATCTTATACGTCGCTCAATTAAATACCCAGCAAAAAATGACCCTGAGAAGTTTTAAAATAGA
AGATTGAGTTATGTTCATAATGGATAGACATAAGAAACCAACTAGGTCTCAATACCGGAAGCTGTTGTAAAATTAGA
ATGGATAAAGTTGGTGAACATTTATATTTAATTCCTTTTCTGTAGCCCATGGACTTCTGCCAGCCAATTCAATACAT
TTTGTATTGGTGTCTTGCTTTTTGAAAACCCAAACAGATAAGACTTCATGTGGAATTTATTTTGTGTTTAGGAACTAC
TGAGCATCAAAATAATCCATGAAATGTAGCAGTGAATCATTTTACCTTTGATAAAGGTAAATCAGACTGTGAAGTTT
TTTTATACTTGGTGATTATGGAAAAAATATTCTTGTTTCCTTATATTATGGAAGCAGGAGTTTCCTATTCATAAGTA
TCTCAAAGTTTGTAGAAGCCATAGTGTTCTATGATATAACTGCATTTTTAAAAGAGCATCCAGAACTCATGCTGGTA
AATTCCAAATCCTGGGTATAATTCATATTATAATCAGACTTGATGGTTGTACATGTGAGGAATTTCTGGTATCAGTT
GCAGCTTTTATAAAAGGTATAGATTTATAAACCTTTTCCTCATTATCTTTTTCCTAAATTAAAAACTAAAAATTAT
GTACCAAATCTATGCATATTGTTTTATATTGCATAGAATAAAAATTATGTGTTTCCTAATTATGTTTTAAGGTGAAA
CATTCATTTTATAGCTTTCTGGGATTTTTGTTTGTTTTTTTAAACAAAGTAGGAGTTTGTATACTGAATTATTTTTT
CTCTTATGTAAATATATTTATCCAGAAAGTAGAGAACTTATTTGGTGTAAGTTTTAAAATGAGAGATCTAAAAAAAT
CATGTCTCCAAAGTCTCTCAAATTGGAACCTATAATTTTTAAACATTTGCATAACATATAAAAGCCTGTATAATAAT
TAATAGCCAGTTCTAGCCTGATGCCCACATCCAGCCCACTGCCTGCTTTTCTTGGCCTTGTCAACTAAGAATTGTTC
ACAGTTTTAAATAGTTAAAAAAAACTAAGCATACTTCAAGACACATGAAAATTAATATGAAATTCAGTGTCCATAAA
AAAATGTTTTATTGGAACACAGCCACACTCATCGATTATGGCTGTTTTTGTACAATAGTGCAGTTGACTTGGTTGCT
ACAGAGAGGTGCAGCCTGCAAAGACTGACCCGTATAGTGTGGAATGAGATGCTCTTAAGTTACTTGCTGTGGCTCAG
TAAAATACATCTTAACAGTTTTCCAGTTAGCATTTAAACCTTACCCCTTCTAGCATTTGATTATCTTCTTAACAAGA
GTCAAAGGTTTTTCAAAATCCACACCACCTTTTTGAGCAAAATATTCAACTGTCATCATCAGTTCACATGAATTTAT
AACTCAAAATTTATATATTTACTTTGTATTTTGCAAAAATATGCAAAAAAAAATAAAAGTGTATATTCTACATCTCC
AGAAAGAAGATTTTTGAAGTTTGTGGATAGAAAATAAGTAAAAGAATCACTAAAAAAATGACTTGTTACGTACTGAAC
TTGGCAAAGGTCAGGACTGTAGGGAAAACTACAACTTAAGAGGACTAGCCTAAGATTTAAATATATGGAGCTGTTTG
AAGTTTTCAGGCGGCTTTGCTCTCTGAATGGTAATGCAGGACACAGCCTGCCAGTATGTAAATGACCCTTGGTCTGA
GGCTAGAGTGTTCTGGGGAAGAAGAGAGGGAAGAAAAGGACACGTGCTAGTGTCTCTCCCAAGCTTTCTCAGTTAGG
TTTCCAGGAGAGAATTAAGCCCTAATTCCCTGGGGCATCTAGAATGGTACCAATTTTGTACCAGCCTTAGGAGAATG
GAGAAAATAATCACTCAAATAATTTACTGTGTTCTGTGCTTCAGATGAGCCCAGGGAGCACATGGGAGTCGATGTTT
ATAATATTATAGAATGGGTGAGGAAGAGAAATGAATTATAAACTCCTGTAGCACAAATGTATAAAACACATCTGCGT
ACTTACCTTCTGAGCTCTAGGCATTTAGCTGCCTGTACTGTTTTACACCGAACACATTCAAATATCCAGTGTCTACG
TTCTCATGTATATACTTAATATAGGGAGGACAGGTATGAAACAGTGAAAGGAGCTGTAGCAAAACCGTTTTGTTTCT
AAAAGGGTGTCATTGTTAATACTTTAAATATTAGGATAATCTGATTTCACACCTTTCTTAATAAACTTCAGTACATG
GCATACCATGTATTAAATGCCATCCATTTGTATATACAAATACTCTGTTATGAAGAATGAGAGCGTATATCAATAAC
CAGTGGCTAGGTGTGTAACCGGTGGCCATTCTTATATTGGCTGAACAAGAAACTAAAAGCTAAAGAATTGTGACCAG
GGAAAAGATGCTTAAGTGAAAACAGCGTTTATGCTGTCTGAGCAGTCAGTCACAGAGACGCTTATGTTCACTAGAGT
ACCAGTATTAGATTTTATAAAACAATTGACAAGGGTGTGTAATTATTTTCTGATGTTTAAGGTATATGTGCAGAT
TCAGCCTACTGTAATAATGTAATTTTGCCATTGCTTTTGGCTAACTCCTTTTTTGGAAATGCCCTTTTTTTTTTTTT
AATGTATATGCTTTTTTAAATAGTTGGCCATGAATGTGTATATTTACATTTCTGAATTAAAATGCAGTTAAAGTAAC
TGGCAAGTTTTATTGATATTTGTGACATTTACTGTACCTGAAATTAATCACCACCAGATTGTCCGAAAGCAGCAGGA
ACTTCTTATATAGGTAAGTAACTAATTTCCATTATTTCTCTTAATTTTACCAATCTTTTTACTGTAAGACTACTCCA
ACAACAACAACAAAAATACTCTTTTCTTTCCTTTTCTCTCCTCACAGCCACTATTCCTCTTCCTTTTCAAAGCACCA
AGCTCTTACAGACAAATTTGAAAATGTTACAAGTGCAGATAATATGTTTTGAAATTTTAAAGCAGTAATACTCTTTT
AAATTGAACTTTGGGGAAGAATAAGAAATGAACGTATTTATTATTATTTTCAATTTGTAAAATTTTCCAAATAGTAA
AACTGTACAAAGTTAGTATCATCATTCTCTCACATTGTTCACAAATAAAATATTTTTGGTAATCATTGATTATATTT
GATGGCAAATACATAAAACATGAAACCATCTTCTAGCACATTAAAAATACTTTAAAAAATTTTTACTGGCTAAAAAA
CTACATACTTAAAATTGACTGTAAACAAAATTTTAAATAGGCTAAACATTTAAAAATTACCCTAATGGCAGAAAGTA
AAGAAGAACTAAAGAGCCTCTTGAAGGTGAGAGAGGAGAGTGAAAAAGCTGGCTTGAAACTCAACATTCAAAAAACT
AAGGTAATTGCATCTGTTCCCATCACTTTATGGC
```

FIG. 6B CONTINUED

POLYMORPHISMS IN MITOCHONDRIAL TRANSCRIPTION FACTOR A ("TFAM") GENE AND THEIR ASSOCIATIONS WITH MEASURES OF MARBLING AND SUBCUTANEOUS FAT DEPTH IN BEEF CATTLE

INCORPORATION BY REFERENCE

This application claims benefit of U.S. provisional patent application Ser. No. 60/685,213 filed May 27, 2005.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to the identification of single nucleotide polymorphisms (SNPs) within the bovine genes encoding mitochondrial transcription factor A ("TFAM") and their associations with economically relevant traits in beef production. The invention further relates to methods and systems, including network-based processes, to manage the SNP data and other data relating to specific animals and herds of animals, veterinarian care, diagnostic and quality control data and management of livestock which, based on genotyping, have predictable meat quality traits, husbandry conditions, animal welfare, food safety information, audit of existing processes and data from field locations.

BACKGROUND OF THE INVENTION

Significant improvements in animal performance, efficiency and carcass and meat quality have been made over the years through the application of standard animal breeding and selection techniques. However, such classical animal breeding techniques require several years of genetic evaluation of performance records on individual animals and their relatives and are therefore very expensive. Other efforts have been made to improve productivity and quality through the application of such management practices as the use of feed additives, animal hormonal implants and chemotherapeutics. However, there is significant political and regulatory resistance to the introduction and use of such methodologies. Such methodologies are also non-inheritable and need to be applied differently in every production system.

There is a need for methods that allow relatively easy and more efficient selection and breeding of farm animals with an advantage for an inheritable trait of circulating leptin levels, feed intake, growth rate, body weight, carcass merit and carcass composition. The economic significance of the use of genetic markers that are associated with specific economically important traits (especially traits with low heritability) in livestock through marker-assisted selection cannot therefore be over-emphasized.

The physiological regulation of intake, growth and energy partitioning in animals is under the control of multiple genes, which may be important candidates for unraveling the genetic variation in economically relevant traits (ERT) in beef production. Polymorphisms in these candidate genes that show association with specific ERT are useful quantitative trait nucleotides for marker-assisted selection Mitochondrial transcription factor A ("TFAM"), a member of a high mobility group protein family and the first-identified mitochondrial transcription factor (Fisher and Clayton, Mol Cell Biol. 1988; 8:3496-509), is essential for maintenance and biogenesis of mitochondrial DNA (mtDNA). First, TFAM plays a histone-like role in mitochondria, as it is tightly associated with mtDNA as a main component of the nucleoid (Kanki et al. Mol Cell Biol. 2004; 24:9823-34). Evidence has shown that one molecule of mtDNA is packed with ~900 molecules of TFAM on average (Alam et al. Nucleic Acids Res. 2003; 31:1640-5), which makes mtDNA no longer naked. Second, TFAM regulates mtDNA copy number in mammals. Investigation using a combination of mice with TFAM overexpression and TFAM knockout demonstrated that mtDNA copy number is directly proportional to the total TFAM protein level in mouse embryos (Ekstrand et al. Hum Mol Genet. 2004; 13:935-44). RNA interference of the endogenous TFAM expression in HeLa cells also indicated that the mtDNA amount is correlated in parallel with the amount of TFAM (Kanki et al. Ann N Y Acad Sci. 2004; 1011:61-8). Third, TFAM stimulates transcription of mtDNA. The TFAM protein possesses two tandem high mobility group domains, which makes TFAM bind, unwind and bend DNA without sequence specificity and thus facilitate transcription initiation of mtDNA (Gaspari et al. 2004; 1659:148-52). Evidence has shown that import of wt-TFAM into liver mitochondria from hypothyroid rats increased RNA synthesis significantly up to 4-fold (Garstka et al. Nucleic Acids Res. 2003; 31:5039-47).

It has been known for many years that adipose tissue plays a central rule in regulation and manipulation of energy metabolisms through the storage and turnover of triglycerides and through the secretion of factors that affect satiety and fuel utilization. However, many key aspects of adipogenesis are accompanied by stimulation of mitochondrial biogenesis (Wilson-Fritch et al. Mol Cell Biol. 2003; 23:1085-94). For example, the major site of fatty acid β-oxidation occurs in mitochondria (Reichert and Neupert, Trends Genet. 2004; 20:555-62), which may provide key intermediates for the synthesis of triglycerides via the action of pyruvate carboxylase (Owen et al. J Biol Chem. 2002; 277:30409-12). In addition, a relatively large mitochondrial mass are needed to generate acetyl-CoA for fatty acid activation prior to esterification into triglycerides. All these studies demonstrated the essential role and function of mitochondria in lipid metabolism.

To further explore the mechanism of mitochondria involved in adipogenesis, Wilson-Fritch and colleagues (Wilson-Fritch et al. Mol Cell Biol. 2003; 23:1085-94 and Wilson-Fritch et al. J Clin Invest. 2004; 114:1281-9) studied the 3T3-L1 cell (representative of white adipocytes) differentiation by using both proteomic and genomic approaches. Proteomic analysis revealed a 20- to 30-fold increase in the concentration of numerous mitochondrial proteins, while genomic analysis with gene expression profiling using Affymetrix GeneChips detected a statistically significant increase in the expression of many nucleus-encoded mitochondrial genes during adipogenesis. In particular, the authors found a profound decrease of approximately 50% in the levels of transcripts for nuclear-encoded mitochondrial genes accompanying the onset of obesity (Wilson-Fritch et al. J Clin Invest. 2004; 114:1281-9).

It remains advantageous to provide further SNPs that may more accurately predict the meat quality phenotype of an animal and also a business method that provides for increased production efficiencies in livestock cattle, as well as providing access to various records of the animals and allows comparisons with expected or desired goals with regard to the quality and quantity of animals produced.

Citation or identification of any document in this application is not an admission that such document is available as prior art to the present invention.

SUMMARY OF THE INVENTION

The present invention relates to the identification of single nucleotide polymorphisms (SNPs) within the bovine genes encoding mitochondrial transcription factor A ("TFAM") and their associations with economically relevant traits in beef production.

The invention encompasses a method for sub-grouping animals according to genotype wherein the animals of each sub-group have a similar polymorphism in a TFAM gene which may comprise determining the genotype of each animal to be sub-grouped by determining the presence of a single nucleotide polymorphism in the TFAM gene, and segregating individual animals into sub-groups wherein each animal in a sub-group has a similar polymorphism in the TFAM gene.

The invention also encompasses a method for sub-grouping animals according to genotype wherein the animals of each sub-group have a similar genotype in the TFAM gene which may comprise determining the genotype of each animal to be sub-grouped by determining the presence of a single nucleotide polymorphism(s) of interest in the TFAM gene, and segregating individual animals into sub-groups depending on whether the animals have, or do not have, the single nucleotide polymorphism(s) of interest in the TFAM gene.

The single nucleotide polymorphism(s) of interest may be selected from the group consisting of an A to C substitution at the −1220 nucleotide position in the promoter of the TFAM gene, a T to C substitution at position −1212 in the promoter of the TFAM gene and a T to C substitution at position −995 in the promoter of the TFAM gene.

The invention further relates to a method for sub-grouping animals according to genotype wherein the animals of each sub-group have a similar genotype in the TFAM gene which may comprise determining the genotype of each animal to be sub-grouped by determining the presence of any one of the above SNPs, and segregating individual animals into sub-groups depending on whether the animals have, or do not have, any one of the above SNPs in the TFAM gene.

The invention also relates to method for identifying an animal having a desirable phenotype as compared to the general population of animals of that species, which may comprise determining the presence of a single nucleotide polymorphism in the TFAM gene of the animal, wherein the presence of the SNP is indicative of a desirable phenotype.

In an advantageous embodiment, the animal may be a bovine. In another advantageous embodiment, the TFAM gene may be a bovine TFAM gene.

The invention also encompasses computer-assisted methods and systems for improving the production efficiency for livestock having marketable tender meat using multiple data, and in particular the genotype of the animals as it relates to TFAM SNPs. Methods of the invention encompass obtaining a genetic sample from each animal in a herd of livestock, determining the genotype of each animal with respect to specific quality traits as defined by a panel of at least two single polynucleotide polymorphisms (SNPs), grouping animals with like genotypes, and optionally, further sub-grouping animals based on like phenotypes. Methods of the invention may also encompass obtaining and maintaining data relating to the animals or to herds, their husbandry conditions, health and veterinary care and condition, genetic history or parentage, and providing this data to others through systems that are web-based, contained in a database, or attached to the animal itself such as by an implanted microchip. An advantageous aspect of the present invention, therefore, is directed to a computer system and computer-assisted methods for tracking quality traits for livestock possessing specific genetic predispositions.

The present invention advantageously encompasses computer-assisted methods and systems for acquiring genetic data, particularly genetic data as defined by the absence or presence of a SNP within the TFAM gene related to meat quality traits of the breed of animal and associating those data with other data about the animal or its herd, and maintaining those data in ways that are accessible. Another aspect of the invention encompasses a computer-assisted method for predicting which livestock animals possess a biological difference in meat quality, and which may include the steps of using a computer system, e.g., a programmed computer comprising a processor, a data storage system, an input device and an output device, the steps of: (a) inputting into the programmed computer through the input device data that includes a genotype of an animal as it relates to any one of the TFAM SNPs described herein, (b) correlating meat quality predicted by the TFAM genotype using the processor and the data storage system and (c) outputting to the output device the meat quality correlated to the TFAM genotype, thereby predicting which livestock animals possess a particular meat quality.

Yet another aspect of the invention relates to a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals, wherein a physical characteristic intake, growth or carcass merit in beef cattle and the genotype is a TFAM genotype.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which:

FIG. 2 provides a nucleotide sequence of the upstream region of the bovine TFAM gene (SEQ ID NO: 1). This sequence corresponds to the 5' flanking region and exon 1.

Coding sequence is shadowed. The putative transcription site was numbered as +1. Consensus sequences for potential SP1, NRF1 and transcription repressor are shown by arrows. Many potential mCpG loci are underlined. An extra AUG codon upstream from normal translation site is bold and marked. Both C/A and C/T substitutions are marked by arrows and numbers.

Figure 3:

FIG. 3 provides a demonstration of a C/A and a C/T SNP in the bovine TFAM promoter region. Left: a homozygote with CC and CC (SEQ ID NO. 23); Right: a homozygote with AA and TT at two positions apart by 9 bp inclusive (SEQ ID NO. 24).

Figure 4:
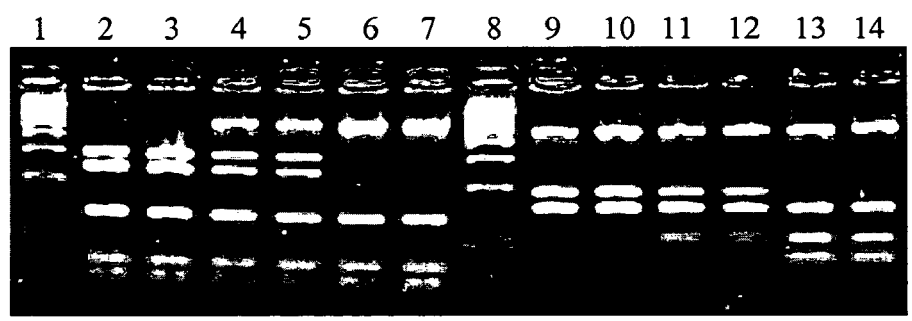

FIG. 4 provides PCR-RFLP genotyping of two SNPs in the bovine TFAM promoter. Lanes 1 and 8: 100 bp ladders. Lanes 2-7: a 801 bp fragment was digested with restriction enzyme DpnII. Lanes 2 and 3, TT animals (55+68+135+241+302 bp); lanes 4 and 5, CT animals (55+68+135+241+302+543 bp); and lanes 6 and 7, CC animals (55+68+135+543 bp). Lanes 9-14: a 801 bp fragment was digested with restriction enzyme HaeIII. Lanes 9 and 10, AA animals (152+187+462 bp); lanes 11 and 12, CA animals (83+104+152+187+462 bp); and lanes 13 and 14, CC animals (83+104+152+462 bp).

FIG. 5 identifies genetic polymorphisms in the bovine TFAM, TFB1M and TFB2M genes. A. A third mutation of C/T substitution in TFAM promoter region (SEQ ID NOS. 25 & 26). B. Two mutations detected in the bovine TFB1M gene using DNA pools (SEQ ID NOS. 27 & 28). C. Five mutations developed in the bovine TFB2M gene using DNA pools.

FIG. 6A provides a cattle TFAM cDNA sequence (2259 bp) (SEQ ID NO: 2).

FIG. 6B provides a cattle TFAM genomic DNA sequence (16666 bp) (SEQ ID NO: 3). Exons are shaded, as well as mutation sites. See, e.g., GenBank Accession Nos. AAFC02110692 and AAFC02019444.

Figure 7:
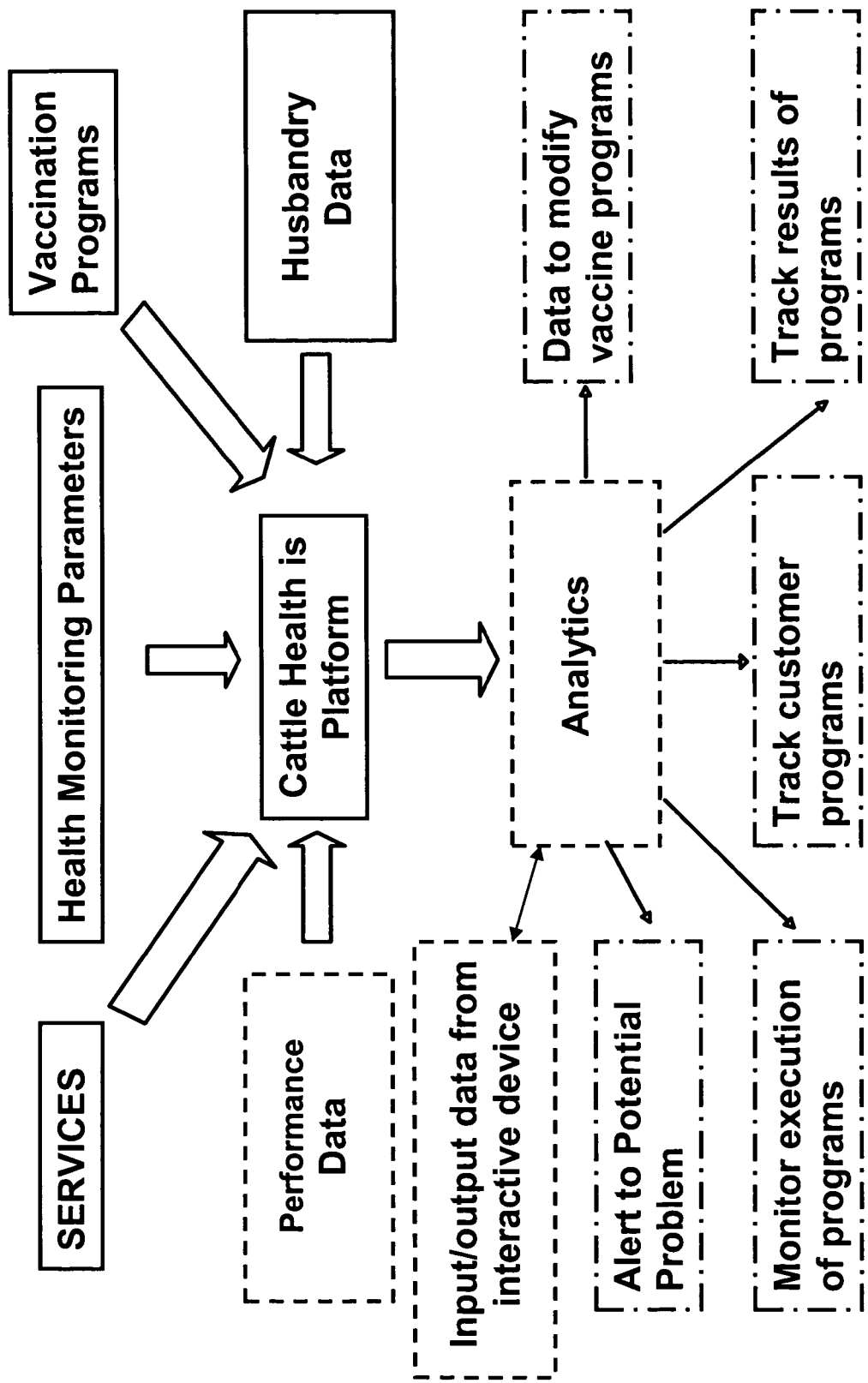

FIG. 7 illustrates a flowchart of the input of data and the output of results from the analysis and correlation of the data pertaining to the breeding, veterinarian histories and performance requirements of a group of animals such as from a herd of cows and the interactive flow of data from the computer-assisted device to a body of students learning the use of the method of the invention.

Figure 8:
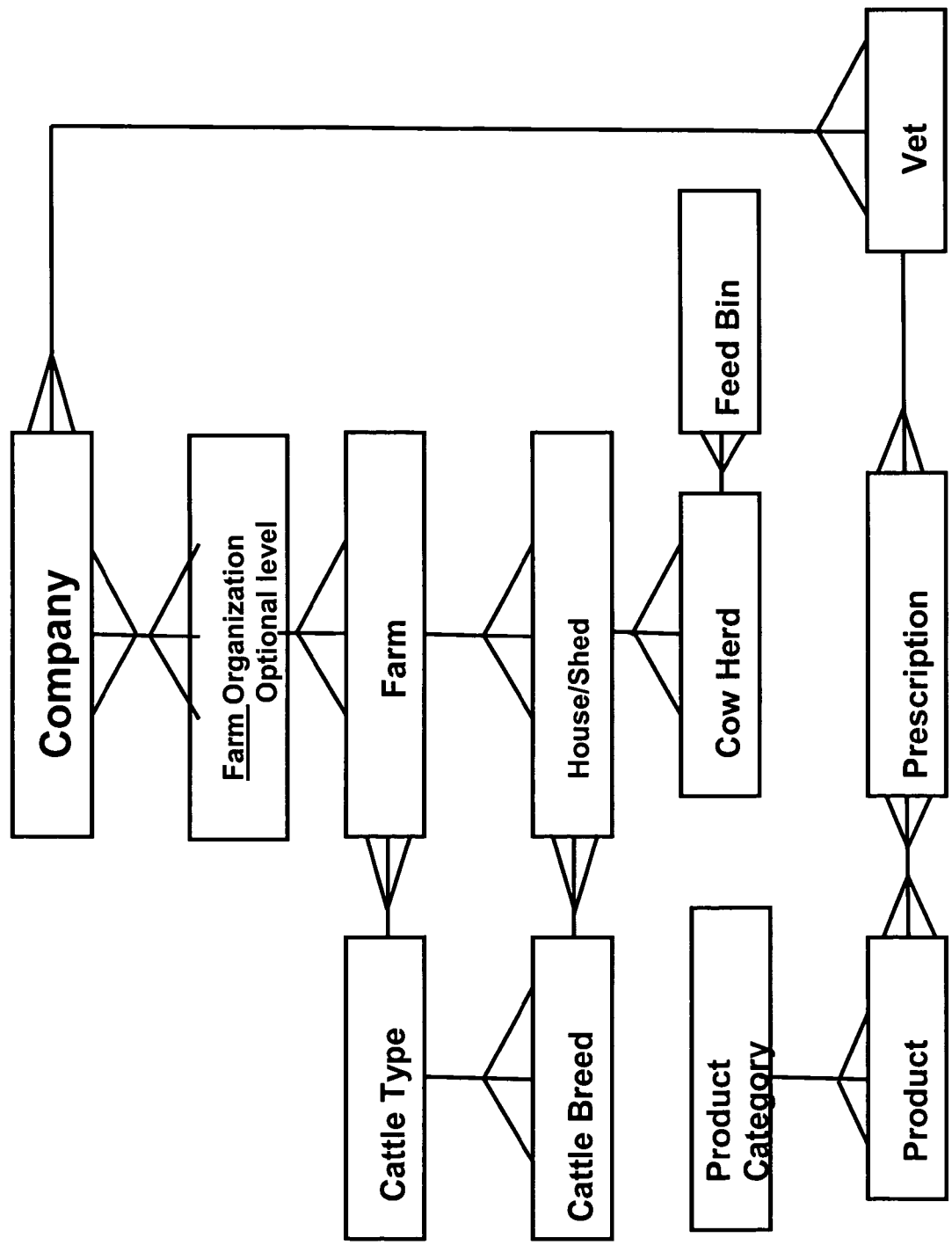

FIG. 8 illustrates potential relationships between the data elements to be entered into the system. Unidirectional arrows indicate, for example, that a barn is typically owned by only one farm, whereas a farm may own several barns. Similarly, a prescription may include veterinarian products.

Figure 9A:
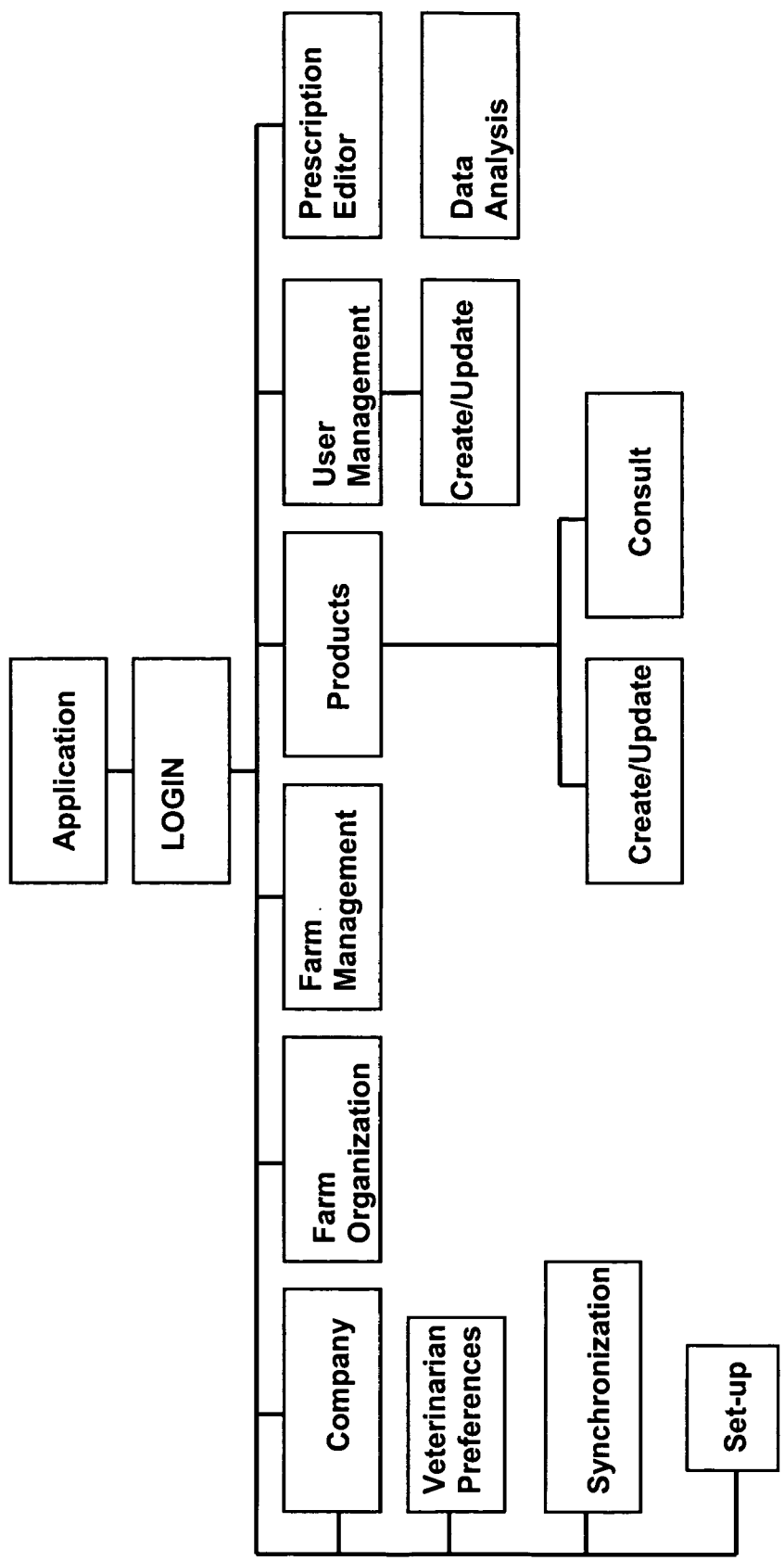

FIG. 9A illustrates the flow of events in the use of the portable computer-based system for data entry on the breeding and rearing of a herd of cows.

Figure 9B:
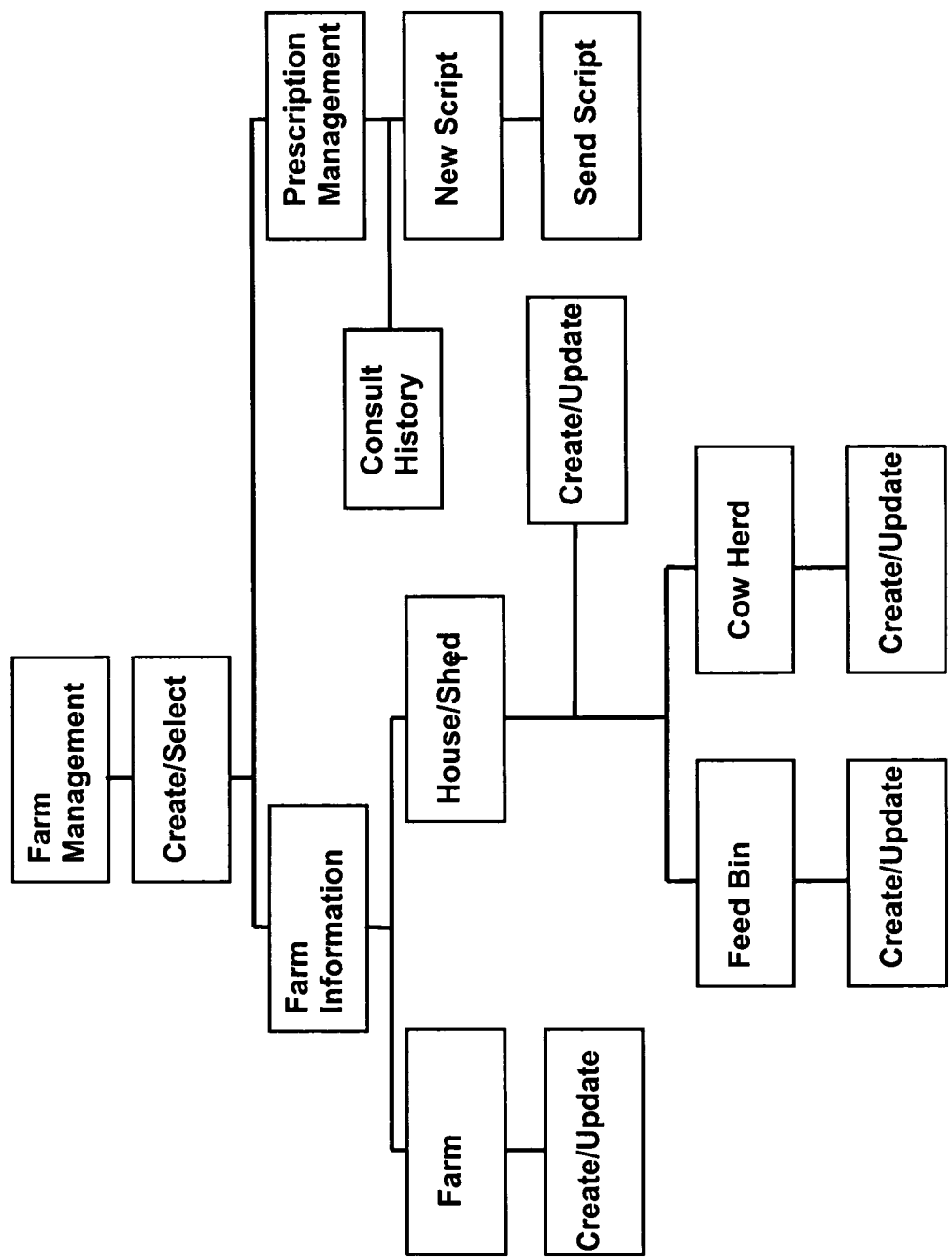

FIG. 9B illustrates the flow of events through the sub-routines related to data entry concerning farm management.

Figure 9C:
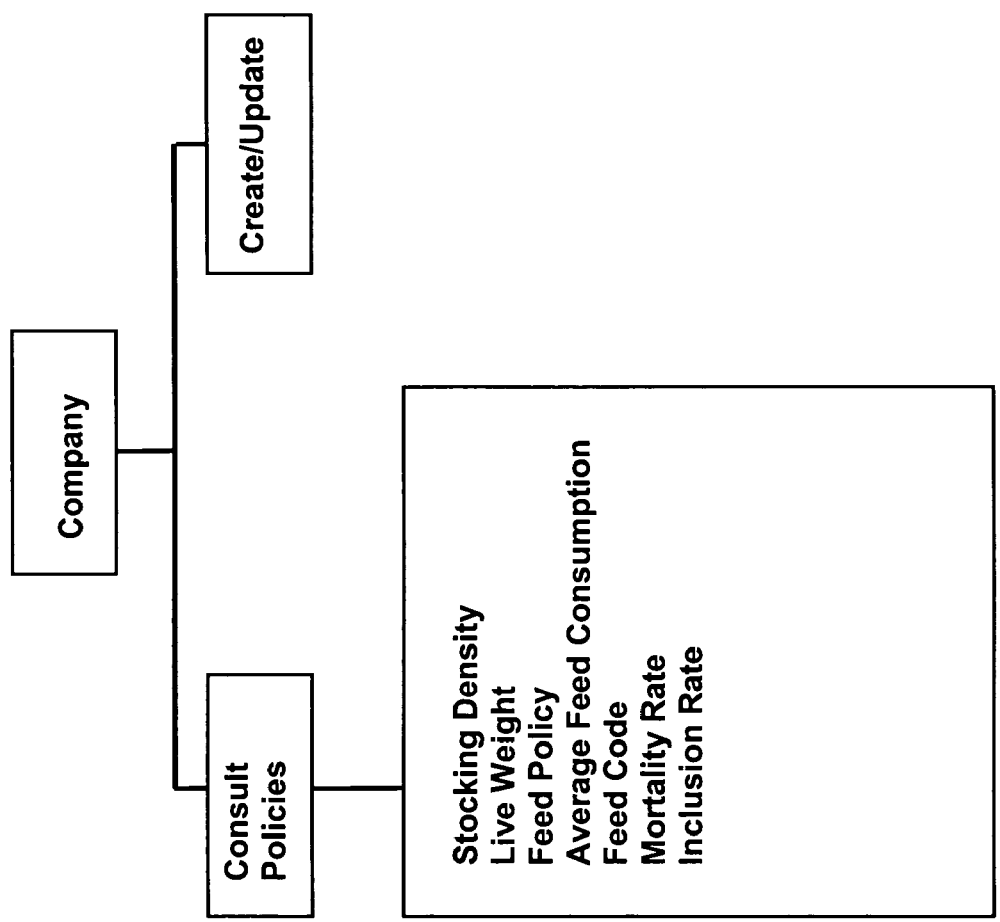

FIG. 9C illustrates the flow of events through the sub-routines related to data entry concerning data specific to a company.

Figure 10:
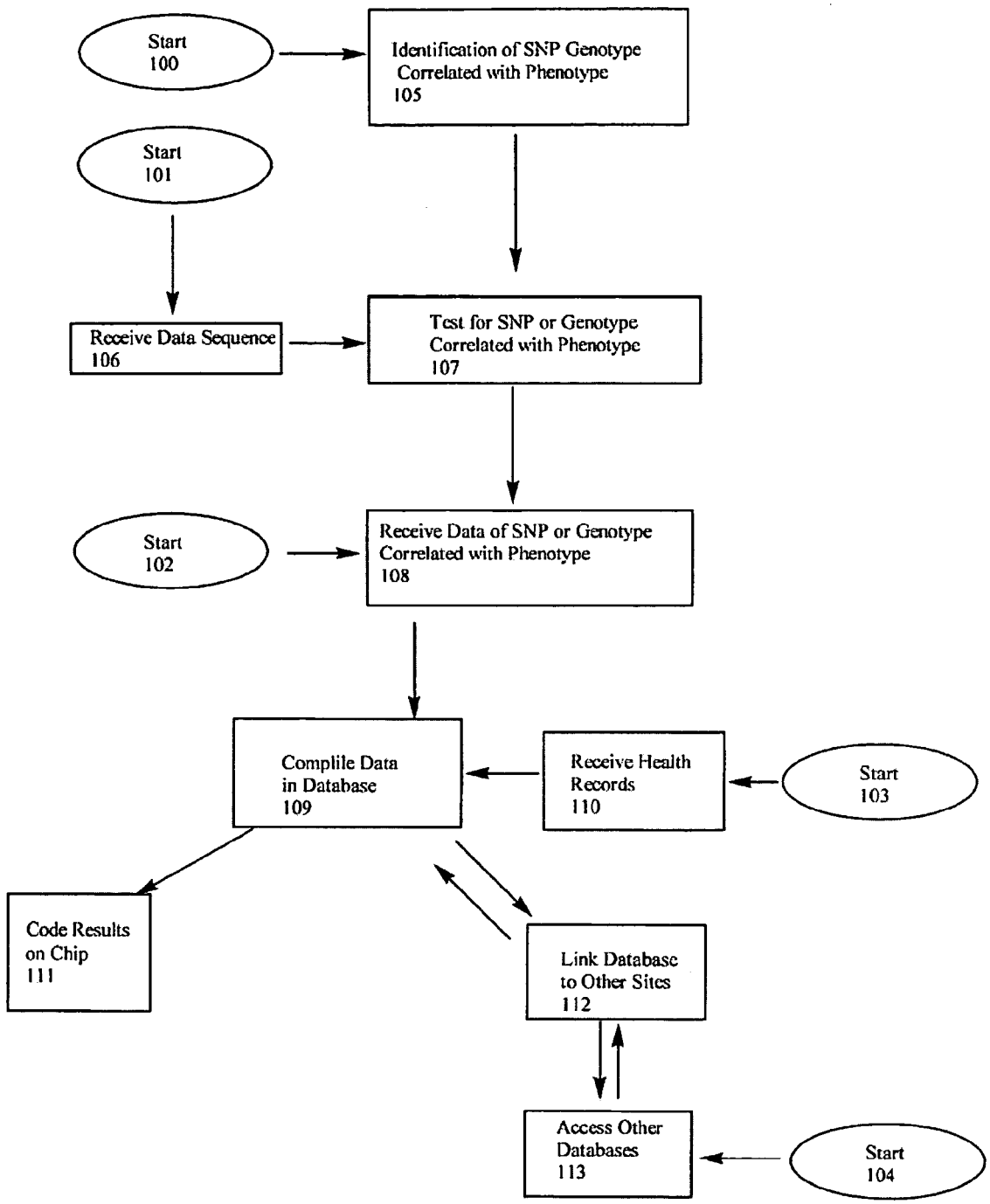

FIG. 10 illustrates a flow chart of the input of data and the output of results from the analysis and the correlation of the data pertaining to the breeding, veterinarian histories, and performance requirements of a group of animals.

DETAILED DESCRIPTION

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed and are intended to be defined as indicated below.

The term "cow" or "cattle" is used generally to refer to an animal of bovine origin of any age. Interchangeable terms include "bovine", "calf", "steer", "bull", "heifer" and the like. It also includes an individual animal in all stages of development, including embryonic and fetal stages. The animals as referred to herein may also include individuals or groups of individuals that are raised for other than food production such as, but not limited to, transgenic animals for the production of biopharmaceuticals including antibodies and other proteins or protein products.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479; 5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "heterozygous" or "heterozygous polymorphism" is meant that the two alleles of a diploid cell or organism at a given locus are different, that is, that they have a different nucleotide exchanged for the same nucleotide at the same place in their sequences.

By "homozygous" or "homozygous polymorphism" is meant that the two alleles of a diploid cell or organism at a given locus are identical, that is, that they have the same nucleotide for nucleotide exchange at the same place in their sequences.

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

As used herein, the term "locus" or "loci" refers to the site of a gene on a chromosome. Pairs of genes, known as "alleles" control the hereditary trait produced by a gene locus. Each animal's particular combination of alleles is referred to as its "genotype". Where both alleles are identical the individual is said to be homozygous for the trait controlled by that gene pair; where the alleles are different, the individual is said to be heterozygous for the trait.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about $1°$ C. to about $10°$ C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching $100°$ C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Methods and materials of the invention may be used more generally to evaluate a DNA sample from an animal, genetically type an individual animal, and detect genetic differences in animals. In particular, a sample of genomic DNA from an animal may be evaluated by reference to one or more controls to determine if a SNP, or group of SNPs, in a gene is present. Any method for determining genotype can be used for determining the genotype in the present invention. Such methods include, but are not limited to, amplimer sequencing, DNA sequencing, fluorescence spectroscopy, fluorescence resonance energy transfer (or "FRET")-based hybridization analysis, high throughput screening, mass spectroscopy, microsatellite analysis, nucleic acid hybridization, polymerase chain reaction (PCR), RFLP analysis and size chromatography (e.g., capillary or gel chromatography), all of which are well known to one of skill in the art. In particular, methods for determining nucleotide polymorphisms, particularly single nucleotide polymorphisms, are described in U.S. Pat. Nos. 6,514,700; 6,503,710; 6,468,742; 6,448,407; 6,410,231; 6,383,756; 6,358,679; 6,322,980; 6,316,230; and 6,287,766 and reviewed by Chen and Sullivan, Pharmacogenomics J 2003; 3(2):77-96, the disclosures of which are incorporated by reference in their entireties. Genotypic data useful in the methods of the invention and methods for the identification and selection of animal traits are based on the presence of SNPs.

A "restriction fragment" refers to a fragment of a polynucleotide generated by a restriction endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

A "single nucleotide polymorphism" or "SNP" refers to a variation in the nucleotide sequence of a polynucleotide that differs from another polynucleotide by a single nucleotide difference. For example, without limitation, exchanging one A for one C, G or T in the entire sequence of polynucleotide constitutes a SNP. It is possible to have more than one SNP in a particular polynucleotide. For example, at one position in a polynucleotide, a C may be exchanged for a T, at another position a G may be exchanged for an A and so on. When referring to SNPs, the polynucleotide is most often DNA.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such a DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "variance" is a difference in the nucleotide sequence among related polynucleotides. The difference may be the deletion of one or more nucleotides from the sequence of one polynucleotide compared to the sequence of a related polynucleotide, the addition of one or more nucleotides or the substitution of one nucleotide for another. The terms "mutation," "polymorphism" and "variance" are used interchangeably herein. As used herein, the term "variance" in the singular is to be construed to include multiple variances; i.e., two or more nucleotide additions, deletions and/or substitutions in the same polynucleotide. A "point mutation" refers to a single substitution of one nucleotide for another.

As used herein, the terms "traits", "quality traits" or "physical characteristics" or "phenotypes" refer to advantageous properties of the animal resulting from genetics. Quality traits include, but are not limited to, the animal's genetic ability to efficiently metabolize energy, produce meat or milk, put on intramuscular fat. Physical characteristics include, but are not limited to, marbled, tender or lean meats. The terms may be used interchangeably.

A "computer system" refers to the hardware means, software means and data storage means used to compile the data of the present invention. The minimum hardware means of computer-based systems of the invention may comprise a central processing unit (CPU), input means, output means, and data storage means. Desirably, a monitor is provided to visualize structure data. The data storage means may be RAM or other means for accessing computer readable media of the invention. Examples of such systems are microcomputer workstations available from Silicon Graphics Incorporated and Sun Microsystems running Unix based, Linux, Windows NT, XP or IBM OS/2 operating systems.

"Computer readable media" refers to any media which can be read and accessed directly by a computer, and includes, but is not limited to: magnetic storage media such as floppy discs, hard storage medium and magnetic tape; optical storage media such as optical discs or CD-ROM; electrical storage media such as RAM and ROM; and hybrids of these categories, such as magnetic/optical media. By providing such computer readable media, the data compiled on a particular animal can be routinely accessed by a user, e.g., a feedlot operator.

The term "data analysis module" is defined herein to include any person or machine, individually or working together, which analyzes the sample and determines the genetic information contained therein. The term may include a person or machine within a laboratory setting.

As used herein, the term "data collection module" refers to any person, object or system obtaining a tissue sample from an animal or embryo. By example and without limitation, the term may define, individually or collectively, the person or machine in physical contact with the animal as the sample is taken, the containers holding the tissue samples, the packaging used for transporting the samples, and the like. Advantageously, the data collector is a person. More advantageously, the data collector is a livestock farmer, a breeder or a veterinarian The term "network interface" is defined herein to include any person or computer system capable of accessing data, depositing data, combining data, analyzing data, searching data, transmitting data or storing data. The term is broadly defined to be a person analyzing the data, the electronic hardware and software systems used in the analysis, the databases storing the data analysis, and any storage media capable of storing the data. Non-limiting examples of network interfaces include people, automated laboratory equipment, computers and computer networks, data storage devices such as, but not limited to, disks, hard drives or memory chips.

The term "breeding history" as used herein refers to a record of the life of an animal or group of animals including, but not limited to, the location, breed, period of housing, as well as a genetic history of the animals, including parentage and descent therefrom, genotype, phenotype, transgenic history if relevant and the like.

The term "husbandry conditions" as used herein refers to parameters relating to the maintenance of animals including, but not limited to, shed or housing temperature, weekly mortality of a herd, water consumption, feed consumption, ventilation rate and quality, litter condition and the like.

The term "veterinary history" as used herein refers to vaccination data of an animal or group of animals, including, but not limited to, vaccine type(s), vaccine batch serial number(s), administered dose, target antigen, method of administering of the vaccine to the recipient animal(s), number of vaccinated animals, age of the animals and the vaccinator. Data relating to a serological or immunological response induced by the vaccine may also be included. "Veterinary history" as used herein is also intended to include the medication histories of the target animal(s) including, but not limited to drug and/or antibiotics administered to the animals including type of administered medication, quantity and dose rates, by whom and when administered, by what route, e.g., oral, subcutaneously and the like, and the response to the medication including desired and undesirable effects thereof.

The term "diagnostic data" as used herein refers to data relating to the health of the animal(s) other than data detailing the vaccination or medication history of the animal(s). For example, the diagnostic data may be a record of the infections experienced by the animal(s) and the response thereof to medications provided to treat such medications. Serological data including antibody or protein composition of the serum or other biofluids may also be diagnostic data useful to input in the methods of the invention. Surgical data pertaining to the animal(s) may be included, such as the type of surgical manipulation, outcome of the surgery and complications arising from the surgical procedure. "Diagnostic data" may also include measurements of such parameters as weight, morbidity, and other characteristics noted by a veterinary service such as the condition of the skin, feet, etc.

The term "welfare data" as used herein refers to the collective accumulation of data pertaining to an animal or group of animals including, but not limited to, a breeding history, a veterinary history, a welfare profile, diagnostic data, quality control data, or any combination thereof.

The term "welfare profile" as used herein refers to parameters such as weight, meat density, crowding levels in breeding or rearing enclosures, psychological behavior of the animal, growth rate and quality and the like.

The term "quality control" as used herein refers to the desired characteristics of the animal(s). For non-poultry animals such as cattle and sheep for example, such parameters include muscle quantity and density, fat content, meat tenderness, milk yield and quality, breeding ability, and the like.

The term "performance parameters" as used herein refers to such factors as meat yield, breeding yield, dairy form, meat quality and yield, productive life and the like that may be the desired goals from the breeding and rearing of the animal(s). Performance parameters may be either generated from the animals themselves, or those parameters desired by a customer or the market.

The term "nutritional data" as used herein refers to the composition, quantity and frequency of delivery of feed, including water, provided to the animal(s).

The term "food safety" as used herein refers to the quality of the meat from a livestock animal, including, but not limited to, preparation time, place and manner, storage of the food product, transportation route, inspection records, texture, color, taste, odor, bacterial content, parasitic content and the like.

It will be apparent to those of skill in the art that the data relating to the health and maintenance of the animals may be variously grouped depending upon the source or intention of the data collector and any one grouping herein is not therefore intended to be limiting.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

In an embodiment wherein the gene of interest is bovine TFAM, the bovine TFAM nucleotide sequence can be selected from, but is not limited to, the sequence corresponding to GenBank Accession Nos. AAFC0211069 or AAFC02019444 (SEQ ID NO: 3) or a fragment thereof or a region of the bovine genome that comprises this sequence.

The present invention, therefore, provides isolated nucleic acids that may specifically hybridize to the nucleotide sequence corresponding to GenBank Accession No. AFC0211069 or AAFC02019444 (SEQ ID NO: 3), or the complement thereof, and which comprises the polymorphic site corresponding to nucleotide positions −1220, −1212 or −995.

The single nucleotide polymorphism(s) of interest may be selected from the group consisting of an A to C substitution at the −1220 nucleotide position in the promoter of the TFAM gene, a T to C substitution at position −1212 in the promoter of the TFAM gene and a T to C substitution at position −995 in the promoter of the TFAM gene.

The SNP advantageous in the present invention is associated with certain economically valuable and heritable traits relating to meat quality in bovines. Therefore, it is an object of the present invention to determine the genotype of a given animal of interest as defined by the TFAM locus SNP according to the present invention. It is also contemplated that the genotype of the animal(s) may be defined by additional SNPs within the TFAM gene or within other genes identified with desirable traits or other characteristics, and in particular by a panel or panels of SNPs.

There are many methods known in the art for determining the sequence of DNA in a sample, and for identifying whether a given DNA sample contains a particular SNP. Any such technique known in the art may be used in performance of the methods of the present invention.

The methods of the present invention allow animals with certain economically valuable heritable traits to be identified based on the presence of SNPs in their genomes and particularly with a SNP located within the promoter of the TFAM gene. The methods further allow, by computer-assisted methods of the invention, to correlate the SNP-associated traits with other data pertinent to the well-being and productive capacity of the animals, or group of animals.

To determine the genotype of a given animal according to the methods of the present invention, it is necessary to obtain a sample of genomic DNA from that animal. Typically, that sample of genomic DNA will be obtained from a sample of tissue or cells taken from that animal. A tissue or cell sample may be taken from an animal at any time in the lifetime of an animal but before the carcass identity is lost. The tissue sample can comprise hair, including roots, hide, bone, buccal swabs, blood, saliva, milk, semen, embryos, muscle or any internal organs. In the methods of the present invention, the source of the tissue sample, and thus also the source of the test nucleic acid sample, is not critical. For example, the test nucleic acid can be obtained from cells within a body fluid of the animal, or from cells constituting a body tissue of the animal. The particular body fluid from which cells are obtained is also not critical to the present invention. For example, the body fluid may be selected from the group consisting of blood, ascites, pleural fluid and spinal fluid. Furthermore, the particular body tissue from which cells are obtained is also not critical to the present invention. For example, the body tissue may be selected from the group consisting of skin, endometrial, uterine and cervical tissue. Both normal and tumor tissues can be used.

Typically, the tissue sample is marked with an identifying number or other indicia that relates the sample to the individual animal from which the sample was taken. The identity of the sample advantageously remains constant throughout the methods and systems of the invention thereby guaranteeing the integrity and continuity of the sample during extraction and analysis. Alternatively, the indicia may be changed in a regular fashion that ensures that the data, and any other associated data, can be related back to the animal from which the data was obtained.

The amount/size of sample required is known to those skilled in the art and for example, can be determined by the subsequent steps used in the method and system of the invention and the specific methods of analysis used. Ideally, the size/volume of the tissue sample retrieved should be as consistent as possible within the type of sample and the species of animal. For example, for cattle, non-limiting examples of sample sizes/methods include non-fatty meat: 0.0002 gm-10.0 gm; hide: 0.0004 gm-10.0 gm; hair roots: at least one and advantageously greater than five; buccal swabs: 15 to 20 seconds of rubbing with modest pressure in the area between outer lip and gum using, for example, a cytology brush; bone: 0.0002 gm-10.0 gm; blood: 30 µl to 50 ml.

Generally, the tissue sample is placed in a container that is labeled using a numbering system bearing a code corresponding to the animal, for example, to the animal's ear tag. Accordingly, the genotype of a particular animal is easily traceable at all times. The sampling device and/or container may be supplied to the farmer, a slaughterhouse or retailer. The sampling device advantageously takes a consistent and reproducible sample from individual animals while simultaneously avoiding any cross-contamination of tissue. Accordingly, the size and volume of sample tissues derived from individual animals would be consistent.

DNA can be isolated from the tissue/cells by techniques known to those skilled in the art (see, e.g., U.S. Pat. Nos. 6,548,256 and 5,989,431; Hirota et al. (1989) Jinrui Idengaku Zasshi. 34: 217-23 and John et al. (1991) Nucleic Acids Res. 19:408, the disclosures of which are incorporated by reference in their entireties). For example, high molecular weight DNA may be purified from cells or tissue using proteinase K extraction and ethanol precipitation. DNA, however, may be extracted from an animal specimen using any other suitable methods known in the art.

In one embodiment, the presence or absence of the SNP of any of the genes of the present invention may be determined by sequencing the region of the genomic DNA sample that spans the polymorphic locus. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can be amplified using the polymerase chain reaction. The amplified region of DNA form can then be sequenced using any method known in the art, for example using an automatic nucleic acid sequencer. The detection of a given SNP can then be performed using hybridization of probes and or using PCR-based amplification methods. Such methods are described in more detail below.

The methods of the present invention may use oligonucleotides useful as primers to amplify specific nucleic acid sequences of the TFAM gene, advantageously of the region encompassing a TFAM SNP. Such fragments should be of sufficient length to enable specific annealing or hybridization to the nucleic acid sample. The sequences typically will be about 8 to about 44 nucleotides in length. Longer sequences, e.g., from about 14 to about 50, may be advantageous for certain embodiments. The design of primers is well known to one of ordinary skill in the art.

Inventive nucleic acid molecules include nucleic acid molecules having at least 70% identity or homology or similarity with a TFAM gene or probes or primers derived therefrom such as at least 75% identity or homology or similarity, preferably at least 80% identity or homology or similarity, more preferably at least 85% identity or homology or similarity such as at least 90% identity or homology or similarity, more preferably at least 95% identity or homology or similarity such as at least 97% identity or homology or similarity. The nucleotide sequence similarity or homology or identity can be determined using the "Align" program of Myers and Miller, ("Optimal Alignments in Linear Space", CABIOS 4, 11-17, 1988) and available at NCBI. Alternatively or additionally, the terms "similarity" or "identity" or "homology", for instance, with respect to a nucleotide sequence, is intended to indicate a quantitative measure of homology between two sequences. The percent sequence similarity can be calculated as $(N_{ref} - N_{dif})*100/N_{ref}$, wherein $N_{dif}$ is the total number of non-identical residues in the two sequences when aligned and wherein $N_{ref}$ is the number of residues in one of the sequences. Hence, the DNA sequence AGTCAGTC will have a sequence similarity of 75% with the sequence AATCAATC ($N_{ref}=8$; $N_{dif}=2$). Alternatively or additionally, "similarity" with respect to sequences refers to the number of positions with identical nucleotides divided by the number of nucleotides in the shorter of the two sequences wherein alignment of the two sequences can be determined in accordance with the Wilbur and Lipman algorithm (Wilbur and Lipman, 1983 PNAS USA 80:726), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity with DNA sequences, thymidine (T) in the DNA sequence is considered equal to uracil (U) in the RNA sequence.

A probe or primer can be any stretch of at least 8, preferably at least 10, more preferably at least 12, 13, 14, or 15, such as at least 20, e.g., at least 23 or 25, for instance at least 27 or 30 nucleotides in a TFAM gene which are unique to a TFAM gene. As to PCR or hybridization primers or probes and optimal lengths therefor, reference is also made to Kajimura et al., GATA 7(4):71-79 (1990).

RNA sequences within the scope of the invention are derived from the DNA sequences, by thymidine (T) in the DNA sequence being considered equal to uracil (U) in RNA sequences.

The oligonucleotides can be produced by a conventional production process for general oligonucleotides. They can be produced, for example, by a chemical synthesis process or by a microbial process that makes use of a plasmid vector, a phage vector or the like. Further, it is suitable to use a nucleic acid synthesizer.

To label an oligonucleotide with the fluorescent dye, one of conventionally known labeling methods can be used (Tyagi & Kramer (1996) Nature Biotechnology 14: 303-308; Schofield et al. (1997) Appl. and Environ. Microbiol. 63: 1143-1147; Proudnikov & Mirzabekov (1996) Nucl. Acids Res. 24: 4532-4535). Alternatively, the oligonucleotide may be labeled with a radiolabel e.g., $^3H$, $^{125}I$, $^{35}S$, $^{14}C$, $^{32}P$, etc. Well-known labeling methods are described, for example, in Sambrook et al. (2001) Molecular Cloning: A Laboratory Manual, 3rd ed., Cold Spring Harbor Press. The label is coupled directly or indirectly to a component of the oligonucleotide according to methods well known in the art. Reversed phase chromatography or the like used to provide a nucleic acid probe for use in the present invention can purify the synthesized oligonucleotide labeled with a marker. An advantageous probe form is one labeled with a fluorescent dye at the 3'- or 5'-end and containing G or C as the base at the labeled end. If the 5'-end is labeled and the 3'-end is not labeled, the OH group on the C atom at the 3'-position of the 3'-end ribose or deoxyribose may be modified with a phosphate group or the like although no limitation is imposed in this respect.

During the hybridization of the nucleic acid target with the probes, stringent conditions may be utilized, advantageously along with other stringency affecting conditions, to aid in the hybridization. Detection by differential disruption is particularly advantageous to reduce or eliminate slippage hybridization among probes and target, and to promote more effective hybridization. In yet another aspect, stringency conditions may be varied during the hybridization complex stability determination so as to more accurately or quickly determine whether a SNP is present in the target sequence.

One method for determining the genotype at the polymorphic gene locus encompasses obtaining a nucleic acid sample, hybridizing the nucleic acid sample with a probe, and disrupting the hybridization to determine the level of disruption energy required wherein the probe has a different disruption energy for one allele as compared to another allele. In one example, there can be a lower disruption energy, e.g., melting temperature, for an allele that harbors a cytosine residue at a polymorphic locus, and a higher required energy for an allele with a different residue at that polymorphic locus. This can be achieved where the probe has 100% homology with one allele (a perfectly matched probe), but has a single mismatch with the alternative allele. Since the perfectly matched probe is bound more tightly to the target DNA than the mismatched probe, it requires more energy to cause the hybridized probe to dissociate.

In a further step of the above method, a second ("anchor") probe may be used. Generally, the anchor probe is not specific to either allele, but hybridizes regardless of what nucleotide is present at the polymorphic locus. The anchor probe does not affect the disruption energy required to disassociate the hybridization complex but, instead, contains a complementary label for using with the first ("sensor") probe.

Hybridization stability may be influenced by numerous factors, including thermoregulation, chemical regulation, as well as electronic stringency control, either alone or in combination with the other listed factors. Through the use of stringency conditions, in either or both of the target hybridization step or the sensor oligonucleotide stringency step, rapid completion of the process may be achieved. This is desirable to achieve properly indexed hybridization of the target DNA to attain the maximum number of molecules at a test site with an accurate hybridization complex. By way of example, with the use of stringency, the initial hybridization step may be completed in ten minutes or less, more advantageously five minutes or less, and most advantageously two minutes or less. Overall, the analytical process may be completed in less than half an hour.

In one mode, the hybridization complex is labeled and the step of determining the amount of hybridization includes detecting the amounts of labeled hybridization complex at the test sites. The detection device and method may include, but is not limited to, optical imaging, electronic imaging, imaging with a CCD camera, integrated optical imaging, and mass spectrometry. Further, the amount of labeled or unlabeled probe bound to the target may be quantified. Such quantification may include statistical analysis. The labeled portion of the complex may be the target, the stabilizer, the probe or the hybridization complex in toto. Labeling may be by fluorescent labeling selected from the group of, but not limited to, Cy3, Cy5, Bodipy Texas Red, Bodipy Far Red, Lucifer Yellow, Bodipy 630/650-X, Bodipy R6G-X and 5-CR 6G. Colormetric labeling, bioluminescent labeling and/or chemiluminescent labeling may further accomplish labeling. Labeling further may include energy transfer between molecules in the hybridization complex by perturbation analysis, quenching, electron transport between donor and acceptor molecules, the latter of which may be facilitated by double stranded match hybridization complexes. Optionally, if the hybridization complex is unlabeled, detection may be accomplished by measurement of conductance differential between double stranded and non-double stranded DNA. Further, direct detection may be achieved by porous silicon-based optical interferometry or by mass spectrometry. In using mass spectrometry no fluorescent or other label is necessary. Rather detection is obtained by extremely high levels of mass resolution achieved by direct measurement, for example, by time of flight (TOF) or by electron spray ionization (ESI). Where mass spectrometry is contemplated, probes having a nucleic acid sequence of 50 bases or less are advantageous.

The label may be amplified, and may include, for example, branched or dendritic DNA. If the target DNA is purified, it may be un-amplified or amplified. Further, if the purified target is amplified and the amplification is an exponential method, it may be, for example, PCR amplified DNA or strand displacement amplification (SDA) amplified DNA. Linear methods of DNA amplification such as rolling circle or transcriptional runoff may also be used.

Where it is desired to amplify a fragment of DNA that comprises a SNP according to the present invention, the forward and reverse primers may have contiguous stretches of about 8, 9, 10, 11, 12, 13, 14, 15, 16, 17, 18, 19, 20, 21, 22, 23, 24, 25, 26, 27, 28, 29, 30 or any other length up to and including about 50 nucleotides in length. The sequences to which the forward and reverse primers anneal are advantageously located on either side of the particular nucleotide position that is substituted in the SNP to be amplified.

A detectable label can be incorporated into a nucleic acid during at least one cycle of an amplification reaction. Spectroscopic, photochemical, biochemical, immunochemical, electrical, optical or chemical means can detect such labels. Useful labels in the present invention include fluorescent dyes (e.g., fluorescein isothiocyanate, Texas red, rhodamine, and the like), radiolabels (e.g., $^3$H, $^{125}$I, $^{35}$S, $^{14}$C, $^{32}$P, etc.), enzymes (e.g. horseradish peroxidase, alkaline phosphatase etc.) calorimetric labels such as colloidal gold or colored glass or plastic (e.g. polystyrene, polypropylene, latex, etc.) beads. The label is coupled directly or indirectly to a component of the assay according to methods well known in the art. As indicated above, a wide variety of labels are used, with the choice of label depending on sensitivity required, ease of conjugation with the compound, stability requirements, available instrumentation, and disposal provisions. Non-radioactive labels are often attached by indirect means. Polymerases can also incorporate fluorescent nucleotides during synthesis of nucleic acids.

Reagents allowing the sequencing of reaction products can be utilized herein. For example, chain-terminating nucleotides will often be incorporated into a reaction product during one or more cycles of a reaction. Commercial kits containing the reagents most typically used for these methods of DNA sequencing are available and widely used. PCR exonuclease digestion methods for DNA sequencing can also be used. Many methods of sequencing genomic DNA are known in the art, and any such method can be used, see for example Sambrook et al. (2001) Molecular Cloning: A Laboratory Manual, 3rd ed., Cold Spring Harbor Press. For example, as described below, a DNA fragment spanning the location of the SNP of interest can amplified using the polymerase chain reaction or some other cyclic polymerase mediated amplification reaction. The amplified region of DNA can then be sequenced using any method known in the art. Advantageously, the nucleic acid sequencing is by automated methods (reviewed by Meldrum, (2000) Genome Res. 10: 1288-303, the disclosure of which is incorporated by reference in its entirety), for example using a Beckman CEQ 8000 Genetic Analysis System (Beckman Coulter Instruments, Inc.). Methods for sequencing nucleic acids include, but are not limited to, automated fluorescent DNA sequencing (see, e.g., Watts & MacBeath, (2001) Methods Mol Biol. 167: 153-70 and Mac-Beath et al. (2001) Methods Mol Biol. 167:119-52), capillary electrophoresis (see, e.g., Bosserhoff et al. (2000) Comb Chem High Throughput Screen. 3: 455-66), DNA sequencing chips (see, e.g., Jain, (2000) Pharmacogenomics. 1: 289-307), mass spectrometry (see, e.g., Yates, (2000) Trends Genet. 16: 5-8), pyrosequencing (see, e.g., Ronaghi, (2001) Genome Res. 11: 3-11), and ultrathin-layer gel electrophoresis (see, e.g., Guttman & Ronai, (2000) Electrophoresis. 21: 3952-64), the disclosures of which are hereby incorporated by reference in their entireties. The sequencing can also be done by a commercial company. Examples of such companies include, but are not limited to, the University of Georgia Molecular Genetics Instrumentation Facility (Athens, Ga.) or SeqWright DNA Technologies Services (Houston, Tex.).

A SNP-specific probe can also be used in the detection of the SNP in amplified specific nucleic acid sequences of the target gene, such as the amplified PCR products generated using the primers described above. In certain embodiments, these SNP-specific probes consist of oligonucleotide fragments. Advantageously, the fragments are of sufficient length to provide specific hybridization to the nucleic acid sample. The use of a hybridization probe of between 10 and 50 nucleotides in length allows the formation of a duplex molecule that is both stable and selective. Molecules having complementary sequences over stretches greater than 12 bases in length are generally advantageous, in order to increase stability and selectivity of the hybrid, and thereby improve the quality and degree of particular hybrid molecules obtained. One will generally prefer to design nucleic acid molecules having stretches of 16 to 24 nucleotides, or even longer where desired. A tag nucleotide region may be included, as at the 5' end of the primer that may provide a site to which an oligonucleotide sequencing primer may hybridize to facilitate the sequencing of multiple PCR samples.

The probe sequence must span the particular nucleotide position that may be substituted in the particular SNP to be detected. Advantageously, two or more different "allele-specific probes" may be used for analysis of a SNP, a first allele-specific probe for detection of one allele, and a second allele-specific probe for the detection of the alternative allele.

It will be understood that this invention is not limited to the particular primers and probes disclosed herein and is intended to encompass at least nucleic acid sequences that are hybridizable to the nucleotide sequence disclosed herein, the complement or a fragment thereof, or are functional sequence analogs of these sequences. It is also contemplated that a particular trait of an animal may be determined by using a panel of SNPs associated with that trait. Several economically relevant traits may be characterized by the presence or absence of one or more SNPs and by a plurality of SNPs in different genes. One or more panels of SNPs may be used in the methods of the invention to define the phenotypic profile of the subject animal.

Homologs (i.e., nucleic acids derived from other species) or other related sequences (e.g., paralogs) can be obtained under conditions of standard or stringent hybridization conditions with all or a portion of the particular sequence as a probe using methods well known in the art for nucleic acid hybridization and cloning.

The genetic markers, probes thereof, methods, and kits of the invention are also useful in a breeding program to select for breeding those animals having desirable phenotypes for various economically important traits, such as improved meat quality and yield, in particular meat tenderness. Continuous selection and breeding of animals, such as livestock, that are at least heterozygous and advantageously homozygous for desirable alleles of the TFAM gene polymorphic sites associated with economically relevant traits of growth, feed intake, efficiency and/or carcass merit, would lead to a breed, line, or population having higher numbers of offspring with economically relevant traits of growth, feed intake, efficiency and carcass merit. Thus, the TFAM SNPs of the present invention can be used as a selection tool.

Desirable phenotypes include, but are not limited to, feed intake, growth rate, body weight, carcass merit and composition, and milk yield. Specific carcass traits with desirable phenotypes include, but are not limited to, additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF %, %), marbling score (MBS, 10 to 99), marbling score divided by days on feed (MBS/DOF), quality grade, less than or equal to select versus greater than or equal to choice (QG, <Se vs, >Ch), ribeye area (REA, in$^2$), ribeye area per hundred weight HCW (REA/cwt HCW, in$^2$/100 lb hot carcass weight (HCW) and subcutaneous fat depth (SFD).

One aspect of the present invention provides for grouping animals and methods for managing livestock production comprising grouping livestock animals such as cattle according the genotype as defined by panels of SNPs, each panel comprising at least one SNP, one or more of which are in the TFAM gene of the present invention. Other SNPs that may be included in panels of SNPs include, but not limited to, SNPs found in the calpastatin gene, GHR gene, FABP4 gene, ghrelin gene, leptin gene, NPY gene, ob gene, UASMS1 gene, UASMS2 gene, UASMS3 gene and/or the UCP2 gene. The genetic selection and grouping methods of the present invention can be used in conjunction with other conventional phenotypic grouping methods such as grouping animals by visible characteristics such as weight, frame size, breed traits, and the like. The methods of the present invention provide for producing cattle having improved heritable traits, and can be used to optimize the performance of livestock herds in areas such as breeding, feed intake, carcass/meat quality and milk production. The present invention provides methods of screening livestock to determine those more likely to develop a desired body condition by identifying the presence or absence of one or more gene polymorphisms correlated with meat quality.

As described above, and in the Examples, there are various phenotypic traits with which the SNPs of the present invention may be associated. Each of the phenotypic and genetic traits can be tested using the methods described in the Examples, or using any suitable methods known in the art. Using the methods of the invention, a farmer, or feedlot operator, or the like, can group cattle according to each animal's genetic propensity for a desired trait such as growth rate, feed intake or feeding behavior, as determined by SNP genotype. The cattle are tested to determine homozygosity or heterozygosity with respect to the SNP alleles of one or more genes so that they can be grouped such that each pen contains cattle with like genotypes. Each pen of animals is then fed and otherwise maintained in a manner and for a time determined by the feedlot operator, and then slaughtered.

The individual genotypic data derived from a panel or panels of SNPs for each animal or a herd of animals can be recorded and associated with various other data of the animal, e.g. health information, parentage, husbandry conditions, vaccination history, herd records, subsequent food safety data and the like. Such information can be forwarded to a government agency to provide traceability of an animal or meat product, or it may serve as the basis for breeding, feeding and marketing information. Once the data has or has not been associated with other data, the data is stored in an accessible database, such as, but not limited to, a computer database or a microchip implanted in the animal. The methods of the invention may provide an analysis of the input data that may be compared with parameters desired by the operator. These parameters include, but are not limited to, such as breeding goals, egg laying targets, vaccination levels of a herd. If the performance or properties of the animals deviates from the desired goals, the computer-based methods may trigger an alert to allow the operator to adjust vaccination doses, medications, feed etc accordingly.

The results of the analysis provide data that are associated with the individual animal or to the herd, in whole or in part, from which the sample was taken. The data are then kept in an accessible database, and may or may not be associated with other data from that particular individual or from other animals.

Data obtained from individual animals may be stored in a database that can be integrated or associated with and/or cross-matched to other databases. The database along with the associated data allows information about the individual animal to be known through every stage of the animal's life, i.e., from conception to consumption of the animal product.

The accumulated data and the combination of the genetic data with other types of data of the animal provides access to information about parentage, identification of herd, health information including vaccinations, exposure to diseases, feedlot location, diet and ownership changes. Information such as dates and results of diagnostic or routine tests are easily stored and attainable. Such information would be especially valuable to companies, particularly those who seek superior breeding lines.

Each animal may be provided with a unique identifier. The animal can be tagged, as in traditional tracing programs or have implant computer chips providing stored and readable data or provided with any other identification method which associates the animal with its unique identifier.

The database containing the SNP-based genotype results for each animal or the data for each animal can be associated or linked to other databases containing data, for example, which may be helpful in selecting traits for grouping or subgrouping of an animal. For example, and not for limitation, data pertaining to animals having particular vaccination or medication protocols, can optionally be further linked with data pertaining to animals having food from certain food sources. The ability to refine a group of animals is limited only by the traits sought and the databases containing information related to those traits.

Databases that can usefully be associated with the methods of the invention include, but are not limited to, specific or general scientific data. Specific data includes, but is not limited to, breeding lines, sires, dames, and the like, other animals' genotypes, including whether or not other specific animals possess specific genes, including transgenic genetic elements, location of animals which share similar or identical genetic characteristics, and the like. General data includes, but is not limited to, scientific data such as which genes encode for specific quality characteristics, breed association data, feed data, breeding trends, and the like.

One method of the present invention includes providing the animal owner or customer with sample collection equipment, such as swabs and tags useful for collecting samples from which genetic data may be obtained. Advantageously, the packaging is encoded with a bar code label. The tags are encoded with the same identifying indicia, advantageously with a matching bar code label. Optionally, the packaging contains means for sending the tags to a laboratory for analysis. The optional packaging is also encoded with identifying indicia, advantageously with a bar code label.

The method optionally includes a system wherein a database account is established upon ordering the sampling equipment. The database account identifier corresponds to the identifying indicia of the tags and the packaging. Upon shipment of the sampling equipment in fulfillment of the order, the identifying indicia are recorded in a database. Advantageously, the identifier is a bar code label which is scanned when the tags are sent. When the tags are returned to the testing facility, the identifier is again recorded and matched to the information previously recorded in the database upon shipment of the vial to the customer. Once the genotyping is completed, the information is recorded in the database and coded with the unique identifier. Test results are also provided to the customer or animal owner.

The data stored in the genotype database can be integrated with or compared to other data or databases for the purpose of identifying animals based on genetic propensities. Other data or databases include, but are not limited to, those containing information related to SNP-based DNA testing, vaccination, Sure Health pre-conditioning program, estrus and pregnancy results, hormone levels, food safety/contamination, somatic cell counts, mastitis occurrence, diagnostic test results, milk protein levels, milk fat, vaccine status, health records, mineral levels, trace mineral levels, herd performance, and the like.

The present invention, therefore, encompasses computer-assisted methods for tracking the breeding and veterinary histories of livestock animals encompassing using a computer-based system comprising a programmed computer comprising a processor, a data storage system, an input device and an output device, and comprising the steps of generating a profile of a livestock animal by inputting into the programmed computer through the input device genotype data of the animal, wherein the genotype may be defined by a panel of at least two single nucleotide polymorphisms that predict at least one physical trait of the animal, inputting into the programmed computer through the input device welfare data of the animal, correlating the inputted welfare data with the phenotypic profile of the animal using the processor and the data storage system, and outputting a profile of the animal or group of animals to the output device.

The databases and the analysis thereof will be accessible to those to whom access has been provided. Access can be provided through rights to access or by subscription to specific portions of the data. For example, the database can be accessed by owners of the animal, the test site, the entity providing the sample to the test site, feedlot personnel, and veterinarians. The data can be provided in any form such as by accessing a website, fax, email, mailed correspondence, automated telephone, or other methods for communication. These data can also be encoded on a portable storage device, such as a microchip, that can be implanted in the animal. Advantageously, information can be read and new information added without removing the microchip from the animal.

The present invention comprises systems for performing the methods disclosed herein. Such systems comprise devices, such as computers, internet connections, servers, and storage devices for data. The present invention also provides for a method of transmitting data comprising transmission of information from such methods herein discussed or steps thereof, e.g., via telecommunication, telephone, video conference, mass communication, e.g., presentation such as a computer presentation (e.g., POWERPOINT), internet, email, documentary communication such as computer programs (e.g., WORD) and the like.

Systems of the present invention may comprise a data collection module, which includes a data collector to collect data from an animal or embryo and transmit the data to a data analysis module, a network interface for receiving data from the data analysis module, and optionally further adapted to combine multiple data from one or more individual animals, and to transmit the data via a network to other sites, or to a storage device.

More particularly, systems of the present invention comprise a data collection module, a data analysis module, a network interface for receiving data from the data analysis module, and optionally further adapted to combine multiple data from one or more individual animals, and to transmit the data via a network to other sites, and/or a storage device. For example, the data collected by the data collection module leads to a determination of the absence or presence of a SNP of a gene in the animal or embryo, and for example, such data is transmitted when the feeding regimen of the animal is planned.

In one embodiment where the data is implanted on a microchip on a particular animal, the farmer can optimize the efficiency of managing the herd because the farmer is able to identify the genetic predispositions of an individual animal as well as past, present and future treatments (e.g., vaccinations and veterinarian visits). The invention, therefore also provides for accessing other databases, e.g., herd data relating to genetic tests and data performed by others, by datalinks to other sites. Therefore, data from other databases can be transmitted to the central database of the present invention via a network interface for receiving data from the data analysis module of the other databases.

The invention relates to a computer system and a computer readable media for compiling data on an animal, the system containing inputted data on that animal, such as but not limited to, vaccination and medication histories, DNA testing, thyroglobulin testing, leptin, MMI (Meta Morphix Inc.), bovine spongiform encephalopathy (BSE) diagnosis, brucellosis vaccination, FMD (foot and mouth disease) vaccination, BVD (bovine viral diarrhea) vaccination, Sure Health preconditioning program, estrus and pregnancy results, tuberculosis, hormone levels, food safety/contamination, somatic cell counts, mastitis occurrence, diagnostic test results, milk protein levels, milk fat, vaccine status, health records, mineral levels, trace mineral levels, herd performance, and the like. The data of the animal can also include prior treatments as well as suggested tailored treatment depending on the genetic predisposition of that animal toward a particular disease.

The invention also provides for a computer-assisted method for improving animal production comprising using a computer system, e.g., a programmed computer comprising a processor, a data storage system, an input device and an output device, the steps of inputting into the programmed computer through the input device data comprising a breeding, veterinary, medication, diagnostic data and the like of an animal, correlating a physical characteristic predicted by the genotype using the processor and the data storage system, outputting to the output device the physical characteristic correlated to the genotype, and feeding the animal a diet based upon the physical characteristic, thereby improving livestock production.

The invention further provides for a computer-assisted method for optimizing efficiency of feedlots for livestock comprising using a computer system, e.g., a programmed computer comprising a processor, a data storage system, an input device and an output device, and the steps of inputting into the programmed computer through the input device data comprising a breeding, veterinary history of an animal, correlating the breeding, veterinary histories using the processor and the data storage system, outputting to the output device the physical characteristic correlated to the genotype, and feeding the animal a diet based upon the physical characteristic, thereby optimizing efficiency of feedlots for livestock.

The invention further comprehends methods of doing business by providing access to such computer readable media and/or computer systems and/or data collected from animals to users; e.g., the media and/or sequence data can be accessible to a user, for instance on a subscription basis, via the Internet or a global communication/computer network; or, the computer system can be available to a user, on a subscription basis.

In one embodiment, the invention provides for a computer system for managing livestock comprising physical characteristics and databases corresponding to one or more animals. In another embodiment, the invention provides for computer readable media for managing livestock comprising physical characteristics and veterinary histories corresponding to one or more animals. The invention further provides methods of doing business for managing livestock comprising providing to a user the computer system and media described above or physical characteristics and veterinary histories corresponding to one or more animals. The invention further encompasses methods of transmitting information obtained in any method or step thereof described herein or any information described herein, e.g., via telecommunications, telephone, mass communications, mass media, presentations, internet, email, etc.

The invention further encompasses kits useful for screening nucleic acid isolated from one or more bovine individuals for allelic variation of any one of the mitochondrial transcription factor genes, and in particular for any of the SNPs described herein, wherein the kits may comprise at least one oligonucleotide selectively hybridizing to a nucleic acid comprising any one of the one or more of which are TFAM sequences described herein and instructions for using the oligonucleotide to detect variation in the nucleotide corresponding to the SNP of the isolated nucleic acid.

One embodiment of this aspect of the invention provides an oligonucleotide that specifically hybridizes to the isolated nucleic acid molecule of this aspect of the invention, and wherein the oligonucleotide hybridizes to a portion of the isolated nucleic acid molecule comprising any one of the polymorphic sites in the TFAM sequences described herein.

Another embodiment of the invention is an oligonucleotide that specifically hybridizes under high stringency conditions to any one of the polymorphic sites of the TFAM gene, wherein the oligonucleotide is between about 18 nucleotides and about 50 nucleotides.

In another embodiment of the invention, the oligonucleotide comprises a central nucleotide specifically hybridizing with a TFAM gene polymorphic site of the portion of the nucleic acid molecule.

Another aspect of the invention is a method of identifying a TFAM polymorphism in a nucleic acid sample comprising isolating a nucleic acid molecule encoding TFAM or a fragment thereof and determining the nucleotide at the polymorphic site.

Another aspect of the invention is a method of screening cattle to determine those bovines more likely to exhibit a biological difference in meat quality comprising the steps of obtaining a sample of genetic material from a bovine; and assaying for the presence of a genotype in the bovine which is associated with meat quality, the genotype characterized by a polymorphism in any one of the mitochondrial transcription factor genes.

In other embodiments of this aspect of the invention, the step of assaying is selected from the group consisting of: restriction fragment length polymorphism (RFLP) analysis, minisequencing, MALD-TOF, SINE, heteroduplex analysis, single strand conformational polymorphism (SSCP), denaturing gradient gel electrophoresis (DGGE) and temperature gradient gel electrophoresis (TGGE).

In various embodiments of the invention, the method may further comprise the step of amplifying a region of the TFAM gene or a portion thereof that contains the polymorphism. In other embodiments of the invention, the amplification may include the step of selecting a forward and a reverse sequence primer capable of amplifying a region of the TFAM gene.

Another aspect of the invention is a computer-assisted method for predicting which livestock animals possess a biological difference in meat quality comprising: using a computer system, e.g., a programmed computer comprising a processor, a data storage system, an input device and an output device, the steps of: (a) inputting into the programmed computer through the input device data comprising a TFAM genotype of an animal, (b) correlating growth, feed intake, efficiency or carcass merit quality predicted by the TFAM genotype using the processor and the data storage system and (c) outputting to the output device the meat quality correlated to the TFAM genotype, thereby predicting which livestock animals possess a particular growth level, feed intake, efficiency or carcass merit quality.

Yet another aspect of the invention is a method of doing business for managing livestock comprising providing to a user computer system for managing livestock comprising physical characteristics and genotypes corresponding to one or more animals or a computer readable media for managing livestock comprising physical characteristics and genotypes corresponding to one or more animals or physical characteristics and genotypes corresponding to one or more animals.

The invention will now be further described by way of the following non-limiting examples.

EXAMPLES

Example 1

This Example provides DNA sequences, genetic polymorphisms and significant associations with marbling and subcutaneous fat depth in Wagyu x Limousin $F_2$ crosses for the bovine mitochondrial transcription factor A (TFAM) gene.

Mitochondrial transcription factor A (TFAM), a nucleus-encoded protein plays an important role in initiation of transcription and replication of mitochondrial DNA (mtDNA). Decreased expression in nuclear-encoded mitochondrial genes has been associated with onset of obesity in mice. Therefore, it was hypothesized that genetic variants in TFAM gene influence mitochondrial biogenesis consequently affecting body fat deposition and energy metabolism. In the present study, both cDNA (2259 bp) and genomic DNA (16,666 bp) sequences were generated for the bovine TFAM gene using a combination of in silico cloning with targeted region PCR amplification. Alignment of both cDNA and genomic sequences led to the determination of genomic organization and characterization of the promoter region of the bovine TFAM gene. Unfortunately, no polymorphisms were detected in the coding region, but two closely linked A/C and C/T single nucleotide polymorphisms (SNPs) were found in the bovine TFAM promoter. These two SNPs were genotyped on 237 $F_2$ Wagyu x Limousin animals with recorded phenotypes for marbling and subcutaneous fat depth (SFD). Statistical analysis demonstrated that both SNPs were associated with marbling (P=0.0153 for A/C and P=0.0026 for C/T) and SFD (P=0.0200 for A/C and P=0.0039 for C/T), respectively. A search for transcriptional regulatory elements using Mat-Inspector indicated that both SNPs lead to a gain/loss of six putative binding sites for genes relevant to fat deposition and energy metabolism. Compared with previous reports on thyroglobulin, leptin and diacylglycerol O-acyltransferase genes, the TFAM gene had the greatest effects on both marbling and SFD in this population, indicating its potential as a new target for marker-assisted selection in the beef industry.

Mitochondrial transcription factor A (TFAM), a member of a high mobility group protein family and the first-identified mitochondrial transcription factor (Fisher and Clayton, 1988), is essential for maintenance and biogenesis of mtDNA. First, TFAM plays a histone-like role in mitochondria, as it is tightly associated with mtDNA as a main component of the nucleoid (Kanki et al., 2004a). Evidence has shown that one molecule of mtDNA is packed with ~900 molecules of TFAM on average (Alam et al., 2003), which makes mtDNA no longer naked. Second, TFAM regulates mtDNA copy number in mammals. Investigation using a combination of mice with TFAM overexpression and TFAM knockout demonstrated that mtDNA copy number is directly proportional to the total TFAM protein level in mouse embryos (Ekstrand et al., 2004). RNA interference of the endogenous TFAM expression in HeLa cells also indicated that the mtDNA amount is correlated in parallel with the amount of TFAM (Kanki et al., 2004b). Third, TFAM stimulates transcription of mtDNA. The TFAM protein possesses two tandem high mobility group domains, which makes TFAM bind, unwind and bend DNA without sequence specificity and thus facilitate transcription initiation of mtDNA (Gaspari et al., 2004). Evidence has shown that import of wt-TFAM into liver mitochondria from hypothyroid rats increased RNA synthesis significantly up to 4-fold (Garstka et al., 2003).

It has been known for many years that adipose tissue plays a central rule in regulation and manipulation of energy metabolisms through the storage and turnover of triglycerides and through the secretion of factors that affect satiety and fuel utilization. However, many key aspects of adipogenesis are accompanied by stimulation of mitochondrial biogenesis (Wilson-Fritch et al., 2003). For example, the major site of fatty acid β-oxidation occurs in mitochondria (Reichert and Neupert, 2004), which may provide key intermediates for the synthesis of triglycerides via the action of pyruvate carboxylase (Owen et al., 2002). In addition, a relatively large mitochondrial mass are needed to generate acetyl-CoA for fatty acid activation prior to esterification into triglycerides. All these studies demonstrated the essential role and function of mitochondria in lipid metabolism.

To further explore the mechanism of mitochondria involved in adipogenesis, Wilson-Fritch and colleagues (2003 and 2004) studied the 3T3-L1 cell (representative of white adipocytes) differentiation by using both proteomic and genomic approaches. Proteomic analysis revealed a 20- to 30-fold increase in the concentration of numerous mitochondrial proteins, while genomic analysis with gene expression profiling using Affymetrix GeneChips detected a statistically significant increase in the expression of many nucleus-encoded mitochondrial genes during adipogenesis. In particular, the authors found a profound decrease of approximately 50% in the levels of transcripts for nuclear-encoded mitochondrial genes accompanying the onset of obesity (Wilson-Fritch et al., 2004). As TFAM is one of the nuclear-encoded mitochondrial genes, it was hypothesized that it plays an important role in lipogenesis or fat deposition via its role in mitochondrial biogenesis. Here, evidence is presented to support the hypothesis by reporting significant associations of bovine TFAM promoter polymorphisms with marbling scores and SFD measurements in Waygu x Limousin crossbreds.

A $F_1$ generation of a Wagyu x Limousin cross was developed at Washington State University and transferred to the Fort Keogh Livestock and Range Research Laboratory, ARS, USDA in the autumn of 1998, including 6 $F_1$ bulls and 113 dams. Inter se mating of these $F_1$ animals produced 71 $F_2$ progeny in 2000, 90 in 2001 and 109 in 2003, respectively. Each calf was weighed within 24 h after birth and again at weaning when the calves averaged approximately 180 d of age. After weaning, the calves were returned to native range pastures and were supplemented with 0.7 kg per calf per day of both barley cake and alfalfa pellets. In mid-January, the calves were moved from the range and were fed silage and chopped hay to achieve anticipated gains of 0.5 to 0.8 kg per day. They were then placed on finishing diet for approximately 150 days followed by slaughter. Growth rate and carcass and meat quality data were collected on all $F_2$ calves. Marbling scores varied from 4=Slight$^0$ to 9.5=Moderately Abundant$^{50}$ (SD=1.00) and SFD measurements ranged from 0.1 to 1.3 inches (SD=0.18) in this $F_2$ population. Marbling was a subjective measure of the amount of intramuscular fat in the longissimus muscle based on USDA standards (http://www.ams.usda.gov/). SFD was measured at the 12-13$^{th}$ rib interface perpendicular to the outside surface at a point three-fourths the length of the longissimus muscle from its chine bone end. DNA was extracted from blood samples. Based on the availability of both data and DNA samples, 246 observations were used in the current study.

Figure 1:
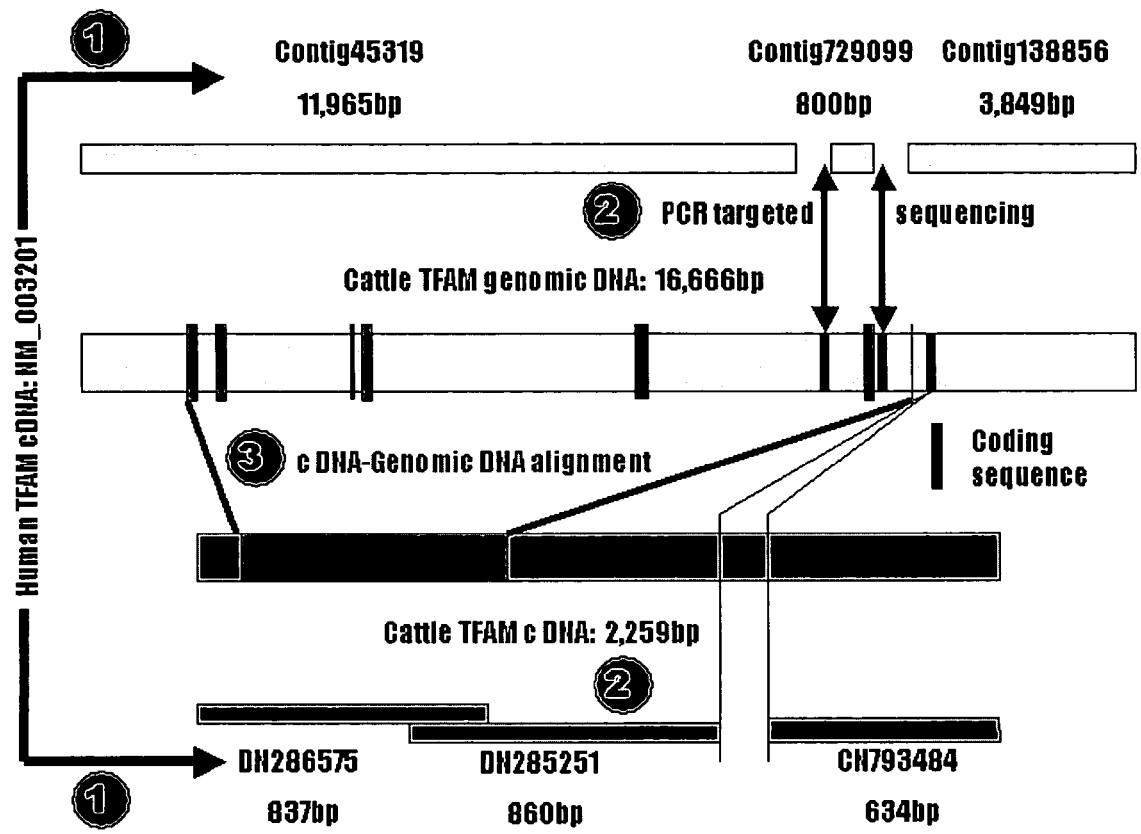
FIG. 1 provides a schematic annotation of cDNA and genomic DNA sequences of the bovine TFAM gene using a combination of in silico approach with PCR target region amplification.

Unfortunately, both cDNA and genomic DNA sequences were not available for the bovine TFAM gene when the project was started. However, the bovine genome mapping project has advanced significantly in recent years. In particular, more than 500,000 bovine ESTs (expressed sequence tags) (http://www.ncbi.nlm.nih.gov/) and 3x bovine genome sequences (http://www.hgsc.bcm.tmc.edu/projects/bovine/) have been released to the public databases. Therefore, a combination of an in silico comparative cloning with a PCR target cloning approach was developed and used to determine both cDNA and genomic DNA sequences of the bovine gene (FIG. 1). The procedure included three steps: 1), BLAST searches against the public databases using a full-length cDNA sequence of the human TFAM gene as a reference to retrieve all bovine sequences that are orthologous to the human gene; 2), annotation of both ESTs and genomic DNA sequences in order to design primers for the target region amplification to close gaps if there are any; and 3); alignment of cDNA sequences and genomic DNA sequences to determine the full-length cDNA sequence and genomic organization of the bovine TFAM gene.

Two pairs of primers were designed to close two gaps for the genomic DNA sequence of the bovine TFAM gene (Table 1). PCR reactions were performed using 25 ng of bovine genomic DNA as template in a final volume of 10 μL containing 12.5 ng of each primer, 200 μM dNTPs, 1.5-3 mM MgCl$_2$, 50 mM KCl, 20 mM Tris-HCl and 0.2 U of Platinum Taq polymerase (Invitrogen, Carlsbad, Calif.). The PCR conditions were carried out as follows: 94° C. for 2 min, 32 cycles of 94° C. for 30 sec, 63° C. for 30 sec and 72° C. for 30 sec, followed by a further 5 min extension at 72° C. PCR products were then examined by electrophoresis through a 1.5% agarose gel with 1xTBE buffer to determine the quality and quantity for DNA sequencing. Sequencing was performed on ABI 3730 sequencer in the Laboratory for Biotechnology and Bioanalysis (Washington State University). Sequences of these two PCR-amplified products spanning the gap regions and three contigs of genome sequences derived from the cattle genome sequence project were then assembled to form a complete genomic DNA sequence for the bovine TFAM gene.

TABLE 1

Primers designed for genomic gap closing and mutation detection in the bovine TFAM gene.

| Target region | Primer sequences (5'-3') | Size in bp | Annealing Tm | SEQ ID NO: |
|---|---|---|---|---|
| Promoter | Forward: GTTGTTGCAGAAATCAGCTAAAATG | 801 | 61° C. | 4 |
|  | Reverse: CATCCACTGAGACTATCGCTGACCT |  |  | 5 |
| Exon 1 | Forward: CGCCTCCTAGCTAATCGGAAGTTAG | 405 | 61° C. | 6 |
|  | Reverse: |  |  |  |

TABLE 1-continued

Primers designed for genomic gap closing and mutation detection in the bovine TFAM gene.

| Target region | Primer sequences (5'-3') | Size in bp | Annealing Tm | SEQ ID NO: |
|---|---|---|---|---|
| | GTCGGAATCACAGGGCTAAGTCAGG | | | 7 |
| Exon 2 | Forward: TTCCCCTGGATAGGACAGGATTTTA | 421 | 61° C. | 8 |
| | Reverse: TACAGGCCATCACACAGAATGGTTA | | | 9 |
| Exon 3 | Forward: GAGCTAATGGATTATTCTTTCCTGA | 407 | 57° C. | 10 |
| | Reverse: ATGTGTTATCCAAGGTGAAGGTCTA | | | 11 |
| Exon 4 | Forward: TTATAAGTGGGATTTCAGAGTGCAT | 459 | 57° C. | 12 |
| | Reverse: AACTGAAGTCATTCTCTACCACGTC | | | 13 |
| Exon 5 | Forward: AACAATCGCATACTCATAATGTTCA | 392 | 57° C. | 14 |
| | Reverse: TGGTAAGAAAAGGATTTTTAGGTC | | | 15 |
| Intron 5 gap | Forward: GCACAAACAAAGGAACCATCAA | 222 | 57° C. | 16 |
| | Reverse: TTCCCTGACAATGATGTTGAGC | | | 17 |
| Exon 6 | Forward: TACAGCTCAGAGTTTTGAGGAGTCT | 408 | 57° C. | 18 |
| | Reverse: CACTAAGTTACGAGGGACACTGTTT | | | 19 |
| Intron 6 gap & Exon 7 | Forward: TGAAAACTGGAAAAATCTCTCTA | 736 | 57° C. | 20 |
| | Reverse: AACAGCTTCCGGTATTGAGACCT | | | 21 |

Primers were designed to target the promoter region and all coding regions in order to screen genetic polymorphisms in the bovine TFAM gene (Table 1). Four DNA pools were formed, one from all six $F_1$ bulls, one from 30 randomly selected $F_1$ dams, one from 30 $F_2$ high marbling progeny and one from 30 $F_2$ low marbling progeny. PCR products for each pair of primers were amplified on these four DNA pools and directly sequenced on ABI 3730 sequencer as described above. Nucleotide polymorphisms were identified by comparison of sequence patterns among these four DNA pools. Unfortunately, no polymorphisms were detected in the coding sequences, but two SNPs, i.e., C/A substitution and C/T substitution were found in the bovine TFAM promoter region.

These two SNPs in the bovine promoter region were then genotyped in Wagyu X Limousin $F_2$ animals that have both DNA samples and performance data for marbling score and SFD measurements. Using the PCR-RFLP (restriction fragment length polymorphism) approach, these two mutations were revealed by digestion at 37° C. for three hours of PCR amplicons with 2 U of HaeIII for the C/A substitution and 2 U of DpnI for the C/T substitution, followed by analysis on 4% agarose gels. The phenotypic data for marbling scores and SFD measurements were adjusted for effects of year, gender, and age at harvest (linear) before assessing the effects of the genotypes using the GLM (general linear model) procedure of SAS v9.1 (SAS institute Inc., Gary, N.C.) to assess the effects of contemporary group and genotype at the TFAM gene locus.

The BLAST searches using the human TFAM cDNA (NM_003201) as a reference retrieved eight bovine orthologous EST sequences from the ESTs_others database at National Center for Biotechnology Informatics (NCBI) and three genomic contigs from the cattle 3× genome assembly at Baylor College Medicine. Three ESTs (DN286575, DN285251 and CN793484) were chosen to form an initial consensus cDNA sequence of the bovine TFAM gene, but they left a gap in the 3'UTR (untranslated region) (FIG. 1). However, initial alignment of these EST sequences with the genomic DNA sequence revealed that the cDNA sequence gap could be easily closed using the genomic DNA sequence corresponding to the 3'UTR region. The total length of the assembled mRNA sequence is 2,259 bp for the bovine TFAM gene. Three genomic DNA contigs (contig45319, contig729099 and contig138856) apparently had no overlap. Orientating these three genomic contigs to a 5'-3' direction corresponding to the mRNA sequence made it possible to design primers to close two gaps among them (FIG. 1). Two PCR products of 222 bp and 736 bp (Table 1) were amplified and sequenced. Assembling of the three genomic contigs and these two PCR products made it possible to form a 16,666 bp genomic DNA sequence for the bovine TFAM gene (FIG. 1).

All eight bovine ESTs that are orthologous to the human TFAM gene are 99-100% identical to the assembled consensus mRNA sequence. The putative complete coding sequence of the bovine TFAM gene is 741 bp in length, which is identical to that in human (NM_003201, D'Errico et al., Gene 362, 125-132 (2005)), but 6 bp and 9 bp longer than that in rat (NM_031326, Piantadosi and Suliman, J. Biol. Chem. 281 (1), 324-333 (2006)) and mouse (NM_009360, Noack et al., Biochim. Biophys. Acta 1760 (2), 141-150 (2006)), and 48 bp shorter than that in chicken (NM_204100, Caldwell et al., Genome Biol. 6 (1), R6 (2005)), respectively. The translated amino acid sequence encoded by the bovine TFAM gene showed 91% identity with pig (AY923074), 71% with human (NM_003201), 65% with rat (NM_031326), 63% with mouse (NM_009360), and 43% with chicken (NM_204100), respectively. The overall structure of the bovine TFAM gene was determined by comparing the genomic DNA sequence with the complete cDNA sequence determined in the study (FIG. 1). Like that in human, mouse, rat and chicken, the genomic organization of the bovine TFAM gene consists of seven exons and six introns (FIG. 1).

It is estimated that the bovine genome is similar in size to the genomes of humans and other mammals, containing approximately 3 billion DNA base pairs. Sequencing of the bovine genome began in December 2003 and the initial assembly based on 3.3-fold coverage of the bovine genome was released on Oct. 6, 2004, which can now be accessed through GenBank (www.ncbi.nih.gov/Genbank) at NCBI. In addition, more than 500,000 bovine ESTs have also been released to the public and can be accessed through GenBank at NCBI. Both bovine ESTs and genome sequences provide us valuable resources to revolutionize genome research in cattle. In the current study, a tool that combines an in silico comparative cloning with a PCR target cloning approach was developed and used to clone both cDNA and genomic DNA sequences of the bovine TFAM gene. This approach is very straightforward, simple, fast and inexpensive. Therefore, this approach may serve as one of the model tools in identifying, mapping, and understanding the function of genes in cattle, which will further advance basic biology research.

FIG. 2 shows the nucleotide sequences for the 5'-up-stream region and the entire exon 1 of the bovine TFAM gene. Analysis using MatInspector program (Quandt et al., 1995) revealed one potential nuclear respiratory factor 1 (NRF1) and one stimulating protein 1 (SP1) binding site in the bovine TFAM promoter region (FIG. 2). However, the bovine TFAM promoter lacks the putative binding sites for nuclear respiratory factor 2 (NRF2). In the human TFAM promoter region, both NRF1 and NRF2 binding sites were found, while only NRF2 binding sites existed in the rat and mouse TFAM promoters (Scarpulla, 2002). All TFAM promoters in human, rat and mouse have the SP1 binding sites. NRF1, NRF2 and SP1 are the most prevalent factors associated with respiratory genes (Scarpulla, 2002). In addition to the NRF1 and SP1 binding sites, the bovine TFAM promoter contains a provisional transcriptional repressor binding site, which binds to elements found predominantly in genes that participate in lipid metabolism (FIG. 2). Although it is unclear whether the CpG islands are methylated in vivo, many potential methylated CpG loci are present in the bovine TFAM promoter (FIG. 2).

Very interestingly, the bovine TFAM promoter may be one of the few promoters that contain naturally occurring AUG codon upstream from the normal translational start site (FIG. 2). This extra AUG codon was also confirmed by sequencing with primers spanning partial promoter, entire exon 1 and partial intron 1 (see description below) in the study. The Kozak's general rule is that in most cases the AUG codon nearest the 5'end is the unique site of initiation of translation, because this "position effect" is seen in cases where a mutation creates an AUG codon upstream from the normal start site and translation shifts to the upstream site (Kozak, 2002). However, this first rule can be ruled out when the 5' proximal AUG triplet is followed shortly by a terminator codon, which makes the reinitiation at a downstream AUG codon possible (Kozak, 1995). It is observed that this extra AUG codon in the bovine TFAM promoter is not in frame (FIG. 2). If it did translate, it would just generate a peptide of 12 amino acids as MQWRFSGAYGAC (SEQ ID NO: 22). Whether and how this 5' proximal AUG triplet interferes with normal translation remains unknown. Therefore, the bovine TFAM gene could be a natural model gene for investigation of mechanisms involved in translation initiation of mammalian genes.

A total of eight pairs of primers were designed and used to screen genetic polymorphisms in the bovine TFAM gene. One pair of primers targets the promoter region, and the remaining primers amplify seven exons with a pair of primers per exon. However, the last pair of primers was used for both gap closing and exon 7 amplification (Table 1). In order to have each exon region completely amplified and sequenced, at least 100 bp of sequences from each flanking side were included in the products. No polymorphisms were found in all coding sequences of the bovine TFAM gene, even though the reference population includes two divergently bred breeds of cattle: an Asian origin Wagyu and a European origin Limousin, which have characteristics that are quite different from each other. However, two SNPs were detected in the promoter region (FIG. 2 and FIG. 3). These two SNPs are located just 9 bp apart, one C/A substitution and another C/T substitution. Both SNPs were revealed by digestion with HaeIII and DpnII, respectively on a fragment of 801 bp (FIG. 4).

As the fragment possesses three HaeIII restriction sites, digestion yields two invariable bands of 152 bp and 462 bp, and one 187 bp band, which can be, depending on the nucleotide at position −1220 (FIG. 2), further cleaved in two 83 bp and 104 bp bands (FIG. 4). Therefore, homozygous animals with A allele have two HaeIII sites, and reveal after complete digestion three bands: 152 bp, 187 bp and 462 bp, homozygous animals with C allele have gained an additional HaeIII site at this position and result in four bands (83 bp, 104 bp, 152 bp and 462 bp) after complete digestion. However, heterozygous animals showed five bands after HaeIII digestion (FIG. 4). These two common HaeIII sites were considered as internal controls of the enzyme digestion.

In comparison, the fragment contains four DpnII restriction sites, including one polymorphic site. Therefore, digestion with DpnII yields three invariable bands of 55 bp, 68 bp and 135 bp, and three polymorphic bands of 241 bp, 302 bp and 543 bp, respectively (FIG. 4). Homozygous animals with T allele have all four DpnII sites, and reveal after complete digestion five bands: 55 bp, 68 bp, 135 bp, 241 bp and 302 bp, while homozygous animals with C allele have lost a DpnII site at position −1212 (FIG. 2) and result in four bands (55 bp, 68 bp, 135 bp and 543 bp) after complete digestion. However, heterozygous animals showed six bands after DpnII digestion (FIG. 4). These three common DpnII sites also served as internal controls of the enzyme digestion.

Genotyping 237 $F_2$ animals for both C/A and C/T SNPs, revealed 75 homozygous CC animals, 45 homozygous AA and 117 heterozygous CA animals for the former SNP and 84 homozygous CC animals, 33 homozygous TT and 120 heterozygous CT animals for the latter SNP (Table 2). For C/A substitution, the frequencies of allele C and allele A in the population were 0.56 and 0.44, respectively. The frequency of allele C slightly increased to 0.61 for the C/T substitution. However, both genotype distributions were in Hardy-Weinberg equilibrium.

General linear model analysis clearly indicated that the effect of genotype at either SNP reached statistical significance (for C/A substitution, P=0.0019 for marbling score and P=0.0200 for SFD measurement; and for C/T substitution, P=0.0011 for marbling score and P=0.0039 for SFD measurement) (Table 2). For C/A substitution, the cattle with the homozygote (CC) genotype had an additional 0.047 inches of subcutaneous fat and 0.482 score of marbling compared to the AA homozygotes (P<0.05). However, the differences between two homozygotes CC and TT were further enlarged for the C/T substitution. Subcutaneous fat thickness was 0.073 inches thicker and marbling score was 0.634 higher in cattle with the homozygote (CC) genotype than the TT homozygotes (P<0.05) (Table 2).

Only five haplotypes between these two promoter polymorphisms were observed in 237 Wagyu x Limousin $F_2$ animals, including 75 CCCC, 108 CACT, 33 AATT, 12 AACT and 9 CACC, respectively. Due to relatively few samples, both haplotypes AACT and CACC were excluded in further statistical analysis. As indicated in Table 2, haplotype had significant effects on both marbling and SFD in the reference population (P=0.0004 for marbling and P=0.0029 for SFD). Marbling score was 0.655 different between CCCC and AATT animals and 0.518 different between CCCC and CACT animals (P<0.05). For SFD measurements, the cattle with CCCC haplotype had an additional 0.079 and 0.073 inches of subcutaneous fat compared to the CACT and AATT animals (P<0.05), respectively. The CCCC haplotype seems to be associated with an increase of the whole body fat deposition in cattle.

TABLE 2

Associations of the bovine TFAM promoter SNPs with marbling and SFD in Waygu x Limousin $F_2$ crosses*.

| SNP | Genotype | No. of animals | Marbling (score) Mean ± S.E. | P value | SFD (in inch) Mean ± S.E. | P value |
|---|---|---|---|---|---|---|
| C/A | CC | 75 | 6.245 ± 0.115[a] | 0.0019 | 0.441 ± 0.018[a] | 0.0200 |
|  | CA | 117 | 5.748 ± 0.094[b] |  | 0.376 ± 0.015[b] |  |
|  | AA | 45 | 5.763 ± 0.147[b] |  | 0.394 ± 0.023[b] |  |
| C/T | CC | 84 | 6.220 ± 0.108[a] | 0.0011 | 0.447 ± 0.017[a] | 0.0039 |
|  | CT | 120 | 5.822 ± 0.091[b] |  | 0.375 ± 0.015[b] |  |
|  | TT | 33 | 5.586 ± 0.172[b] |  | 0.374 ± 0.027[b] |  |
| Both | CCCC | 75 | 6.250 ± 0.113[a] | 0.0004 | 0.444 ± 0.018[a] | 0.0029 |
|  | CACT | 108 | 5.732 ± 0.097[b] |  | 0.365 ± 0.015[b] |  |
|  | AATT | 33 | 5.595 ± 0171[b] |  | 0.371 ± 0.027[b] |  |

*Means within a column with different superscripts are significantly different (P < 0.05).

Previous efforts have identified candidate genes responsible for marbling and/or SFD in beef. Barendse and colleagues (1997) identified a TG5 polymorphism that occurs in the 5' promoter region of the thyroglobulin (TG) gene. This marker had a genotypic association with marbling score in long-fed cattle. Leptin is a 16-kilodalton protein produced by the obesity (ob) gene. Mutations in the leptin (LEP) gene cause beef cattle to reach slaughter weight sooner and develop more marbling in the carcass (Buchanan et al., 2002). A nonconservative K232A substitution in the DGAT1 (diacylglycerol O-acyltransferase) gene has been shown to affect intramuscular fat deposition (marbling) in beef (Thaller et al. 2003). Genotyping a C/T SNP in the TG gene, a C/T mutation in the LEP gene and an A/C polymorphism in the DGAT1 gene were also performed in this Waygu x Limousin cross population (De et al., 2004 and Wu et al., 2005, in press). Analysis of variance using a generalized linear model did not show any significant differences among genotypes in LEP gene. However, the DGAT1 gene had a significant additive effect on SFD (P=0.036), while the TG gene showed a dominant effect on marbling that approached significance (P=0.061).

De and colleagues (2004) observed that in the TG gene, the genotype differences between homozygotes CC and TT were −0.074±0.093 score for marbling and −0.002±0.015 inches for SFD (P>0.05 for both traits), while in the DGAT1 gene, AA homozygous animals were superior to CC homozygous animals by 0.092±0.095 score for marbling (P>0.05) and 0.032±0.015 inches for SFD (P<0.05), respectively. In the LEP gene, the same FIGs for genotype differences between CC and TT animals were 0.075±0.116 score for marbling and 0.019±0.018 inches for SFD (P>0.05 for both traits), respectively. Obviously, the current study on the bovine TFAM gene indicated that the genotype differences between two homozygotes at either position exceeded any differences observed in the bovine TG, DGAT1 and LEP gene, respectively. In particular, the genotype differences between homozygotes CC and TT in the bovine TFAM gene accounted for 0.634 standard deviation in marbling and 0.402 standard deviation in SFD as this Wagyu X Limousin $F_2$ animals had a standard deviation of 1 score for marbling and a standard deviation of 0.18 inches for SFD. Therefore, among these four candidate genes studied so far in the reference population, the results showed that the TFAM gene had the greatest effects on both marbling and SFD, indicating a major gene for both traits.

A search for transcriptional regulatory elements using MatInspector (http://www.gsf.de/) indicated that both SNPs in the bovine TFAM promoter jointly or separately lead to a gain/loss of six putative binding sites for 1), tal-1alpha/E47 heterodimer; 2), cAMP-responsive element binding protein 1; 3), heterodimers of the bHLH transcription factors HAND2 (Thing2) and E12; 4), nuclear factor 1; 5), RAR-related orphan receptor alpha1 and 6), Zinc finger protein RP58 (ZNF238), which is associated preferentially with heterochromatin. Reusch and Klemm (2002) reported that the transcription factor cAMP-response element-binding protein (CREB) participates in adipogenesis, with constitutively active forms of CREB inducing adipocyte differentiation and dominant negative forms of CREB blocking this process. Evidence has shown that nuclear factor 1 is essential for the expression of stearoyl-CoA desaturase 1 gene during preadipocyte differentiation (Singh and Ntambi, 1998). The RAR-related orphan receptor alpha1, or RORα1 forms a part of the multifactoral regulatory mechanisms that control expression of the PPARgamma gene, which has been extensively studied for the past decade mainly due to its central role in promoting and maintaining the adipocyte phenotype (Sundvold and Lien, 2001). However, how these two SNPs in the bovine TFAM promoter affect binding efficiency for these genes, how these binding alterations regulate the subsequent TFAM gene expression patterns and how these expression patterns stimulate mitochondrial biogenesis differently and thus lead to the differences in fat deposition and energy metabolisms, need to be further explored.

REFERENCES

Alam et al. Nucleic Acids Res. 2003; 31:1640-5.
Barendse, 1997. Patent Application WO9923248 PCT/AU98/00882.
Buchanan et al. Genet Sel Evol. 2002; 34:105-16.
De et al. Proceedings, Western Section, American Society of Animal Science. 2004; 55:95-98.
Ekstrand et al. Hum Mol Genet. 2004; 13:935-44.
Fisher and Clayton, Mol Cell Biol. 1988; 8:3496-509.
Garstka et al. Nucleic Acids Res. 2003; 31:5039-47.
Gaspari et al. 2004; 1659:148-52.
Kanki et al. Mol Cell Biol. 2004; 24:9823-34.
Kanki et al. Ann N Y Acad Sci. 2004; 1011:61-8.
Kozak, Proc Natl Acad Sci USA. 1995; 92:2662-6.
Kozak, Gene. 2002; 299:1-34.
Owen et al. J Biol Chem. 2002; 277:30409-12.
Quandt et al. Nucleic Acids Res. 1995; 23:4878-84.
Reichert and Neupert, Trends Genet. 2004; 20:555-62.
Reusch and Klemm, 2002, J Biol Chem. 277, 1426-1432.
Savell et al. (1986) Journal of Food Science 51, 838.
Scarpulla, 2002. Biochim. Biophys. Acta. 1576: 1-14.

Singh and Ntambi, 1998. Biochim Biophys Acta. 1398, 148-156.
Sundvold and Lien, 2001. Biochem Biophys Res Commun. 287, 383-390.
Thaller et al. Anim Genet. 2003 October; 34(5):354-7
Wilson-Fritch et al. Mol Cell Biol. 2003; 23:1085-94.
Wilson-Fritch et al. J Clin Invest. 2004; 114:1281-9.
Wu et al. Genetica. 2005 September; 125(1):103-13.

Example 2

This Example describes basal nucleus-encoded mitochondrial transcription genes and meat quality in beef cattle.

Evidence has shown that the basal mitochondrial transcription machinery directs the mitochondrial biogenesis and gene expression, and thus it may play an important role in body fat deposition and energy metabolism. Here we report sequence compilation, genetic marker development and association analysis of TFAM, TFB1M and TFB2M genes with marbling and subcutaneous fat depth (SFD) in cattle using a reference population of Wagyu x Limousin $F_2$ crosses. Statistical analysis revealed that the bovine TFAM gene was significantly associated with marbling (F=3.84, P=0.0229) and SFD (F=3.56, P=0.0301). The genetic markers developed in the study can be used to further determine how this mitochondrial complex is important to improve meat quality in the beef industry.

Due to its limited protein coding capacity, the initiation and regulation of gene expression in mitochondrial DNA (mtDNA) rely heavily on a relatively small set of nuclear encoded mitochondrial regulatory proteins (Gleyzer et al., 2005). The basic mitochondrial transcription machinery consists of mitochondrial RNA polymerase (POLRMT) and mitochondrial transcription factor A (TFAM), B1 (TFB1M) and B2 (TFB2M). TFAM, a member of a high mobility protein family group and the first-identified mitochondrial transcription factor, is essential for maintenance and biogenesis of mtDNA (Fisher and Clayton, 1988). Both TFB1M and TFB2M are newly identified mitochondrial transcription factors and they interact directly with POLRMT to form a heterodimer (Falkenberg et al., 2002). On the other hand, mitochondria perform a large number of reactions in eukaryotic cells, including the β-oxidation of fatty acids, which provides key intermediates for the synthesis of triglycerides via the action of pyruvate carboxylase (Owen et al., 2002). As the basic mitochondrial transcription machinery directs the mitochondrial biogenesis and gene expression, it has been envisaged that the machinery may play an important role in body fat deposition and energy metabolism. Here sequence compilation, genetic marker development and association analysis of TFAM TFB1M and TFB2M genes with marbling and subcutaneous fat depth (SFD) using a reference population of Wagyu x Limousin $F_2$ crosses are reported.

The bioinformatics procedures used for retrieving both cDNA and genomic DNA sequences of these three bovine genes employed a three-step approach. First, cDNA sequences of the human orthologs were used as references to retrieve the orthologous ESTs against the GenBank database "est_others" with a species option limited to *Bos taurus*. Second, several ESTs were chosen and assembled to form a primary cDNA sequence for each cattle gene, which was then used to perform a species-specific ESTs search against the same database in order to expand the primary sequence to a full-length cDNA sequence. Finally, the full-length cDNA sequence was used to search for genomic DNA sequences of the same gene against the 6x bovine genome sequence database and thus determine its genomic organization.

Primers were designed to target promoter regions and all coding exons for all three bovine genes based on the genomic DNA sequences. To ensure each exon region was completely amplified and sequenced, at least 100 bp of flanking sequences were included in the products. To facilitate discovery of genetic polymorphisms in these genes, two DNA pools were formed: one from 6 Wagyu x Limousin $F_1$ sires and one from 113 Wagyu x Limousin $F_1$ dams. PCR reactions were performed on these two DNA pools and sequenced on an ABI 3730 sequencer in the Laboratory for Biotechnology and Bioanalysis (Washington State University) using a standard protocol. Nucleotide polymorphisms were identified by comparison of sequence patterns between these DNA pools. A total of ten single nucleotide polymorphisms (SNPs) were detected, including 3 in TFAM, 2 in TFB1M and 5 in TFB2M gene.

Only one SNP in TFAM, two SNPs in TFB1M and one SNP in the bovine TFB2M gene were chosen for genotyping using PCR-RFLP and Bi-PASA techniques. Animals used in the study were $F_2$ progeny from inter se mating of 6 Wagyu x Limousin $F_1$ sires and 113 Wagyu x Limousin $F_1$ dams as described above. Marbling scores varied from 4=Slight$^0$ to 9.5=Moderately Abundant$^{50}$ (SD=1.00). SFD was measured at the 12-13$^{th}$ rib interface perpendicular to the outside surface at a point three-fourths the length of the longissimus muscle from its chine bone end, which ranged from 0.1 to 1.3 inches (SD=0.18) in this $F_2$ population. The phenotypic data for marbling scores and SFD were analyzed with a mixed linear model using the PROC MIXED module in SAS v9.1. Source of variation included year of birth, gender, age at harvest and genotype of each gene marker as fixed effects and a random effect to account for polygene background. The covariance structure of the polygene effect was defined by a numerical relationship calculated from pedigree using SAS macro LORG. The residual effect was assumed to have identical independent distribution with unknown variance. The additive genetic variance and residual variance components were estimated using the ridge stabilized Newton-Raphson algorithm for restricted maximum likelihood (REML) estimation. Tests of marker effects were performed using the Kenward-Roger method for calculating denominator degrees of freedom. This method uses an adjusted estimator of covariance matrix to reduce small sample bias. Pair-wise comparisons of least-squares means were performed using Fisher's protected least significant difference (LSD) t-test procedure.

The human ortholog-based BLAST search retrieved more than 20 ESTs for each of the bovine TFAM, TFB1M and TFB2M from the GenBank "est_others" database. Several overlapping ESTs were chosen and assembled to form primary cDNA sequences for these genes. The primary cDNA sequence was then used as a reference to search for ESTs of the same gene, in particular for its 5' and 3' flanking sequence expansion, which were missed by the human ortholog search due to low sequence similarity in these regions. The final assembly produced a full-length cDNA sequence of 2,259 bp for the bovine TFAM gene, 2,617 bp for the bovine TFB1M gene and 1,991 bp for the bovine TFB2M gene, respectively. Using these full-length cDNA sequences as references, BLAST searches against the 6x cattle genome sequence database retrieved three genomic contigs of 16,666 bp for TFAM, four genomic contigs of 108,966 bp for TFB1M and one genomic contig of 53,542 bp for TFB2M, respectively. Like in human, dog, mouse and rat, both bovine TFAM and TFB1M genes consist of seven exons, while the bovine TFB2M contain eight exons.

In addition to two closely linked A/C and C/T SNPs described in Example 1, a third mutation with a C/T transition was also detected in the bovine TFAM promoter region (FIG. 5A). A Bi-PASA assay was developed to genotype this marker on individuals. Direct sequencing of PCR products on two DNA pools revealed two mutations in the TFB1M gene (FIG. 5B) and five mutations in the TFB2M gene (FIG. 5C), respectively. The PCR amplicons were digested with 2 U of MspI and BanI for genotyping SNPs of T/G and G/C in the bovine TFB1M gene. Initial genotyping of 48 samples using three of the five polymorphisms in the bovine TFB2M gene revealed they are fixed in two haplotypes. Therefore, only one SNP was chosen for genotyping by digestion with restriction enzyme AciI.

Statistical analysis revealed that the bovine TFAM gene was significantly associated with marbling (F=3.84, P=0.0229) and SFD (F=3.56, P=0.0301). However, none of the markers in either TFB1M and TFB2M affected the measured traits significantly (F<1.70, P>0.1842). The additive and dominance effects of each marker were estimated and are listed in Table 3. Only the additive effect of the bovine TFAM gene on marbling reached a significant level (P=0.0059) and the additive effects of the TFAM and TFB2M on SFD approached significance (P=0.0651 for TFAM and P=0.1118 for TFB2M) (Table 3). The results indicate that involvement of these three genes in promoting transcription initiation of the mitochondrial genome may be tissue-specific or relevant. That is, TFAM contributed significantly to both marbling and SFD, while TFB1M had no effect on either trait. However, TFB2M contributed more to SFD, but almost nothing to marbling.

Example 3

This Example provides associations between TFAM-1, TFAM-2, and FABP4 markers and carcass traits in commercial feedlot steers and heifers.

The following markers were evaluated: (1) a C to A substitution at the 1220 nucleotide position in the mitochondrial transcription factor A gene (TFAM-1) promoter, (2) a C to T substitution at the 1212 nucleotide position in the TFAM-2 promoter and (3) a G to C substitution at the 7516 nucleotide position of the fatty acid binding protein 4 gene (FABP4). Previous results indicate that the markers affect Markers affect marbling and backfat.

Initially, there were 1,589 records initially from steers and heifers. The target endpoint was 12.2 mm backfat. Harvest date was predicted optimal economic endpoint by animal. Contemporary groups included source and sex. It was assumed that the breed type confounded with the source. The final data set included the number of records based on available phenotypes and genotypes for each trait.

The tested traits are: hot carcass weight (HCW, lb), ribeye area (REA, in$^2$), ribeye area per hundred weight HCW (REA/cwt HCW, in$^2$/100 lb hot carcass weight (HCW), hot carcass weight value (HCW value, $), calculated live weight (Calc Lv Wt, lb), dry matter intake (DMI, lb), days on feed (DOF, d), dry matter intake per day on feed (DMI per DOF, lb/d), average daily gain (ADG, lb/d), dressing percentage (DP, %), backfat thickness (BFAT, in), calculated yield grade (cYG), quality grade, less than or equal to select versus greater than

TABLE 3

Additive and dominance effects of the bovine TFAM, TFB1M and TFB2M markers on marbling and SFD.

| Genetic effect | Marbling | | | SFD (in inches) | | |
|---|---|---|---|---|---|---|
| | Estimate ± S.E. | t | Pr > \|t\| | Estimate ± S.E. | t | Pr > \|t\| |
| C/T in the bovine TFAM gene | | | | | | |
| Additive | −0.384 ± 0.138 | −2.78 | 0.0059 | −0.036 ± 0.019 | −1.85 | 0.0651 |
| Dominance | 0.117 ± 0.088 | 1.27 | 0.2066 | −0.007 ± 0.013 | −0.56 | 0.5780 |
| G/T in the bovine TFB1M gene | | | | | | |
| Additive | −0.206 ± 0.160 | −1.28 | 0.2003 | −0.007 ± 0.022 | −0.33 | 0.7451 |
| Dominance | −0.017 ± 0.100 | 0.17 | 0.8646 | −0.003 ± 0.014 | −0.23 | 0.8209 |
| C/G in the bovine TFB1M gene | | | | | | |
| Additive | 0.017 ± 0.186 | 0.09 | 0.9273 | −0.005 ± 0.026 | −0.19 | 0.8528 |
| Dominance | 0.074 ± 0.118 | 0.63 | 0.5288 | −0.023 ± 0.017 | 1.41 | 0.1612 |
| C/T in the bovine TFB2M gene | | | | | | |
| Additive | 0.121 ± 0.120 | 1.00 | 0.3188 | −0.028 ± 0.018 | 1.60 | 0.1118 |
| Dominance | −0.112 ± 0.079 | −1.41 | 0.1588 | −0.000 ± 0.011 | −0.03 | 0.9798 |

Both marbling and SFD have attracted a great deal of publicity and interest for many years, since they are two of the major quantitative traits that affect carcass quality and production efficiency in beef cattle. The genetic markers developed in the study can be used to further determine how this mitochondrial complex is important to improve meat quality in the beef industry.

REFERENCES

Falkenberg et al. (2002) *Nat Genet.* 31:289-94.
Fisher and Clayton (1988) *Mol Cell Biol.* 8:3496-3509.
Gleyzer et al. (2005) *Biochem Biophys Res Commun.* 334: 516-23.
Owen et al. J Biol Chem. 2002 Aug. 23; 277(34):30409-12.

or equal to choice (QG, <Se vs, >Ch), intramuscular fat content (IMF %, %), marbling score (MBS, 10 to 99), marbling score divided by days on feed (MBS/DOF), additional carcass value (additional carc value, $), adjusted net return—all costs removed (adj. net return—all costs removed, $) and adjusted net return—initial animal value not removed (adj. net return—initial animal value not removed, $).

The analysis models were genotype, wherein genotypes were fit as fixed effects and additive or allele substitution, which showed regression on allele number (0, 1, 2). Both models fit with 2-marker combinations. Another analysis model is haplotype, which shows regression on (expected) haplotype when fitting multiple TFAM markers. Significant single marker associations are presented in Table 4 and significant 2-marker combinations are presented in Table 5.

TABLE 4

Single Marker Analyses for TFAM-1, TFAM-2, & FABP4

| | | | Model | | | | | | | | | |
|---|---|---|---|---|---|---|---|---|---|---|---|---|
| | | | Allele Substitution | | | Fixed genotype | | | Genotype | | | |
| Marker | Trait | N | Estimate | SE | P-value | P-value | Add. est. | SE | Add. P-Value | Dom. est. | SE | Dom. P-value |
| FABP4 | QG Ch(1, 2, 5, 9, 20) | 1528 | −.065 | .019 | .0007 | .0027 | −.057 | .023 | .0156 | .020 | .030 | .5161 |
| | REA/cwt HCW | 1528 | .00016 | .00009 | .0558 | .0345 | .00027 | .00010 | .0102 | .00023 | .00013 | .0795 |
| TFAM-1 | Calc Lv Wt | 1539 | 10.629 | 3.578 | .0030 | .0122 | 10.794 | 3.731 | .0039 | .816 | 5.178 | .8748 |
| | Hot Carcass Wt | 1539 | 5.929 | 2.402 | .0137 | .0478 | 5.894 | 2.504 | .0187 | −.172 | 3.476 | .9606 |
| | HCW Value | 1539 | .274 | .192 | .1535 | .0073 | .432 | .200 | .0308 | .776 | .277 | .0052 |
| | Marbling score | 1125 | .906 | .358 | .0115 | .0354 | .962 | .373 | .0099 | .281 | .516 | .5865 |
| | MBS/DOF | 1125 | .006 | .003 | .0452 | .0892 | .007 | .003 | .0296 | .004 | .004 | .3641 |
| TFAM-2 | Calc Lv Wt | 1503 | −9.607 | 3.590 | .0075 | .0099 | −10.145 | 3.608 | .0050 | −7.321 | 5.070 | .1490 |
| | Hot Carcass Wt | 1503 | −5.931 | 2.418 | .0143 | .0270 | −6.208 | 2.431 | .0107 | −3.775 | 3.416 | .2693 |
| | HCW Value | 1503 | −.453 | .193 | .0191 | .0104 | −.415 | .194 | .0326 | .520 | .273 | .0567 |
| | Marbling score | 1097 | −.845 | .366 | .0210 | .0557 | −.872 | .368 | .0179 | −.345 | .512 | .5005 |
| | Ribeye Area | 1503 | −.142 | .058 | .0139 | .0439 | −.139 | .058 | .0165 | .037 | .082 | .6503 |

Markers fit for allele substitution: A for TFAM1; C for TFAM2 & FABP4
Marbling scores range from 10 to 99; 10 = PD0 = Std, 99 = A90 = Prime
QG Ch(1, 2, 5, 9, 20) implies Ch or better-includes Prime, Ch, CAB, Sterling Silver, & Angus Pride;
Alternate included Se, No Roll, Dark cutter, & Hard bone

TABLE 5

Two Marker Analyses for TFAM-1, TFAM-2, & FABP4

| | | | | Model Allele Substitution | | | | | |
|---|---|---|---|---|---|---|---|---|---|
| | | | | Marker 1 | | | Marker 2 | | |
| Marker 1 | Marker 2 | Trait | N | Estimate | SE | P-value | Estimate | SE | P-value |
| TFAM-1 | FABP4 | Adj NR w/o init val | 1526 | −1.383 | 4.007 | .7300 | −.416 | 3.786 | .9124 |
| | | Calc Lv Wt | 1526 | 12.076 | 4.388 | .0060 | −4.194 | 4.146 | .3119 |
| | | Hot Carcass Wt | 1526 | 7.092 | 2.948 | .0163 | −2.672 | 2.785 | .3374 |
| | | IMF % | 377 | −.046 | .078 | .5526 | −.056 | .072 | .4345 |
| | | MBS/DOF | 1117 | .007 | .003 | .0299 | −.001 | .003 | .8048 |
| | | Marbling score | 1117 | 1.069 | .429 | .0128 | −.334 | .408 | .4140 |
| | | QG Ch(1, 2, 5, 9, 20) | 1526 | −.004 | .021 | .8403 | −.072 | .020 | .0003 |
| TFAM-1 | TFAM-2 | Adj NR w/o init val | 1501 | 8.151 | 5.602 | .1459 | 11.913 | 5.791 | .0398 |
| | | DMI | 1501 | 22.819 | 25.853 | .3776 | −2.520 | 26.725 | .9249 |
| | | DMI/DOF | 1501 | .208 | .179 | .2457 | .034 | .185 | .8555 |
| | | HCW Value | 1501 | −.466 | .328 | .1561 | −.938 | .339 | .0058 |
| | | QG Ch(1, 2, 5, 9, 20) | 1501 | −.042 | .030 | .1558 | −.066 | .031 | .0302 |
| | | YG | 1434 | .080 | .039 | .0419 | .059 | .041 | .1481 |
| TFAM-2 | FABP4 | Calc Lv Wt | 1495 | −11.350 | 4.367 | .0094 | −5.556 | 4.050 | .1703 |
| | | DOF | 1495 | −.181 | .475 | .7030 | −.672 | .441 | .1274 |
| | | Hot Carcass Wt | 1495 | −6.424 | 2.943 | .0292 | −3.431 | 2.729 | .2090 |
| | | Marbling score | 1093 | −.990 | .433 | .0223 | −.372 | .403 | .3568 |
| | | QG Ch(1, 2, 5, 9, 20) | 1495 | −.017 | .021 | .4248 | −.063 | .020 | .0014 |
| | | REA/cwt HCW | 1495 | −.00002 | .00009 | .8546 | .00018 | .00009 | .0385 |

| | | | | Model Genotype | | | | | |
|---|---|---|---|---|---|---|---|---|---|
| | | | | Markers 1 * 2 | | | Marker 1 | Marker 2 | Markers 1 * 2 |
| Marker 1 | Marker 2 | Trait | N | Estimate | SE | P-value | P-value | P-value | P-value |
| TFAM-1 | FABP4 | Adj NR w/o init val | 1526 | −.621 | 5.003 | .9013 | .4996 | .2159 | .0404 |

TABLE 5-continued

Two Marker Analyses for TFAM-1, TFAM-2, & FABP4

| | | | | | | | | | |
|---|---|---|---|---|---|---|---|---|---|
| | | Calc Lv Wt | 1526 | −3.120 | 5.478 | .5691 | .0153 | .2933 | .6639 |
| | | Hot Carcass Wt | 1526 | −2.237 | 3.680 | .5435 | .0393 | .1629 | .5571 |
| | | IMF % | 377 | .042 | .095 | .6598 | .4765 | .9997 | .0372 |
| | | MBS/DOF | 1117 | −.004 | .004 | .4059 | .0426 | .8568 | .6798 |
| | | Marbling score | 1117 | −.317 | .543 | .5594 | .0282 | .4454 | .8402 |
| | | QG Ch(1, 2, 5, 9, 20) | 1526 | .034 | .026 | .2028 | .6912 | .0016 | .6534 |
| TFAM-1 | TFAM-2 | Adj NR w/o init val | 1501 | −2.564 | 5.312 | .6294 | .1528 | .0868 | .3998 |
| | | DMI | 1501 | −12.727 | 24.514 | .6037 | .0152 | .0230 | .0388 |
| | | DMI/DOF | 1501 | −.022 | .170 | .8989 | .0142 | .0171 | .0479 |
| | | HCW Value | 1501 | .650 | .311 | .0368 | .3637 | .9102 | .6043 |
| | | QG Ch(1, 2, 5, 9, 20) | 1501 | .033 | .028 | .2388 | .2871 | .5127 | .2949 |
| | | YG | 1434 | −.040 | .037 | .2760 | .4031 | .5462 | .7033 |
| TFAM-2 | FABP4 | Calc Lv Wt | 1495 | 4.329 | 5.306 | .4147 | .0113 | .1017 | .6175 |
| | | DOF | 1495 | .209 | .577 | .7175 | .9786 | .0189 | .0398 |
| | | Hot Carcass Wt | 1495 | 1.235 | 3.576 | .7299 | .0530 | .0614 | .8073 |
| | | Marbling score | 1093 | .311 | .529 | .5568 | .0726 | .8003 | .8134 |
| | | QG Ch(1, 2, 5, 9, 20) | 1495 | −.025 | .026 | .3308 | .8411 | .0051 | .2986 |
| | | REA/cwt HCW | 1495 | −.00011 | .00011 | .3377 | .8702 | .0523 | .2467 |

Markers fit for allele substitution: A for TFAM1; C for TFAM2 & FABP4
Marbling scores range from 10 to 99; 10 = PD0 = Std, 99 = A90 = Prime
QG Ch(1, 2, 5, 9, 20) implies Ch or better-includes Prime, Ch, CAB, Sterling Silver, & Angus Pride;
Alternate included Se, No Roll, Dark cutter, & Hard bone Example 4

FIG. 7 shows a flowchart of the input of data and the output of results from the analysis and correlation of the data pertaining to the breeding, veterinarian histories and performance requirements of a group of animals such as from bovines. The flowchart illustrated in FIG. 7 further indicates the interactive flow of data from the computer-assisted device to a body of students learning the use of the method of the invention and the correlation of such interactive data to present an output as a pie-chart indicating the progress of the class. The flowchart further indicates modifications of the method of the invention in accordance with the information received from the students to advance the teaching process or optimize the method to satisfy the needs of the students.

FIG. 8 illustrates potential relationships between the data elements to be entered into the system. Unidirectional arrows indicate, for example, that a barn is typically owned by only one farm, whereas a farm may own several barns. Similarly, a prescription may include veterinarian products.

FIG. 9A illustrates the flow of events in the use of the portable computer-based system for data entry on the breeding and rearing of a herd of cows. FIG. 9B illustrates the flow of events through the sub-routines related to data entry concerning farm management. FIG. 9C illustrates the flow of events through the sub-routines related to data entry concerning data specific to a company.

FIG. 10 illustrates a flow chart of the input of data and the output of results from the analysis and the correlation of the data pertaining to the breeding, veterinarian histories, and performance requirements of a group of animals.

The invention is further described by the following numbered paragraphs:

1. A method for sub-grouping animals according to genotype wherein the animals of each sub-group have a similar polymorphism in a mitochondrial transcription factor A ("TFAM") gene comprising:

(a) determining the genotype of each animal to be sub-grouped by determining the presence of a single nucleotide polymorphism in the TFAM gene, and (b) segregating individual animals into sub-groups wherein each animal in a sub-group has a similar polymorphism in the TFAM gene.

2. A method for sub-grouping animals according to genotype wherein the animals of each sub-group have a similar genotype in the TFAM gene comprising:

(a) determining the genotype of each animal to be sub-grouped by determining the presence of a single nucleotide polymorphism(s) of interest in the TFAM gene, (b) segregating individual animals into sub-groups depending on whether the animals have, or do not have, the single nucleotide polymorphism(s) of interest in the TFAM gene.

3. The method of paragraphs 1 or 2, wherein the single nucleotide polymorphism(s) of interest is selected from the group consisting of an A to C substitution at the −1220 nucleotide position in the promoter of the TFAM gene, a T to C substitution at position −1212 in the promoter of the TFAM gene and a T to C substitution at position −995 in the promoter of the TFAM gene.

4. A method for sub-grouping animals according to genotype wherein the animals of each sub-group have a similar genotype in the TFAM gene comprising:

(a) determining the genotype of each animal to be sub-grouped by determining the presence of an A to C substitution at the −1220 nucleotide position in the promoter of the TFAM gene, a T to C substitution at position −1212 in the promoter of the TFAM gene and a T to C substitution at position −995 in the promoter of the TFAM gene, and (b) segregating individual animals into sub-groups depending on whether the animals have, or do not have, an A to C substitution at the −1220 nucleotide position in the promoter of the TFAM gene, a T to C substitution at position −1212 in the promoter of the TFAM gene and a T to C substitution at position −995 in the promoter of the TFAM gene.

5. A method for identifying an animal having a desirable phenotype as compared to the general population of animals of that species, comprising determining the presence of a single nucleotide polymorphism in the TFAM gene of the animal, wherein the polymorphism is selected from the group consisting of an A to C substitution at the −1220 nucleotide position in the promoter of the TFAM gene, a T to C substitution at position −1212 in the promoter of the TFAM gene and a T to C substitution at position −995 in the promoter of the TFAM gene single nucleotide polymorphism is indicative of a desirable phenotype.

6. The method of paragraph 5, wherein the desirable phenotype is feed intake, growth rate, body weight, carcass merit and composition, milk yield or any combination thereof.

7. The method of paragraph 5 or 6, wherein the desirable phenotype is additional carcass value (additional carc value, $), average daily gain (ADG, lb/d), backfat thickness (BFAT, in), calculated live weight (Calc Lv Wt, lb), calculated yield grade (cYG), days on feed (DOF, d), dressing percentage (DP, %), dry matter intake (DMI, lb), dry matter intake per day on feed (DMI per DOF, lb/d), hot carcass weight (HCW, lb), hot carcass weight value (HCW value, $), intramuscular fat content (IMF %, %), marbling score (MBS, 10 to 99), marbling score divided by days on feed (MBS/DOF), quality grade, less than or equal to select versus greater than or equal to choice (QG, <Se vs, >Ch), ribeye area (REA, in$^2$), ribeye area per hundred weight HCW (REA/cwt HCW, in$^2$/100 lb hot carcass weight (HCW), subcutaneous fat depth (SFD) or any combination thereof.

8. The method of any one of paragraphs 1 to 7 wherein the animal is a bovine.

9. The method of any one of paragraphs 1 to 8 wherein the TFAM gene is a bovine TFAM gene.

10. An interactive computer-assisted method for tracking the rearing of livestock bovines comprising, using a computer system comprising a programmed computer comprising a processor, a data storage system, an input device, an output device, and an interactive device, the steps of: (a) inputting into the programmed computer through the input device data comprising a breeding history of a bovine or herd of bovines, (b) inputting into the programmed computer through the input device data comprising a veterinary history of a bovine or herd of bovines, (c) correlating the veterinary data with the breeding history of the bovine or herd of bovines using the processor and the data storage system, and (d) outputting to the output device the breeding history and the veterinary history of the bovine or herd of bovines.

11. The method according to paragraph 10, wherein the computer system is an interactive system whereby modifications to the output of the computer-assisted method may be correlated according to the input from the interactive device.

12. The method according to paragraph 10 or 11, further comprising the steps of inputting into the programmed computer diagnostic data related to the health of the cow or herd of cows; and correlating the diagnostic data to the breeding and veterinary histories of the cow or herd of cows.

13. The method according to any one of paragraphs 10 to 12, wherein the veterinary data comprises a vaccination record for a cow or herd of cows.

14. The method according to any one of paragraphs 10 to 13 wherein the health data is selected from the group consisting of husbandry condition data, herd history, and food safety data.

15. The method according to any one of paragraphs 10 to 14, further comprising at least one further step selected from the group consisting of inputting into the programmed computer data related to the quality control of the bovine or herd of bovines and correlating the quality control data to the breeding and veterinary histories of the cow or herd of cows, inputting into the programmed computer performance parameters of the cow or herd of cows; and correlating the required performance parameters of the bovine or herd of bovines to a specific performance requirement of a customer, correlating the vaccine data to the performance parameters of the bovine or herd of bovines, correlating herd to the performance parameters of the bovine or herd of bovines, correlating the food safety data to the performance parameters of the bovine or herd of bovines, correlating the husbandry condition data to the performance parameters of the bovine or herd of bovines, inputting into the programmed computer data related to the nutritional data of the bovine or herd of bovines; and correlating the nutritional data to the performance parameters of the bovine or herd of bovines, and alerting to undesirable changes in the performance parameters of the bovine or herd of bovines.

16. The method according to any one of paragraphs 10 to 15, further comprising the steps of inputting into the programmed computer through the input device data comprising a genotype of a bovine; correlating a physical characteristic predicted by the genotype using the processor and the data storage system; and outputting to the output device the physical characteristic correlated to the genotype for a bovine or population of bovines, and feeding the animal(s) a diet based upon the physical characteristic, thereby improving bovine production.

17. The computer-assisted method according to any one of paragraphs 10 to 16 for optimizing efficiency of feedlots for livestock comprising outputting to the output device the breeding and veterinary history of the bovine or herd of bovines and feeding the animal(s) a diet based upon their breeding and veterinary histories, thereby optimizing efficiency of feedlots for the bovine or herd of bovines.

18. A method of transmitting data comprising transmission of information from such methods according to any one of paragraphs 10 to 16, selected from the group consisting of telecommunication, telephone, video conference, mass communication, a presentation, a computer presentation, a POWERPOINT™ presentation, internet, email, and documentary communication.

19. An interactive computer system according to any one of paragraphs 10 to 16 for tracking breeding and welfare histories of cows comprising breeding and veterinarian data corresponding to a bovine or herd of bovines, and wherein the computer system is configured to allow the operator thereof to exchange data with the device or a remote database.

20. The interactive computer system according to paragraph 19, wherein the input and output devices are a personal digital assistant or a pocket computer.

21. A method of doing business for tracking breeding and welfare histories of livestock comprising breeding and veterinarian data corresponding to one or more livestock animals comprising providing to a user the computer system of paragraph 19.

22. A method of doing business for tracking breeding and welfare histories of livestock comprising breeding and veterinarian data corresponding to one or more livestock animals comprising providing to a user the computer system of paragraph 20.

23. The method of doing business according to paragraph 21, further comprising providing the animal owner or customer with sample collection equipment, such as swabs and tags useful for collecting samples from which genetic data may be obtained, and wherein the tags are optionally packaged in a container which is encoded with identifying indicia.

24. The method of doing business according any one of paragraphs 10 to 16, wherein the computer system further comprises a plurality of interactive devices and wherein the method further comprises the steps of a receiving data from the interactive devices, compiling the data, outputting the data to indicate the response of a student or class of students to a question relating to the operation of the computer-assisted method, and optionally modifying the operation of the computer-assisted method in accordance with the indication of the response.

25. The method of any one of paragraphs 8 to 24 wherein the data comprises presence or absence of one or more of a single nucleotide polymorphism(s) of interest in the TFAM gene.

26. The method of paragraph 25 wherein the single nucleotide polymorphism(s) of interest is selected from the group consisting of an A to C substitution at the −1220 nucleotide position in the promoter of the TFAM gene, a T to C substitution at position −1212 in the promoter of the TFAM gene and a T to C substitution at position −995 in the promoter of the TFAM gene.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method for identifying a bovine animal having a higher marbling score (MBS), thicker subcutaneous fat depth (SFD), or a combination thereof said method comprising:
   (a) obtaining a biological sample from said bovine animal, said biological sample comprising nucleic acids encoding the bovine transcription factor A ("TFAM") gene from said bovine;
   (b) detecting in said nucleic acids the presence of at least one of:
      (i) a C in both alleles of the TFAM gene at position corresponding to position 379 of SEQ ID NO: 1;
      (ii) a C in both alleles of the TFAM gene at position corresponding to position 387 of SEQ ID NO: 1;
   (c) correlating the presence of the nucleic acid content of (b) with a higher marbling score, thicker subcutaneous fat depth (SFD), or a combination thereof in said bovine animal.

* * * * *

UNITED STATES PATENT AND TRADEMARK OFFICE
CERTIFICATE OF CORRECTION

PATENT NO. : 7,662,564 B2  Page 1 of 1
APPLICATION NO. : 11/441928
DATED : February 16, 2010
INVENTOR(S) : Jiang et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 383 days.

Signed and Sealed this

Twenty-eighth Day of December, 2010

David J. Kappos
*Director of the United States Patent and Trademark Office*

SEQUENCE LISTING

```
<160> NUMBER OF SEQ ID NOS: 28

<210> SEQ ID NO 1
<211> LENGTH: 1821
<212> TYPE: DNA
<213> ORGANISM: Bos taurus

<400> SEQUENCE: 1
tagatcagat ttataagaac tttatagcaa ggcttatcaa aatgacactt taaaacaaca      60
aagactttaa atattcaaaa aaatttttta tatctatcaa acgtctgaaa gaataaaaac     120
actctagaaa aatgtaaaga aaagttgttg cagaaatcag ctaaaatgta attataagga     180
attctatccc atacttttag cttgacattg tagtgtaact gttcatttct ttgcctctgc     240
cactagactt catgggcggt gaaaagaagg ctgtgttttt tatctaagtt tgtggccttg     300
tacataatgt gtactcagaa aataatcaaa caaacaaaat ccaaccctgt ttcttccatg     360
acagagtgag agatttggmc agatgaycta aaaggtccct ttcaatactg agaattttttg   420 aaaaggaagt ggtgatagtt gcttaccact tagaagtggg cttggtggtc gcactcaacg     480
ggccagtgaa agactctcag ctcaatatga cactagtaag aattttctta caaacctatc     540
caacagagaa aaagctgttt caggaagtgg ctctttgaaa taaatggaac ctgagagcta     600
gaagtgtcct tagatagctt tagataaggt tatcctaatc tttttttcatg ccattgtcca     660 catggaaaat ggcggtactg cacatcgatc aatatctcaa ggcataattg tcacaggttc     720
tcagagcttt ggttgggaaa tgatctcgtc caacatcctc gtctgcagtg ggggaaatta     780
aatcttacag cggggaagtg acatttccag atcaagacgt taatgcaaat gatggagcta     840
gaactctagt ctccggacag ataactagtc agtctcctcc ccacaaagta agcagggttg     900
gatgtcaagc ttgccgatta ggtcagcgat agtctcagtg gatgggcta tggtctggat      960 ctgtgttgct ttaaatgtgg tcccataacc actggcatca gagcttgtta aaccttgagg    1020
aacttgttaa gatagctgag acatgggacc cacacaaaca cggaatcagg ctctgcggca    1080
aggcccggga atctgcattt taaggttaga aaccgtgatc catcccacct cctctacggt    1140
aattttggac tacgcgctcc gacttgaact gagggactct gctgggcgca tatcgcccag    1200
caacctgacc tcagagcagc gtgggcggca cggctaccgc cgttctagcc gtaaactgtc    1260
```

| | |
|---|---:|
| tgttacgtac tagcccttcc agtcgtcaca aaccagccag ggccccatcc gtgtgaggac | 1320 |
| accgccgtgc ctccaatcag cctcctggcc gggcggctga gcaggctgcc ggggggggtgg | 1380 |
| ggggggtgggg ttgggacaga ggcggctcag cttcgccccc tcgaggccag gtccctccgc | 1440 |
| aggctagccg ggttgcagtt tcccttctcc gcctccgagc gccttttct tcgtagtccc | 1500 |
| gcccaccaag gaagccagta cagcgcctgc gccttctacc ttgccccgcc tcctagctaa | 1560 |
| tcggaagtta gccgatttcc catagtgccc cgcgagtggc gggcatgata gtaaatccgg | 1620 |
| taggctctct ggcgggttta agtcggcttt gttgcggttt ctcttgtgcc agggcgctgt | 1680 |
| agggaattgg ggcctggtca gtgctttgtc tgcggatgca atggcgcttc tccggggcgt | 1740 |
| atggggcgtg ctgaatgcgc tgggaaagtc aggagcggat ctctgcgcgg gctgtggcag | 1800 |
| tcgactgcgc tctccctta g | 1821 |

<210> SEQ ID NO 2
<211> LENGTH: 2259
<212> TYPE: DNA
<213> ORGANISM: Bos taurus

<400> SEQUENCE: 2

| | |
|---|---:|
| cgggcatgat agtaaatccg gtaggctctc tggcgggttt aagtcggctt tgttgcgggt | 60 |
| tctcttgtgc cagggcgctg tagggaattg gggcctggtc agtgctttgt ctgcggatgc | 120 |
| aatggcgctt ctccggggcg tatggggcgt gctgaatgcg ctgggaaagt caggagcgga | 180 |
| tctctgcgcg ggctgtggca gtcgactgcg ctctcccttt agttttgcgt atgttccaaa | 240 |
| atggttttca tccagcttga gtggttatcc aaagaagccc atgacttcat acgttcgatt | 300 |
| ttctaaagaa cagctgccca tatttaaagc tcagaaccca gatgcaaaaa attcagaact | 360 |
| aattaaaaaa attgccaagc tatggaggga acttcctgat tcagagaaaa agatatatga | 420 |
| agatgcttac agggcagact ggcaggtata caaggaagag ataaacagaa ttcaagaaca | 480 |
| actaactcca agtcaaatgg tatctttgga aaaagaaatc atgcagaaac gtttaaaaaa | 540 |
| gaaagcgtta ataaaaaaga gagagttaac aatgcttgga aaaccgaaaa gacctcgctc | 600 |
| agcttataac attttatag ctgaacgttt tcaggaagct agggatggca catcacaggt | 660 |
| aaagctgaaa gctataaatg aaaactggaa aaatctctct aattctcaaa agcaagtata | 720 |
| tattcagctt gctaaagatg ataaaattcg ttattataac gaaatgaaat cttgggagga | 780 |
| acaaatgatg gaagttggac gagaagatct tatacgtcgc tcaattaaat acccagcaaa | 840 |
| aaatgaccct gagaagtttt aaaatagaag attgagttat gttcataatg gatagacata | 900 |
| agaaaccaac taggtctcaa taccggaagc tgttgtaaaa ttagaatgga taaagttggt | 960 |
| gaacatttat atttaattcc ttttctgtag cccatggact tctgccagcc aattcaatac | 1020 |
| attttgtatt ggtgtcttgc ttttgaaaac ccaaacagat aagacttcat gtggaattta | 1080 |
| ttttgtgttt aggaactact gagcatcaaa ataatccatg aaatgtagca gtgaatcatt | 1140 |
| ttaccttga taaaggtaaa tcagactgtg aagttttttt atacttggtg attatggaaa | 1200 |
| aaatattctt gtttccttat attatggaag caggagtttc ctattcataa gtatctcaaa | 1260 |
| gtttgtagaa gccatagtgt tctatgatat aactgcattt ttaaaagagc atccagaact | 1320 |
| catgctggta aattccaaat cctgggtata attcatatta taatcagact tgatggttgt | 1380 |
| acatgtgagg aatttctggt atcagttgca gcttttataa aaggtataga tttataaacc | 1440 |
| ttttcctcat tatctttttc ctaaattaaa aactaaaaaa ttatgtacca aatctatgca | 1500 |
| tattgtttta tattgcatag aataaaaatt atgtgtttcc taattatgtt ttaaggtgaa | 1560 |

```
acattcattt tatagctttc tgggattttt gtttgttttt ttaaacaaag taggagtttg    1620
tatactgaat tatttttct cttatgtaaa tatatttatc cagaaagtag agaacttatt    1680
tggtgtaagt tttaaaatga gagatctaaa aaaatcatgt ctccaaagtc tctcaaattg    1740
gaacctataa tttttaaaca tttgcataac atataaaagc ctgtataata attaatagcc    1800
agttctagcc tgatgcccac atccagccca ctgcctgctt ttcttggcct tgtcaactaa    1860
gaattgttca cagtttaaa tagttaaaaa aaactaagca tacttcaaga cacatgaaaa    1920
ttaatatgaa attcagtgtc cataaaaaaa tgttttattg gaacacagcc acactcatcg    1980
attatggctg tttttgtaca atagtgcagt tgacttggtt gctacagaga ggtgcagcct    2040
gcaaagactg acccgtatag tgtggaatga gatgctctta agttacttgc tgtggctcag    2100
taaaatacat cttaacagtt ttccagttag catttaaacc ttacccttc tagcatttga    2160 ttatcttctt aacaagagtc aaaggttttt caaaatccac accacctttt tgagcaaaat    2220
attcaactgt catcatcagt tcacatgaat ttataactc                          2259

<210> SEQ ID NO 3
<211> LENGTH: 16666
<212> TYPE: DNA
<213> ORGANISM: Bos taurus

<400> SEQUENCE: 3
tagatcagat tttataagaac tttatagcaa ggcttatcaa aatgacactt taaaacaaca     60
aagactttaa atattcaaaa aaattttta tatctatcaa acgtctgaaa gaataaaaac    120
actctagaaa aatgtaaaga aaagttgttg cagaaatcag ctaaaatgta attataagga    180
attctatccc atactttag cttgacattg tagtgtaact gttcatttct ttgcctctgc    240
cactagactt catgggcggt gaaaagaagg ctgtgttttt tatctaagtt tgtggccttg    300
tacataatgt gtactcagaa aataatcaaa caaacaaaat ccaaccctgt ttcttccatg    360
acagagtgag agatttggac agatgatcta aaaggtccct ttcaatactg agaattttttg   420 aaaaggaagt ggtgatagtt gcttaccact tagaagtggg cttggtggtc gcactcaacg    480
ggccagtgaa agactctcag ctcaatatga cactagtaag aattttctta caaacctatc    540
caacagagaa aaagctgttt caggaagtgg ctctttgaaa taaatggaac ctgagagcta    600
gaagtgtcct tagatagctt tagataaggt tatcctaatc ttttttcatg ccattgtcca    660
catggaaaat ggcggtactg cacatcgatc aatatctcaa ggcataattg tcacaggttc    720
tcagagcttt ggttgggaaa tgatctcgtc caacatcctc gtctgcagtg ggggaaatta    780
aatcttacag cggggaagtg acatttccag atcaagacgt taatgcaaat gatgagcta    840 gaactctagt ctccggacag ataactagtc agtctcctcc ccacaaagta agcagggttg    900
gatgtcaagc ttgccgatta ggtcagcgat agtctcagtg gatggggcta tggtctggat    960
ctgtgttgct ttaaatgtgg tcccataacc actggcatca gagcttgtta aaccttgagg   1020
aacttgttaa gatagctgag acatgggacc cacacaaaca cggaatcagg ctctgcggca   1080
aggcccggga atctgcattt taaggttaga aaccgtgatc catcccacct cctctacggt   1140
aattttggac tacgcgctcc gacttgaact gagggactct gctgggcgca tatcgcccag   1200
caacctgacc tcagagcagc gtgggcggca cggctaccgc cgttctagcc gtaaactgtc   1260
tgttacgtac tagcccttcc agtcgtcaca aaccagccag ggcccatcc gtgtgaggac   1320 accgccgtgc ctccaatcag cctcctggcc gggcggctga gcaggctgcc ggggggtgg   1380
```

```
gggggtgggg ttgggacaga ggcggctcag cttcgccccc tcgaggccag gtccctccgc   1440
aggctagccg ggttgcagtt tcccttctcc gcctccgagc gccttttct tcgtagtccc    1500 gcccaccaag gaagccagta cagcgcctgc gccttctacc ttgccccgcc tcctagctaa   1560
tcggaagtta gccgatttcc catagtgccc cgcgagtggc gggcatgata gtaaatccgg   1620
taggctctct ggcgggttta agtcggcttt gttgcggttt ctcttgtgcc agggcgctgt   1680
agggaattgg ggcctggtca gtgctttgtc tgcggatgca atggcgcttc tccggggcgt   1740
atggggcgtg ctgaatgcgc tgggaaagtc aggagcggat tctgcgcgg gctgtggcag    1800 tcgactgcgc tctcccttta ggtaagcctg cttgcctgca ccttcggagg cggaagggtt   1860
caggacgcct tggggttaga atgtagacgc tgttctccgc tttctgaccc ccctgaaatg   1920
gtcaggactg acttagccct gtgattccga cctcgacctt gccaagggga tgatagcttt   1980
gagacgaggc cttactgctt cagtacccct tgccttcctt ccggtcacct ttcccctcct   2040
cccgtccctc ctcattctcg taccttggag caccgggttc gttgtcccct gcgaagtcgc   2100
cgcaaagtct cctgccttca tctagccatt gaggcgaagc ccaggagctg agatacatg    2160 cttccttca ctctctgccc ttgctagggg gttaggggct ttgagacttc agttttgcaa    2220
gctctttccc ctggatagga caggatttta aatatcatta gtgttcttgc cgaaggtgtt   2280
aggtgtcaga tatgtagcat cttgatatct tgcttggcat ctgtgtgcac gtaattatga   2340
atacaggtac ttaaatgttt aacactggtt attttctttt tatttatatg tagttttgcg   2400
tatgttccaa aatggttttc atccagcttg agtggttatc caaagaagcc catgacttca   2460
tacgttcgat tttctaaaga acagctgccc atatttaaag ctcagaaccc aggtaaggag   2520
tttgggttat atactcttct ctgatgtact aaagatgcca ctaagcagtt aaattgcaga   2580
cttgattttc agtatcaagg catctgttga atgcagaaac ataaccattc tgtgtgatgg   2640
cctgtaaaat agatataaca tgggcttgta tgaaagccac ctgccaatgc aggagacata   2700
ggagtcgcgg gttcaatccc tgggtaggga agatcccta gaaaagggaa tggtgacccg    2760
ctcctttatt ctggcctgga aaattatgga cagaggagcc tggcaggcca cagtccatgg   2820
atttgcagaa tcagacacga ctgaagcgac ctagcaggca tgcataagga atcagtgtaa   2880
gcacagcagt aagtaattt taccaaataa aaatgcttta aatgtaattg agaactggtg    2940
aaagctattt taaaatagc atgtagaatg caaagtactt aggaaagagg ataaaaaagc    3000
tgaatttggg gccttgtggc cattggccca gaggaccatt gacgaatcat tttacctctt   3060
gcttagctcc tgcttctccc actgcaaatt attaataaag ttgcagtgaa ataatttatg   3120
tggatgtgtt gcataaactt gaaagctgaa tacaggttat tgttaatttt aagagcttt    3180 tgactgaaag ccagttgaat ttctgaaaga tttccagtta ggtttgttga ctccctagaa   3240
agactgggtc cttattgggg ctgtagtgta aagatagtga ccaaattagt aattgctgag   3300
ctttctttat aattcctaaa gctttttcat atgcattata tcacagggca cttatgaaaa   3360
tcatgtgagc tgtaatagtc acgtaaagaa ctggtttaag agacatgctt cagtactcac   3420
atcttttgaa atgtaggagt tgaaactaac aagtagttg ttaaatcatt tatacccttgt   3480 cattccagtt aagatgggaa ggaaatggag aaaaattatt tggttttaga ataatttagc   3540
ttgtttgcaa acaatatttc tgtaatttag atacaggtgg tgttatatga atcaagacta   3600
tattttgttg tttagtcagg ttttatgaac ttggtcattc ctgaaagact tgaaaaaaat   3660 gttttttgatt gaaatatgaa gtagaaaact tgtagacact gattcccaa ttgctttaac    3720 ttagtaatca attcctgagg accatttggg tggtaagtgg tactattcct taatttaatc   3780
```

```
attagataat agactttaat aatgttagat aaaatattaa attatttatt gtacttaaat     3840
tagttggtta aagaaaaact aaataatttt aagttgtgtg tggtaaaatg tctgtaaaaa     3900
tacttaattt tagagctaat ggattattct ttcctgaaag tctttagaaa ttgatccaga     3960
gatgtaaaat ggtgatacca attttttattt catttcatag atgcaaaaaa ttcagaacta    4020
attaaaaaaa ttgccaagct atggagggaa cttcctgatt cagagaaaaa ggtaagcata    4080 taaatttta acattgctga ccagttactt tgcaggtaag acaactgtc atgtccttta      4140 aggaaaaaga tgacccagag tttttttttt taacgtttgt tatctcaaag gaatgtcata    4200
ctttctcatc cacataaatg atgagaatat ggataaatgg cagtggtgat gaagcgttgg    4260
tttttgaagc aatttgaagt tggaggccag ttgctagacc ttcaccttgg ataacacatt    4320
tgaagaacac gtgatttata agtgggattt cagagtgcat tttccacttg gtggttcagt    4380
cagtttgctg aagttacgca gttgtccttc cccgtcaggt gtgctatgtt taattagcca    4440
gcaatagttt atcaacttct tatttggatt tttttataga tatatgaaga tgcttacagg    4500
gcagactggc aggtatacaa ggaagagata aacagaattc aagaacaact aactccaagt    4560
caaatggtat ctttggaaaa agaaatcatg cagaaacgtt taaaaagaa agcgttaata     4620 aaaaagagag tgagtatggt tggcataaaa ctgaaatttg gcaaaaaact gaaatttata    4680
tatctataaa tacaggtttg cttttttttcc tttggcaaaa aactgaaatt tatgtatcta   4740
taaatacagg ttttttccct tgttttggtg acgtggtaga gaatgacttc agttaggaaa    4800
aaataggata gtttccttct gccactagga ccacgtgcct ttgagtatgt tgtaaaccgt    4860
ttttgctcct tttggatgtg tctgagttcg agatacataa ttaggactgg tgtgaaagct    4920
gtaggaacag agtaggaaa caggaagatc aggaatagca aaagtcttga ttctctgtca     4980
tttctagagt accttactga tttgaattgt tctataggtg atggtgaatt tgattctgaa    5040
tattgctgaa tggactgaat tcattaactt atcaatgttt taaaaatacc tattgtagat    5100
aataaaatta aagtgccttt aggatgaaat tcaattttttc ctcattaaaa atcccacatg   5160
gttcaaaatt agtggcttcc agtttaaggt attagtccat ataaattcta ttgtttgaca    5220
gactacatct ttccatacta ttaggtgtga ggtggtgaac ttgctgatcc agtatatata    5280
ccataaaaaa tgatcatcag agcaaaagct tacttctctg aaaaagtaga ttccagcctt    5340
tagtatgaag tgatggaatc tctcttcctg atcgctgtgt cttaagccct cctagctctt    5400
gggttgagga ctcacccaat ttcaagtcaa tgatagtaat cggagactgc taatccaatc    5460
agtaaaagga agccagaaaa aatagggatg gtatttggag ggtggaaaac tagggtttat    5520
tctctcttga gctctccctt gctctttaat gcacccaact agtactttga gtggggagga    5580
ccagaaatga agattgagca gatataagga gtttcttatt caggtatttc tgttcctttc    5640
tctgttgtat tccagttcag ttcagttgct cagttgtgtc tgactctttg gtaccccatg    5700
gactgcagca tggcaggcct ccctgtccat tagcaacttc tggaggttac tcaaactcat    5760
gtccattgag ttggtgatgc catccaacca tctcatcctc tgtcatcccc ttctcctcct    5820
accttcaatc agggtctttt ccagtgagtc agttcttcgt accagatggc caaagtattg    5880
gagtttcagc ttcagcatca gtccttccag tgaatattca ggactgattt cttttaggat    5940
ggactggttg aatcttcttg gagtccaagg ggctctcaag agtcttctcc aacaccacaa    6000
ttcaagacat caattcttga gcgctcagct ttgtttatga tccaactcaa catccataca    6060
tgactactgg aaaaaccata gccttgacta gagagacctt tgttagcaaa gtaatgtctc    6120
```

```
tggcttttta atatgctgtc taggttggtc ataactttcc ttccaaggag caagcatctt    6180
ttaatttcat ggctgcaatc accatctgca gtgattttgg agcccaaaaa aataaagtct    6240
gacactgttt ccactgtttc cccatctatt tcccatgaag tgatgggacc atatgccatg    6300
atctgttttc tgaatgttga gttttaagtc aacttttca ctctcctctt tcactttcct    6360
caagaggctc tttagttctt taccttctgc cataagggtg gtctcattgg catatctgag    6420
gttattgata tttctcccag cagtcttgat tccagcttgt gcttcatcca gcccagcgtt    6480
tctcttgcat gtgtgctata catattgtag ttgtccagta ggggttggat gttcttttt    6540 tttccctctt cagtctttgt tctctttact ttcggatttt cgaggatttt ttttttttt    6600 tagccatgct gtgtggcttt tgggatctta gtcccttgac cagggattga atgtgtgccc    6660
cctgcagtgg aaggttggag tcctaaccac tggactgcca gggaattccc tttatctcca    6720
gcacttcttt tgggttcttt cttatgattt ccctctgctt acaatgcctg ttcttgcagg    6780
ctgtctagaa tccttaccat attaatcaca gttgttttaa aatcctggtc tgataatttt    6840
gtatccctgc cagttctgat gcttgttttg tttcttatg ttaggctttt tgtcttttag    6900
tatgctttgg gatttttttt cttgatagtt agacatatga tgtgctgggt aaaaggaact    6960
gctgtatatg ggccttcgta atgtggtaag gcatggggca ggggaagcat tctacaatct    7020
tatgattagg tcttggtcct ttaataaggg cttccttgga gactcattgg taaagaatac    7080
acctgccaat gcagaagacc agtcgggaag atccctgga caaggaaacg gctgcccact    7140
ctagtattct tgcctgggaa atcccgtaga cagaggagcc tggtgggcta cagtccctgg    7200
ggttgcaaaa gagtcagata tgagttagca gttaaaacac aaaaaaccct ttaatgagcc    7260
tgtagctttg tgcttaggtg gtacaggatg gctaaagtga gctgcagtct agtatttcct    7320
ttcattgagg tcttttaggc tcttgatagt ataccagcag gttaggttct taatgtttat    7380
ttgtgtgttt atttttttatt tgactgcacc agatcattag ttgcaacacg tgggatctag    7440
tgtcccagcc atagattgaa tcccaacccc ctgcattggg agcacagtct taaccggtaa    7500
accaccaggg aagtcccagc agattaggtt ctgattaact agtttccctt gagggcaggc    7560
cttgttaaga ataataaagt actctggcat ttcgaaatga ttccttttct tcctgctgaa    7620
agcaagaggg gtttttttt cccttgatat ttactgtggg aatctggtca agttcctgga    7680
gaaaaacctc acagtattat gaggctttcc tatgagtggt ggtagctctc agagctgtcc    7740
acatggagct tccagcagtt agtcagctgt ggttcagttt cctccacacc actggtttcc    7800
attcctctat ctgttccagt aagtctcgac tccctgtgtt cacctgtctg tgtctgtctc    7860
caatcttgag agcagcactt caccctgtgt cccctcttca gtggatccaa gagagttgat    7920
tttgcagtct gatcagcttt atacttattg gatggagtgc tgacttccaa actccttaca    7980
tgtagaacca gaaacttaga agtctgagtg acttttccgt aagacttcca tttgctctcc    8040
ctgttggaat ttttcttccc attagattcc cagttccagc tacttgcagt ttaggtgaga    8100
ggtgggggcc aggcagttgc aagtgaagca cctggaagaa atagctagca gtggctctag    8160
aaacagaagg ggagatgcct cctctcccga ggggctcagg gctgagagag tgacctccat    8220
atgtaaatca gaggagccct gcttatgaat gaaagttggg ttcgttattg actgtaaacc    8280
aaattgccat taaaaccccc atcgttttat aaatttctat ctaagttcag aaactcagta    8340
ggttaggatg aggcagtggc cttcattaga caatgcagca aatgcgccaa tgttcttgag    8400
ttgtcaagtg ggagtacgta gtgctttgtc caaggagaag tggtgcctta caaggataaa    8460
acgggttttt ttttaatgtt taaaaagatt ttgtacatcc tgctcattta ttcagttcat    8520
```

-continued

```
ggagaccata aacataatat gtaaaggaaa tgtttctgta tgaaaagtaa cttataaaat   8580
ctattaggat tttcaaaaca gtactaatca aaaattctga tcccaagagg gaacaatcgc   8640
atactcataa tgttcatttt aaagaatatt ctgtaattca tggtagtgaa tgaagtttct   8700
ctaggtaaat ttaagtatca tagagtttaa aactttatct cacctttcat tttttttact   8760
caggagttaa caatgcttgg aaaaccgaaa agacctcgct cagcttataa cattttata    8820 gctgaacgtt ttcaggaagc tagggatggc acatcacagg taaaacaaaa ctctgtatgt   8880
tttaaaaatg tttactctaa ttttaaaat aatatagaca ggaaacttta ggggtgcaac    8940
ctgtcaagtg gtgaaaaaaa gtggtaaatt actataaaga aatagtatat ataaataaga   9000
cctaaaaatc cttttcctta ccacataaaa tgtttaaaat ttgaatgtgt tatatataca   9060
tattcagcca tgtatataca tagtcaactt tttaaattaa aaaacaaaat tttcaccttt   9120
ataggagtgt tcaagttctg gagactttc ttatccagca cttctgaatg gttttacaat    9180
cactgggaaa gaatgagaga gagaggtata atgtttcata ctgggatttg agtgtggctt   9240
catgttacgc cctttaaaca ttttttggtta tcccatggga atgtattata ttacacatat  9300
gaatggtatc tatgtctgca gaaagaagaa aacagcttgt cattcttgct gtggcttagt   9360 cttccttta tttccttttt agaggctcca aattgttagt tgtactattc ctcttttaat   9420
atgccatggt aagaaaagtt gtctgctcgg attcctaatt cttgtcagtg tgagatggag   9480
gtttttgcca ctctgattct ttgggttatt tagatctgta gttcatttca cagatcctgt   9540
tggacatatg attaaatgat gtgtatatgt aacgtatttt tctggctata tatgatttca   9600
ctgactactt cccttgggat tttatttttc ttttgaaaag tagtaccatt ttatttagtg   9660
ttgtaggaca tcgtaggtta cttctgaaaa acaaaagggg gatcttctcg gaccagggat   9720
tgaacccatg tctcctgcat tggcaggtgg attcttagca ctgagccacc agggaagccc   9780
tggattttaa atttagtttc catggcccta cattactaaa acagcaagcc tgtttatttt   9840
tttagttgga atttgctcag tcactaacta actttggatt tcattttatt agtataagaa   9900
ggttttgtgt tagagaatcc ttctgaatca gtagttctca actctgactg catcttggaa   9960
tcacctcaga agcttcctgg ctggccttta tctctgaaat taaaattaat ttaattctat  10020 cattttatt catgtaaaaa agtgcattct catagtttta aagaatcaaa tgaggcttgt   10080
tatgaaagac acaagtttcc ctgtgccgtc atgttcctca ctccagaagc aaatgcattc   10140
tgttttagtt gattccttgta gtatttaccc ccatgtctct aagtaatgtt cctccattgt  10200
cacgtcctga ttttctaaa attctaagcg ttacctatat tttaggcatt ccctctcact    10260
gtgtaaggtg agcgttaact ctgtctcatc gcactgttca ctcttctgtc agtctgcctc   10320
ccaatatagt tacataattt gggttagatc agtattgagt acttaatact atgatgtgtg   10380
catgctaatt tgcttagtc atatccgact ctttgtgacc ctgtggactg tagccttcca    10440
ggctcctctg tccatgggat tctagagaca agaatactgg agtgggttgc catgccctcc   10500 tccagggat cttcctgacc cagggatcaa accagtgtct cttaaatctc ctgcattggc    10560
aggtggattc tttaccacta acgccatctg ggaagctcag tggctcagcc agtaaagaat   10620
ctgcctggag aggagagccg ggtttgatcc ctgggtcaga aagaatcccc tggggaaagc   10680
aatggctacc taccccagta ttcttgcctg gagagtgcca gggacagagg agcctggaag   10740
gctatggtcc atcgggttgc agagttggac gcaactaagc gactaacgct ttctgcactt   10800
agagcgtgga attagctctg cttttctgct ccccaaaatgc tgtgttggta gtgtcctttc  10860
```

```
ctattgtctt tgtcgctgtg gattttatgc ctttagaaat tttagttgtt taattaaaaa    10920
aaataaatca cagaaatgaa ttgcttacag ttctgaaggt taaaagtcca cgatcaaggc    10980
cacatcctgg tgagggccct cttctgcttc atagctggca ccttctctct ctgtgtcctc    11040
acatggtgtg agtgctcatt taatgtgatt ttagatagca ccagaagtaa ataccttccc    11100
atccctttaa tttgttttcc atgaattagt ttttaggtg aaagattgtt tatgcatgca     11160
gcttcataaa ttattgttta acacactgaa tatgaaactt gtggattaaa tataagcaaa    11220
aagatacgtt atgaaagaac taaaagcatg aaagcaattc tttccaaagc taagagagca    11280
gttatttaat gagtaaccat ccctgaatat actagatgta tttataaagg gaagcttaaa    11340
atactcaaaa taggctcaga taccatctgg gtacctcact ttttgttgat aggaaaacaa    11400
aattcagtga aagttctggt cagaatagta agttaatag ttctaactct acttcttaaa     11460
atcactgatg atatcctcct gcctttaata ggcacttttc atcccctct ccctcacatt     11520
ctccgcctct ctctctcctt cttctctgct cctcattctc cacccgccca ttttcctctt    11580
cagtctttgc tctccggtag cagcaccaca ggctgtgtga ggtgtactca ctgtctctct    11640
gcctctcctc caaatatggg attcctgcat ccctttaatt ttatagatta aagctcccaa    11700
gcctaaggga ggtcatagaa cttttttccgg gtcacatagt taagctcagc tgtgtaggag    11760
gagaatcggc gctgtgttgc tcctgtggtg acaactgaaa cacagtgcac agacatgaga    11820
ggtcagagag cacttaagcc acagaggaga caaaacagta tttgaggcta gtctgtgaca    11880
gagtagctta tatttgaata ttaatatctt tgaattcaaa aagataaata tctgcacaaa    11940
caaaggaacc atcaacaaaa tgaaaagtaa tcctaccaaa tgggagaaaa taatttgcaa    12000
ataatttaga gaactcatat gactcattcc cccaccccg aagaaaaaaa tctgattaaa     12060
aaatgggcaa aggatccgaa tagatatttt cccaaagaag acttagagat ggctaacaag    12120
tatatgaaaa ggtgctcaac atcattgtca gggaaatgta aagcaaaact acaatgaagt    12180
actccctcat atttcttaga atggctctta taaaaaacaa gtactactga agctgcagta    12240
gaaggggaac ccttgtgctg aaacagtaac tcagaacaca tagacacgag caacacgttg    12300
gtgactgcgc gagttgctgg gtggggtggg agggtggaat gggcaaaggt ggtcgaaggg    12360
cacagacttc acaagcgctg cactgcacac ctgaatgtat tgttacatgt tagttacagc    12420
tcagagtttt gaggagtctt tgcctgtgat tcttgatatc tgagtgtgtg tggttggaat    12480
gaataataaa acagcatctt tcttcaatca ctgaagtccc tgtatctggt acttaagtgt    12540
atattgtttt acaggtaaag ctgaaagcta taatgaaaa ctggaaaaat ctctctaatt     12600
ctcaaaagca agtaagtagt atggttttag tcccaagtgc ctagttagag tatctgtgag    12660
aatatatcag ggcaaggctt gattcatgtg aaaacaactt tatattacac agtgttttaa    12720
aatcattgtc atattcttgg aaccagtttg gctttttttct tttggtagtt tttgattcca    12780
tatcaaacgg gtatttaaaa cagtgtccct cgtaacttag tgtcatcata tccagtaatg    12840
atcacaccct gccctgttg cttttccaca ctccaaaccc tgaaattgta gcgacttcat     12900
gaatacttaa aaacctttat ctcttatctg tttctcatct aattttttatc tcacaagaat   12960
atttctttcc agccccccctt taacatatag aatagtaaaa taatttctag aatattttg    13020
gagagcatcc cagaaattaa ctgcaaagat tcctctaaag aaatcatttt aacaattaca    13080
ctctttctca ggtatatatt cagcttgcta aagatgataa aattcgttat tataacgaaa    13140
tgaaatcttg ggaggaacaa atgatggaag ttggacgaga agatcttata cgtcgctcaa    13200
ttaaataccc agcaaaaaat gaccctgaga agttttaaaa tagaagattg agttatgttc    13260
```

```
ataatggata gacataagaa accaactagg tctcaatacc ggaagctgtt gtaaaattag    13320
aatggataaa gttggtgaac atttatattt aattccttt ctgtagccca tggacttctg     13380
ccagccaatt caatacattt tgtattggtg tcttgctttt gaaaacccaa acagataaga    13440
cttcatgtgg aatttatttt gtgtttagga actactgagc atcaaaataa tccatgaaat    13500
gtagcagtga atcattttac ctttgataaa ggtaaatcag actgtgaagt ttttttatac    13560
ttggtgatta tggaaaaaat attcttgttt ccttatatta tggaagcagg agtttcctat    13620
tcataagtat ctcaaagttt gtagaagcca tagtgttcta tgatataact gcattttaa     13680 aagagcatcc agaactcatg ctggtaaatt ccaaatcctg ggtataattc atattataat    13740
cagacttgat ggttgtacat gtgaggaatt tctggtatca gttgcagctt ttataaaagg    13800
tatagattta taaaccttt cctcattatc tttttcctaa attaaaaact aaaaaattat     13860
gtaccaaatc tatgcatatt gttttatatt gcatagaata aaaattatgt gtttcctaat    13920
tatgttttaa ggtgaaacat tcattttata gctttctggg attttgttt gttttttaa      13980 acaaagtagg agtttgtata ctgaattatt ttttctctta tgtaaatata tttatccaga    14040
aagtagagaa cttatttggt gtaagttta aaatgagaga tctaaaaaa tcatgtctcc      14100 aaagtctctc aaattggaac ctataatttt taaacatttg cataacatat aaaagcctgt    14160
ataataatta atagccagtt ctagcctgat gcccacatcc agcccactgc ctgcttttct    14220
tggccttgtc aactaagaat tgttcacagt tttaaatagt taaaaaaaac taagcatact    14280
tcaagacaca tgaaaattaa tatgaaattc agtgtccata aaaaaatgtt ttattggaac    14340
acagccacac tcatcgatta tggctgtttt tgtacaatag tgcagttgac ttggttgcta    14400
cagagaggtg cagcctgcaa agactgaccc gtatagtgtg gaatgagatg ctcttaagtt    14460
acttgctgtg gctcagtaaa atacatctta acagttttcc agttagcatt taaaccttac    14520
cccttctagc atttgattat cttcttaaca agagtcaaag gttttcaaa atccacacca     14580 cctttttgag caaaatattc aactgtcatc atcagttcac atgaatttat aactcaaaat    14640
ttatatattt actttgtatt ttgcaaaaat atgcaaaaaa aaataaaagt gtatattcta    14700
catctccaga aagaagattt ttgaagtttg tggatagaaa ataagtaaaa gaatcactaa    14760
aaaatgactt gttacgtact gaacttggca aaggtcagga ctgtagggaa aactacaact    14820
taagaggact agcctaagat ttaaatatat ggagctgttt gaagttttca ggcggctttg    14880
ctctctgaat ggtaatgcag gacacagcct gccagtatgt aaatgaccct tggtctgagg    14940
ctagagtgtt ctggggaaga agagagggaa gaaaaggaca cgtgctagtg tctctcccaa    15000
gctttctcag ttaggtttcc aggagagaat taagccctaa ttccctgggg catctagaat    15060
ggtaccaatt ttgtaccagc cttaggagaa tggagaaaat aatcactcaa ataatttact    15120
gtgttctgtg cttcagatga gcccagggag cacatgggag tcgatgttta taatattata    15180
gaatgggtga ggaagagaaa tgaattataa actcctgtag cacaaatgta taaaacacat    15240
ctgcgtactt accttctgag ctctaggcat ttagctgcct gtactgtttt acaccgaaca    15300
cattcaaata tccagtgtct acgttctcat gtatatactt aatatatggga ggacaggtat   15360 gaaacagtga aaggagctgt agcaaaaccg ttttgtttct aaaagggtgt cattgttaat    15420
actttaaata ttaggataat ctgatttcac acctttctta ataaacttca gtacatggca    15480
taccatgtat taaatgccat ccatttgtat atacaaatac tctgttatga agaatgagag    15540
cgtatatcaa taaccagtgg ctaggtgtgt aaccggtggc cattcttata ttggctgaac    15600
```

-continued

```
aagaaactaa aagctaaaga attgtgacca gggaaaagat gcttaagtga aaacagcgtt    15660
tatgctgtct gagcagtcag tcacagagac gcttatgttc actagagtac cagtattaga    15720
ttttataaaa caattgacaa gggtgtgtgt aattattttc tgatgtttaa ggtatatgtg    15780
cagattcagc ctactgtaat aatgtaattt tgccattgct tttggctaac tccttttttg    15840
gaaatgccct tttttttttt ttaatgtata tgctttttta aatagttggc catgaatgtg    15900
tatatttaca tttctgaatt aaaatgcagt taaagtaact ggcaagtttt attgatattt    15960
gtgacattta ctgtacctga aattaatcac caccagattg tccgaaagca gcaggaactt    16020
cttatatagg taagtaacta atttccatta tttctcttaa ttttaccaat cttttttactg    16080 taagactact ccaacaacaa caacaaaaat actcttttct ttccttttct ctcctcacag    16140
ccactattcc tcttcctttt caaagcacca agctcttaca gacaaatttg aaaatgttac    16200
aagtgcagat aatatgtttt gaaattttaa agcagtaata ctcttttaaa ttgaactttg    16260
gggaagaata agaaatgaac gtatttatta ttattttcaa tttgtaaaat tttccaaata    16320
gtaaaactgt acaaagttag tatcatcatt ctctcacatt gttcacaaat aaaatatttt    16380
tggtaatcat tgattatatt tgatggcaaa tacataaaac atgaaaccat cttctagcac    16440
attaaaaata ctttaaaaaa tttttactgg ctaaaaaact acatacttaa aattgactgt    16500
aaacaaaatt ttaaataggc taaacattta aaaattaccc taatggcaga agtaaagaa     16560 gaactaaaga gcctcttgaa ggtgagagag gagagtgaaa aagctggctt gaaactcaac    16620
attcaaaaaa ctaaggtaat tgcatctgtt cccatcactt tatggc                   16666
```

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
gttgttgcag aaatcagcta aaatg                                          25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
catccactga gactatcgct gacct                                          25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
cgcctcctag ctaatcggaa gttag                                          25

<210> SEQ ID NO 7
<211> LENGTH: 25
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 7
gtcggaatca cagggctaag tcagt                                          25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttcccctgga taggacagga tttta                                          25

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tacaggccat cacacagaat ggtta                                          25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gagctaatgg attattcttt cctga                                          25

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atgtgttatc caaggtgaag gtcta                                          25

<210> SEQ ID NO 12
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ttataagtgg gatttcagag tgcat                                          25

<210> SEQ ID NO 13
<211> LENGTH: 25
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 13
aactgaagtc attctctacc acgtc                                           25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aacaatcgca tactcataat gttca                                           25

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tggtaagaaa aaggattttt aggtc                                           25

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcacaaacaa aggaaccatc aa                                              22

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttccctgaca atgatgttga gc                                              22

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tacagctcag agttttgagg agtct                                           25

<210> SEQ ID NO 19
<211> LENGTH: 25
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 19
cactaagtta cgagggacac tgttt                                              25

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
tgaaaactgg aaaaatctct cta                                                23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aacagcttcc ggtattgaga cct                                                23

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Met Gln Trp Arg Phe Ser Gly Ala Tyr Gly Ala Cys
 1               5                  10

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
agatttggcc agatgaccta aaag                                               24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 24
agatttggac agatgatcta aaag                                               24

<210> SEQ ID NO 25
<211> LENGTH: 13
<212> TYPE: DNA
<213> ORGANISM: Artificial Sequence
<220> FEATURE:
```

```
-continued

<223> OTHER INFORMATION: Description of Artificial Sequence: Synthetic
      oligonucleotide

<400> SEQUENCE: 25
tagaagcgtc ctt                                                              13

<210> SEQ ID NO 26
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
tagaagtgtc ctt                                                              13

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
acaacctgct at                                                               12

<210> SEQ ID NO 28
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)
<223> OTHER INFORMATION: a, c, g, t, unknown or other

<400> SEQUENCE: 28
caggtgnctt atc                                                              13
```